(12) United States Patent
Sagisaka et al.

(10) Patent No.: US 10,096,103 B2
(45) Date of Patent: Oct. 9, 2018

(54) IMAGE PROCESSING SENSOR, IMAGE PROCESSING METHOD, IMAGE PROCESSING PROGRAM, AND COMPUTER-READABLE RECORDING MEDIUM AND DEVICE HAVING IMAGE PROCESSING PROGRAM RECORDED THEREIN

(71) Applicant: Keyence Corporation, Osaka (JP)

(72) Inventors: Hiroshi Sagisaka, Osaka (JP); Fumitaka Yamaoka, Osaka (JP)

(73) Assignee: Keyence Corporation, Osaka (JP)

( * ) Notice: Subject to any disclaimer, the term of this patent is extended or adjusted under 35 U.S.C. 154(b) by 0 days.

(21) Appl. No.: 15/585,182

(22) Filed: May 3, 2017

(65) Prior Publication Data

US 2017/0358069 A1    Dec. 14, 2017

(30) Foreign Application Priority Data

Jun. 13, 2016    (JP) .................................. 2016-117054

(51) Int. Cl.
| | |
|---|---|
| *G01N 21/00* | (2006.01) |
| *G06T 7/00* | (2017.01) |
| *G01N 21/88* | (2006.01) |
| *H01L 21/66* | (2006.01) |

(52) U.S. Cl.
CPC ......... *G06T 7/001* (2013.01); *G01N 21/8851* (2013.01); *H01L 22/12* (2013.01); *G01N 2021/8887* (2013.01)

(58) Field of Classification Search
CPC .. G06T 7/00; G06T 7/001; G06T 7/30; G06T 7/40; G06T 7/60; G06T 7/70; G06T 7/33; G01N 21/88; G01N 21/8851; G01N 2021/8887; H01L 21/66; H01L 22/12; G06K 9/00; G06K 9/46; G06K 9/62; H04N 5/232; H04N 5/235
See application file for complete search history.

(56) References Cited

U.S. PATENT DOCUMENTS

| | | | |
|---|---|---|---|
| 2015/0355102 A1* | 12/2015 | Kido | G01N 21/8851 348/46 |
| 2017/0358070 A1 | 12/2017 | Sagisaka | |
| 2017/0358071 A1 | 12/2017 | Yamaoka et al. | |

FOREIGN PATENT DOCUMENTS

JP    H11-312249    11/1999

* cited by examiner

*Primary Examiner* — Jamil Ahmed
(74) *Attorney, Agent, or Firm* — Kilyk & Bowersox, P.L.L.C.

(57) ABSTRACT

An image processing sensor includes a threshold calculating unit configured to calculate a threshold with respect to a matching degree indicating a degree of feature matching of a first image including an inspection target object that should be distinguished as a non-defective product and a second image not including the inspection target object that should be distinguished as the non-defective product and a display control unit configured to cause a display unit to display the first image and the second image as images used for the calculation of the threshold by the threshold calculating unit. The display control unit causes the display unit to display, on a first registration screen, as a live image, the one image acquired by the imaging unit, and causes the display unit to display, on a second registration screen, as the live image, the other image acquired by the imaging unit and, as a still image, the already registered one image.

22 Claims, 41 Drawing Sheets

FIG. 20
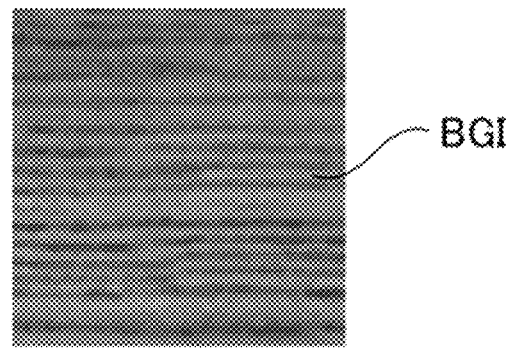
FIG. 21
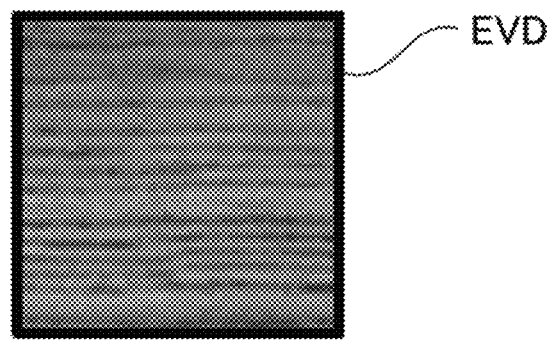
FIG. 22
| MATCHING DEGREE OF DEFECTIVE PRODUCT IMAGE | | MATCHING DEGREE THRESHOLD TO BE SET | |
|---|---|---|---|
| 80 | → | 90 | ⋯ (100+80)/2 |
| 70 | → | 85 | ⋯ (100+70)/2 |
| 60 | → | 80 | ⋯ (100+60)/2 |
| 50 | → | 75 | ⋯ (100+50)/2 |

FIG. 37B

OPERATION SCREEN COMMON OPERATION

▲▼ SHORT-PRESS (*)
CHANGE SETTING VALUE

* 1) WHEN ▲ AND ▼ KEYS ARE PRESSED ON SCREENS C TO F, SETTING VALUE IS DISPLAYED AND CHANGED
RETURN TO ORIGINAL DISPLAY ** SECONDS AFTER KEY DEPRESSION

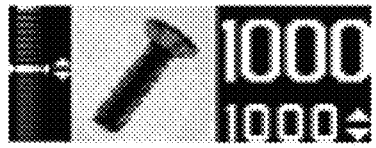

SET SHORT-PRESS
  TO TWO-POINT TEACH SCREEN

SET LONG-PRESS
  TTO THREE-POINT TEACH SCREEN

MODE LONG-PRESS
  TO SETTING SCREEN

MODE+▼ SHORT-PRESS
  bank, OUTPUT ch CHANGE
  (TO NEXT)
MODE+▲ SHORT-PRESS
  bank, OUTPUT ch CHANGE
  (TO PREVIOUS)
    WHEN standard OUTPUT
    SETTING OF ch2 IS
    PERFORMED,
    CHANGE IN ORDER OF
    Bank1/ch1 → Bank1/ch2
    → Bank2/ch1

WHEN BANK CHANGE IS PERFORMED, THIS SCREEN IS DISPLAYED FOR ** SECONDS AFTER CHANGE

MODE+BACK LONG-PRESS
  KEY LOCK/RELEASE KEY LOCK

MODE+SET×5 TIMES
  INITIAL RESET

FIG. 42

| 0  | 10 | 20 | 30 | 40 | 50 |
|----|----|----|----|----|----|
| 10 | 20 | 30 | 40 | 50 | 60 |
| 20 | 30 | 40 | 50 | 60 | 70 |
| 30 | 40 | 50 | 60 | 70 | 80 |
| 40 | 50 | 60 | 70 | 80 | 90 |
| 50 | 60 | 70 | 80 | 90 |    |

→

| 10 | 30 | 50 |  |
|----|----|----|--|
| 30 | 50 | 70 |  |
| 50 | 70 | 90 |  |
|    |    |    |  |

FIG. 43

| 0  | 10 | 20 | 30 | 40 | 50 |
|----|----|----|----|----|----|
| 10 | 20 | 30 | 40 | 50 | 60 |
| 20 | 30 | 40 | 50 | 60 | 70 |
| 30 | 40 | 50 | 60 | 70 | 80 |
| 40 | 50 | 60 | 70 | 80 | 90 |
| 50 | 60 | 70 | 80 | 90 |    |

→

| 0  | 20 | 40 |  |
|----|----|----|--|
| 20 | 40 | 60 |  |
| 40 | 60 | 80 |  |
|    |    |    |  |

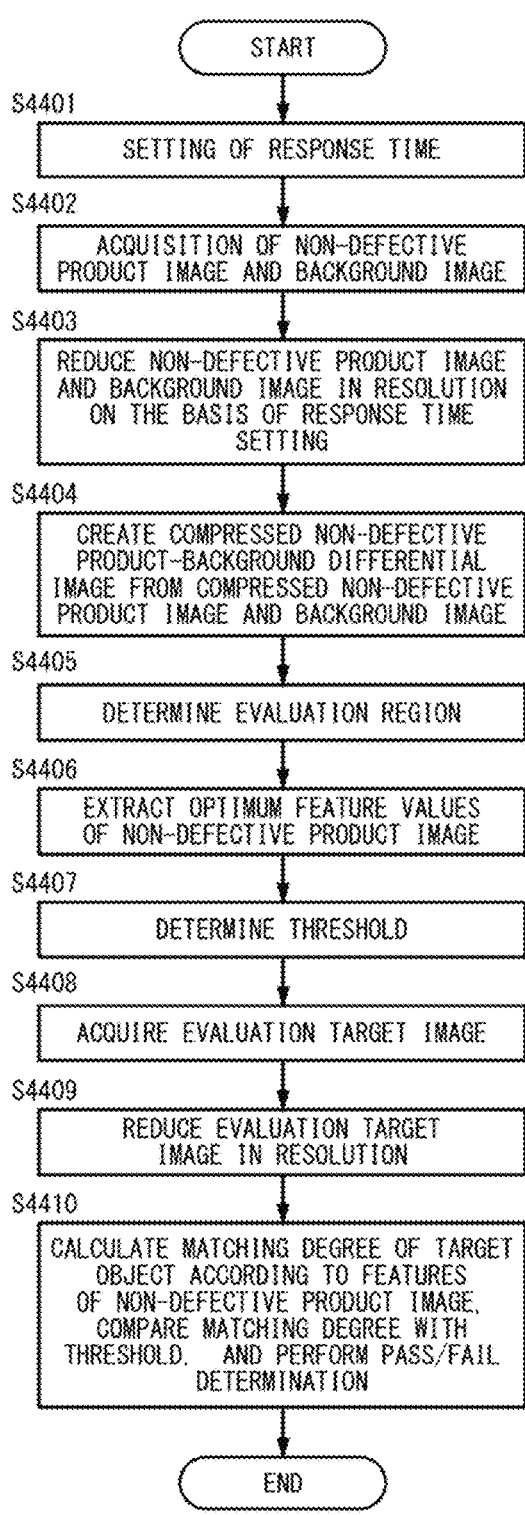

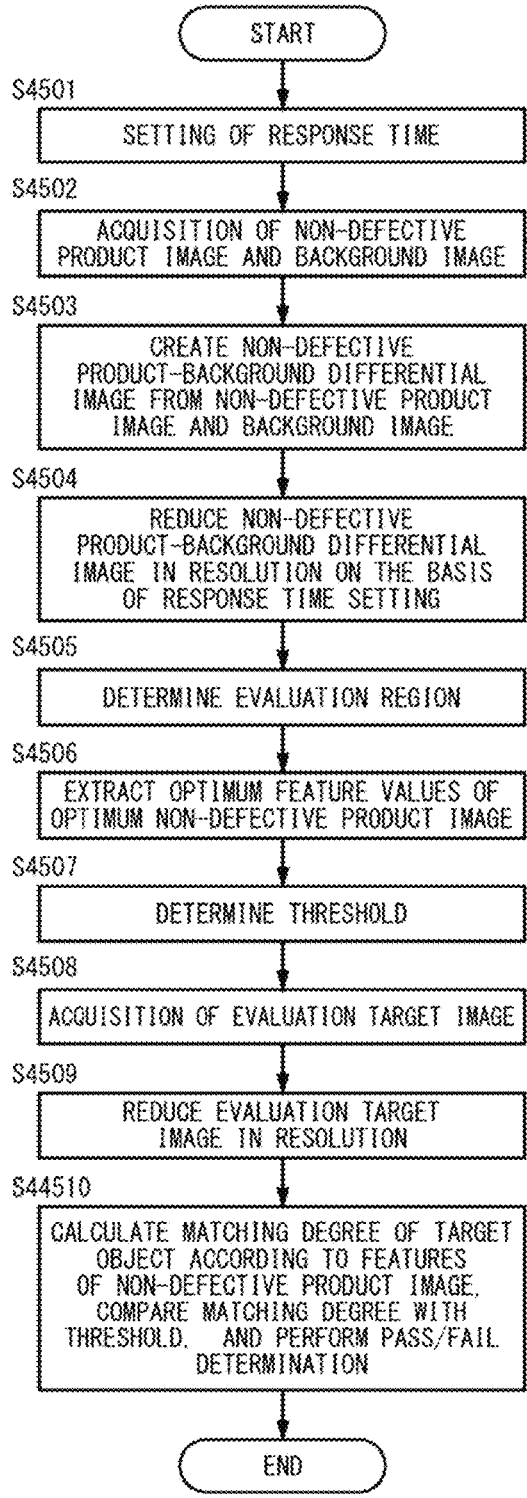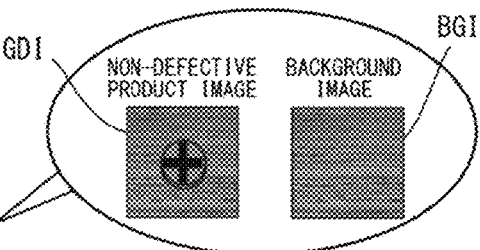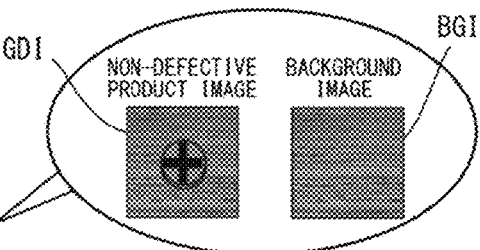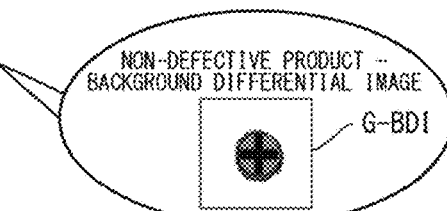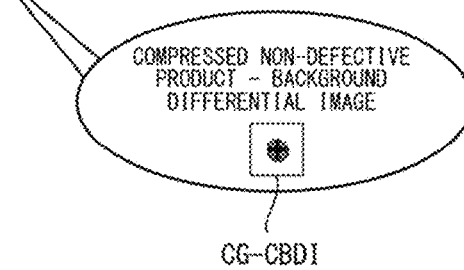
FIG. 45A
FIG. 45B
FIG. 45C
FIG. 45D
FIG. 45E

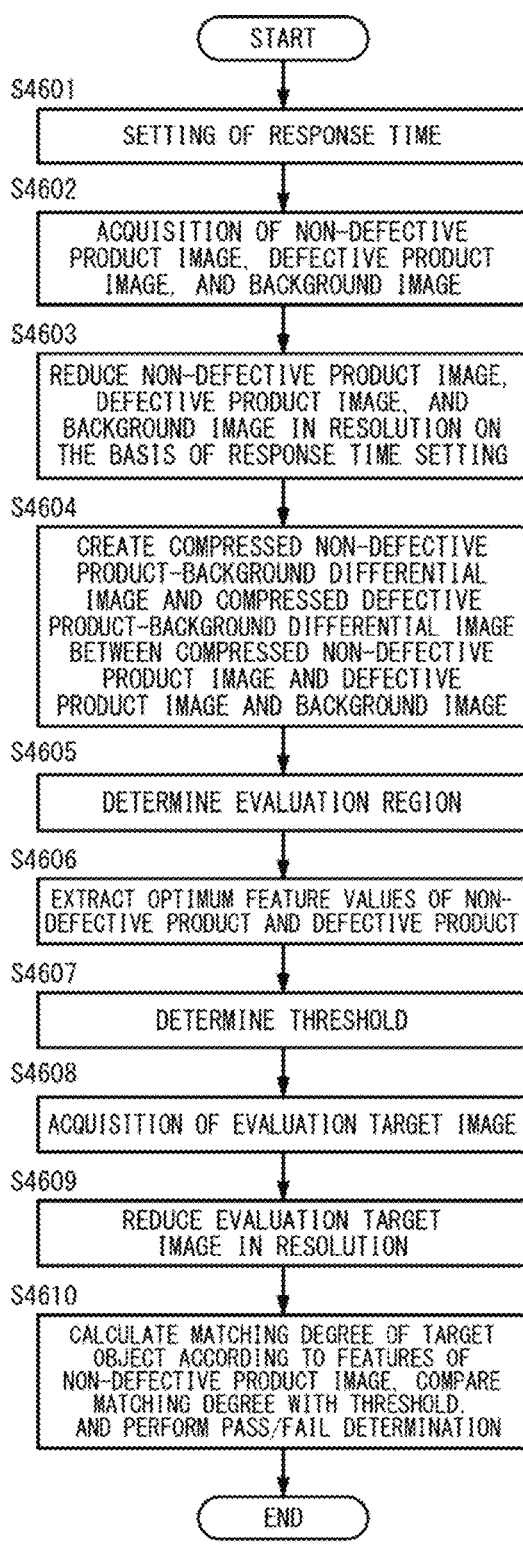

FIG. 46A

- S4601: SETTING OF RESPONSE TIME
- S4602: ACQUISITION OF NON-DEFECTIVE PRODUCT IMAGE, DEFECTIVE PRODUCT IMAGE, AND BACKGROUND IMAGE
- S4603: REDUCE NON-DEFECTIVE PRODUCT IMAGE, DEFECTIVE PRODUCT IMAGE, AND BACKGROUND IMAGE IN RESOLUTION ON THE BASIS OF RESPONSE TIME SETTING
- S4604: CREATE COMPRESSED NON-DEFECTIVE PRODUCT–BACKGROUND DIFFERENTIAL IMAGE AND COMPRESSED DEFECTIVE PRODUCT–BACKGROUND DIFFERENTIAL IMAGE BETWEEN COMPRESSED NON-DEFECTIVE PRODUCT IMAGE AND DEFECTIVE PRODUCT IMAGE AND BACKGROUND IMAGE
- S4605: DETERMINE EVALUATION REGION
- S4606: EXTRACT OPTIMUM FEATURE VALUES OF NON-DEFECTIVE PRODUCT AND DEFECTIVE PRODUCT
- S4607: DETERMINE THRESHOLD
- S4608: ACQUISITION OF EVALUATION TARGET IMAGE
- S4609: REDUCE EVALUATION TARGET IMAGE IN RESOLUTION
- S4610: CALCULATE MATCHING DEGREE OF TARGET OBJECT ACCORDING TO FEATURES OF NON-DEFECTIVE PRODUCT IMAGE, COMPARE MATCHING DEGREE WITH THRESHOLD, AND PERFORM PASS/FAIL DETERMINATION

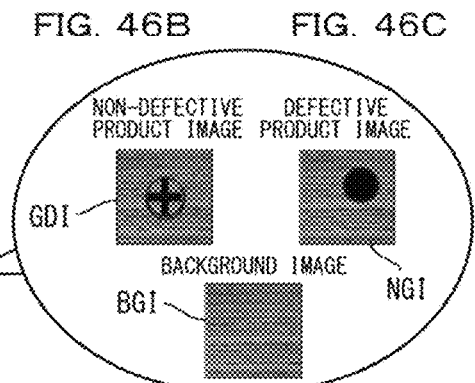

FIG. 46B  FIG. 46C

NON-DEFECTIVE PRODUCT IMAGE — GDI
DEFECTIVE PRODUCT IMAGE — NGI
BACKGROUND IMAGE — BGI

FIG. 46D

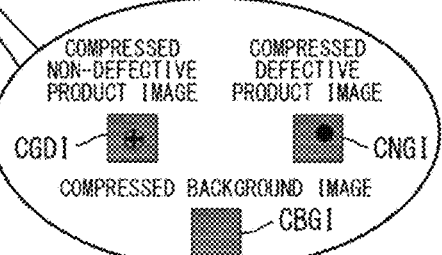

FIG. 46E  FIG. 46F

COMPRESSED NON-DEFECTIVE PRODUCT IMAGE — CGDI
COMPRESSED DEFECTIVE PRODUCT IMAGE — CNGI
COMPRESSED BACKGROUND IMAGE — CBGI

FIG. 46G

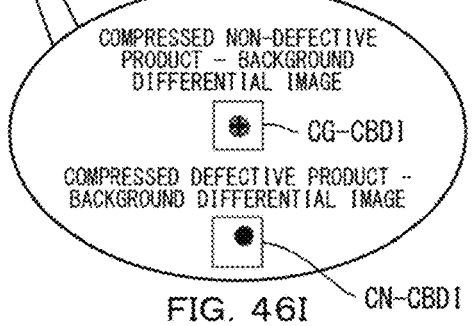

FIG. 46H

COMPRESSED NON-DEFECTIVE PRODUCT – BACKGROUND DIFFERENTIAL IMAGE — CG-CBDI

COMPRESSED DEFECTIVE PRODUCT – BACKGROUND DIFFERENTIAL IMAGE — CN-CBDI

FIG. 46I

FIG. 47A
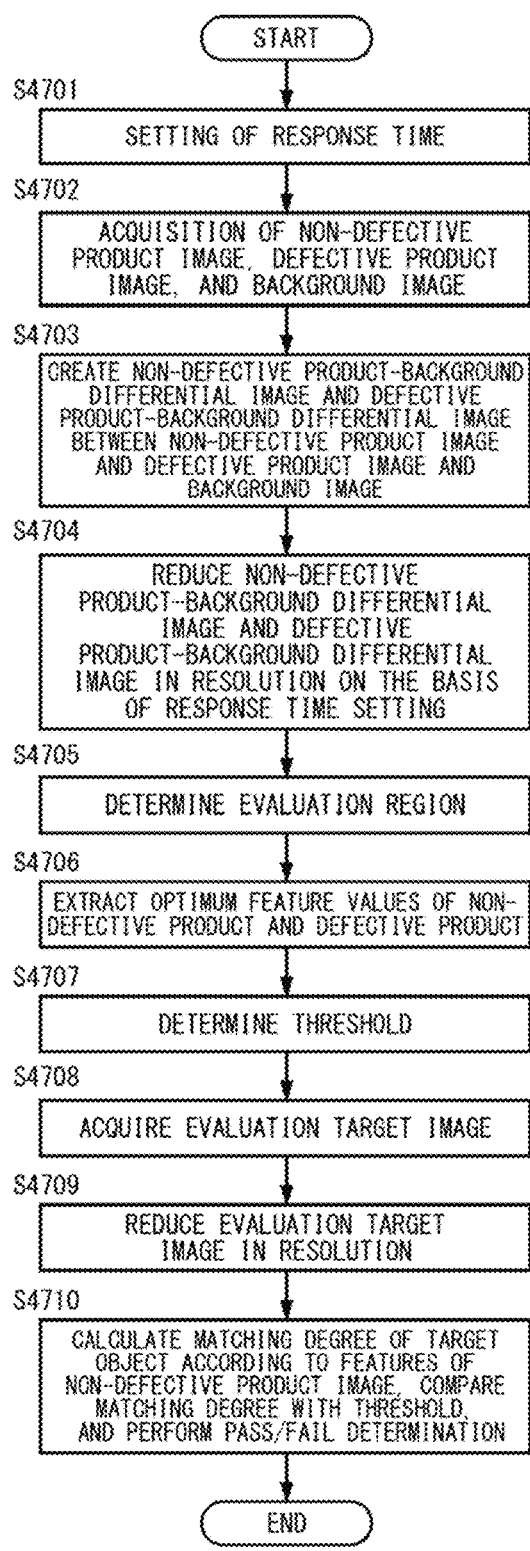
FIG. 47B  FIG. 47C
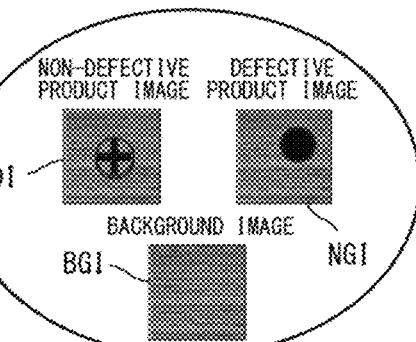
FIG. 47D
FIG. 47E
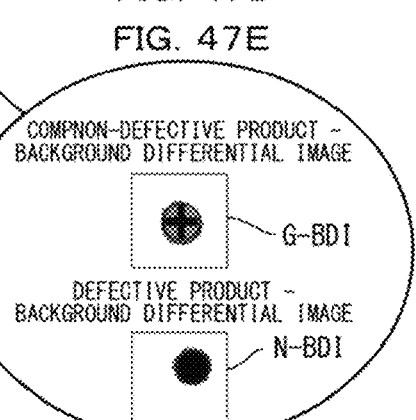
FIG. 47F
FIG. 47G
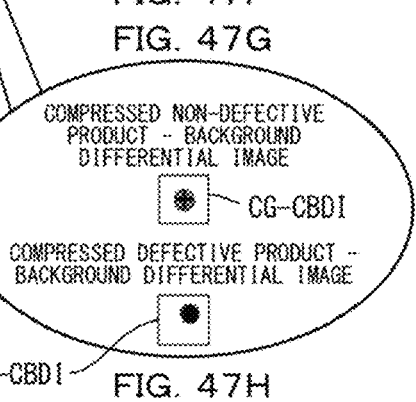
FIG. 47H

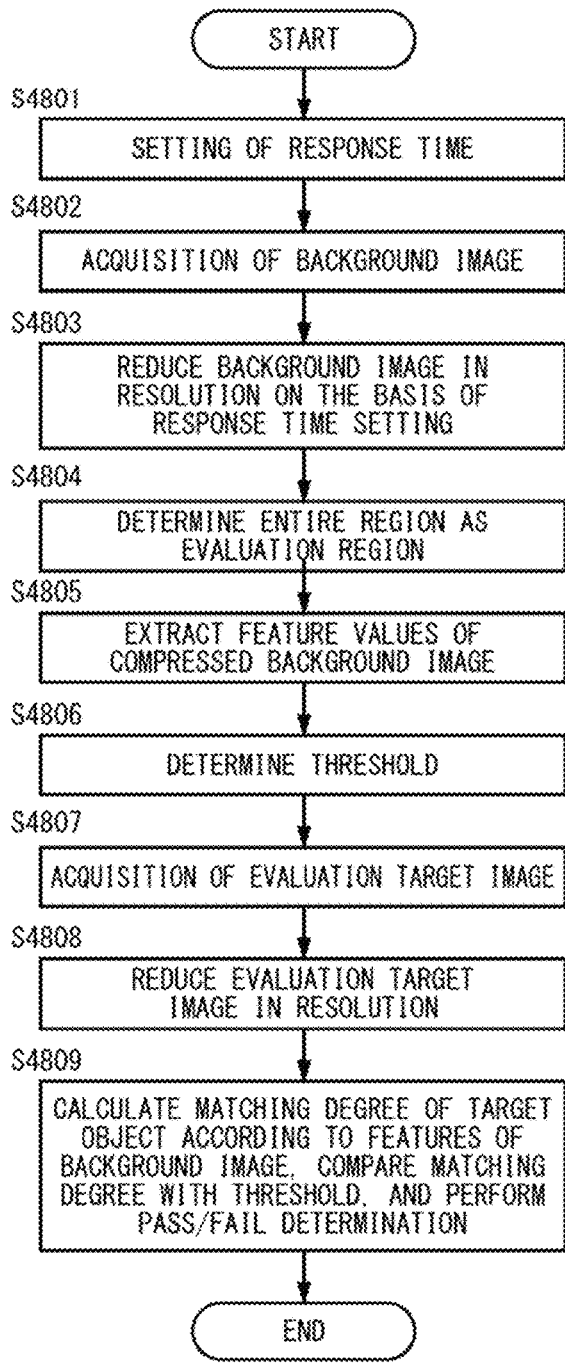
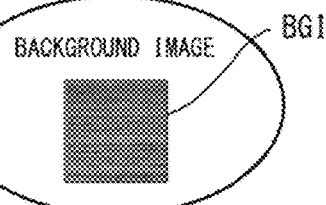
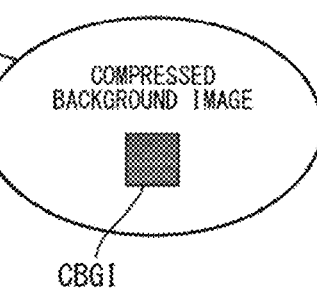
FIG. 48A
FIG. 48B
FIG. 48C

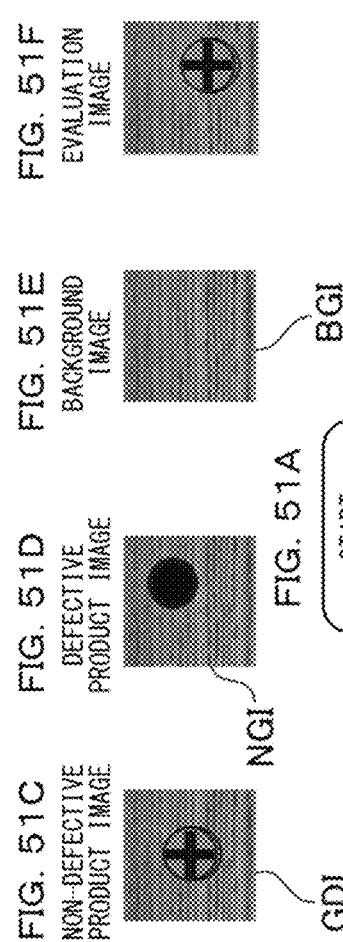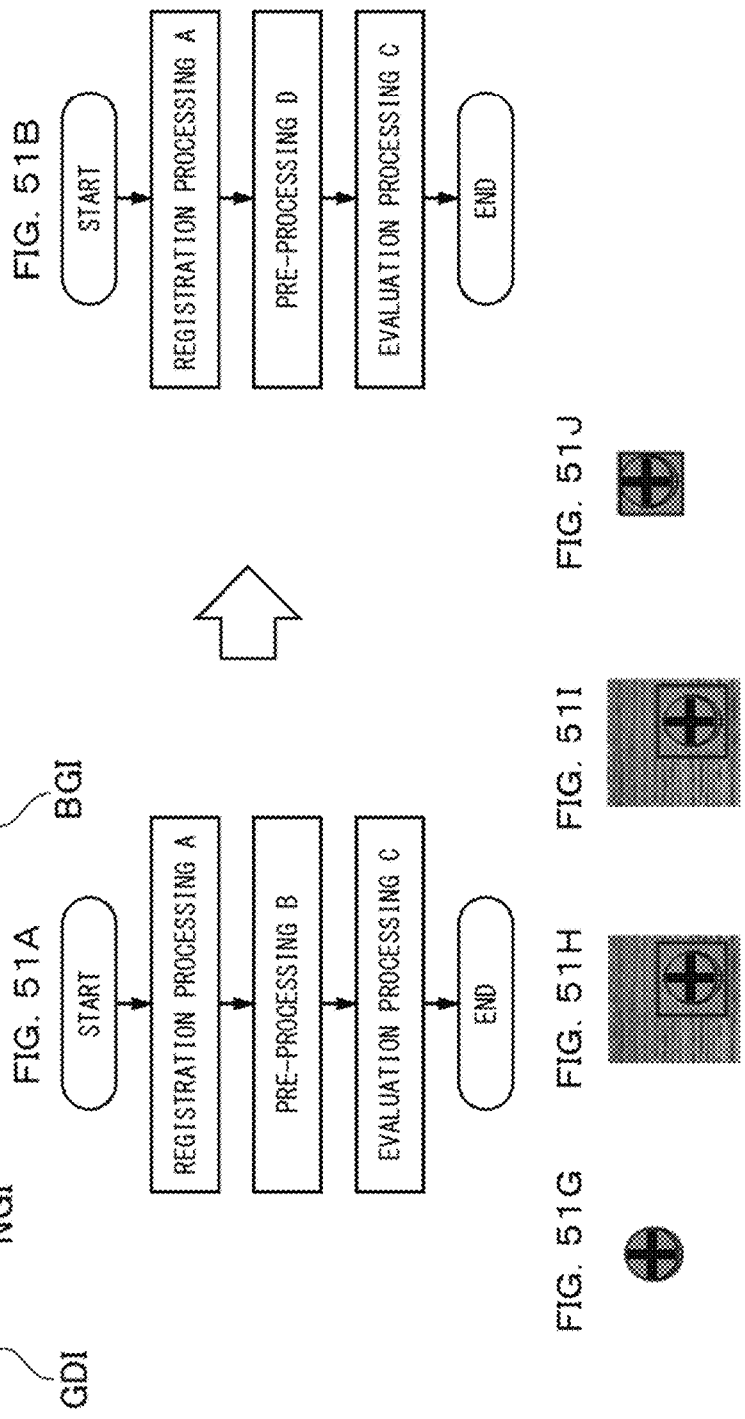

FIG. 53A
Sobel X
| -1 | 0 | 1 |
|----|---|---|
| -2 | 0 | 2 |
| -1 | 0 | 1 |
FIG. 53B
Sobel Y
| -1 | -2 | -1 |
|----|----|----|
| 0  | 0  | 0  |
| 1  | 2  | 1  |
FIG. 53C
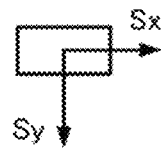
FIG. 54A
Roberts X
| 0 | -1 |
|---|----|
| 1 | 0  |
FIG. 54B
Roberts Y
| -1 | 0 |
|----|---|
| 0  | 1 |
FIG. 54C
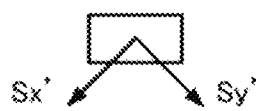
FIG. 55
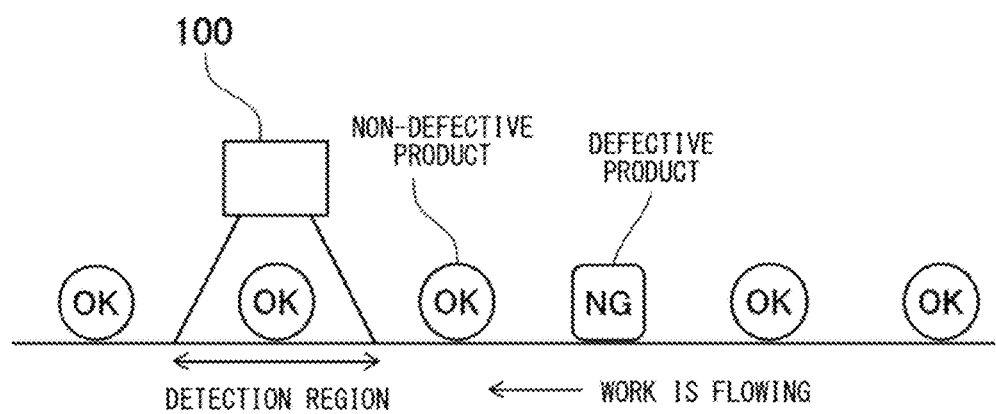

IMAGE PROCESSING SENSOR, IMAGE PROCESSING METHOD, IMAGE PROCESSING PROGRAM, AND COMPUTER-READABLE RECORDING MEDIUM AND DEVICE HAVING IMAGE PROCESSING PROGRAM RECORDED THEREIN

CROSS-REFERENCE TO RELATED APPLICATIONS

The present application claims foreign priority based on Japanese Patent Application No. 2016-117054, filed Jun. 13, 2016, the contents of which is incorporated herein by reference.

BACKGROUND OF THE INVENTION

1. Field of the Invention

The present invention relates to an image processing sensor, an image processing method, an image processing program, and a computer-readable recording medium and a device having the image processing program recorded therein.

2. Description of Related Art

An image processing sensor is set in various forms. For example, as a member for inspecting the exterior of an inspection target object visually, the image processing sensor is set near a conveyance line on which the inspection target object is conveyed or is incorporated in a test apparatus.

For example, the image processing sensor images, as the inspection target object, work flowing on a production line and detects presence or absence of a defect of the work on the basis of obtained images and a preset threshold to thereby perform pass/fail determination of the work. A user needs to acquire an image obtained by imaging non-defective work in advance and register the image as a model image. This work is called teaching (e.g., JP-A-11-312249).

However, in such an image processing sensor, since the teaching is performed by only the registration of the model image, for example, registration of a non-model image not including the non-defective work cannot be performed. Therefore, the threshold used for the pass/fail determination of the work has to be calculated only from the model image. It is not easy to determine a threshold that can stably separate a non-defective product and a defective product. For example, it is likely that defect detection accuracy is deteriorated because of a background element reflected in the model image and an illumination environment during model image acquisition. Even if two images, that is, a model image and a non-model image can be registered, when the images are registered, it is difficult to perform registration to clarify a difference.

SUMMARY OF THE INVENTION

An object of the present invention is to provide an image processing sensor, an image processing method, an image processing program, and a computer-readable recording medium and a device having the image processing program recorded therein that make it possible to easily perform registration of images necessary for stably separating a non-defective product and a defective-product.

An image processing sensor according to a first aspect of the present invention is an image processing sensor for performing predetermined image processing on an image of an inspection target object to detect that the inspection target object is a non-defective product or a defective product. The image processing sensor includes: an imaging unit configured to image the inspection target object; a display unit configured to display an image of the inspection target object acquired by the imaging unit; an operation unit configured to receive an instruction for registering the image displayed by the display unit; a threshold calculating unit configured to calculate a threshold with respect to a matching degree indicating a degree of feature matching of a first image including the inspection target object that should be distinguished as the non-defective product and a second image not including the inspection target object that should be distinguished as the non-defective product, the first image and the second image being registered according to the instruction received by the operation unit; and a display control unit configured to cause the display unit to display the first image and the second image as images used for the calculation of the threshold by the threshold calculating unit. The display control unit causes the display unit to display, on a first registration screen for registering one image of the first image and the second image, as a live image, the one image acquired by the imaging unit and, after receiving, with the operation unit, an instruction for registering the one image, causes the display unit to display, on a second registration screen for registering the other image, as the live image, the other image acquired by the imaging unit and, as a still image, the already registered one image. With the configuration explained above, when an image of a product that is not the non-defective product is registered, by causing the display unit to display, as the still image, a non-defective product image captured in advance, it is possible to register the image while causing the display unit to clearly display a difference desired to be detected between the image and the non-defective product image. Portions without a difference in the non-defective product image and the image of the product that is not the non-defective product are disposed similarly. Consequently, it is possible to more clearly distinguish the difference.

An image processing sensor according to a second aspect of the present invention is an image processing sensor for performing predetermined image processing on an image of an inspection target object to detect that the inspection target object is a non-defective product or a defective product. The image processing sensor includes: an imaging unit configured to image the inspection target object; a display unit configured to display an image of the inspection target object acquired by the imaging unit; an operation unit configured to receive an instruction for registering the image displayed by the display unit; an image registering unit configured to register, on the basis of the instruction from the operation unit, a non-defective product image including the inspection target object that should be distinguished as the non-defective product displayed on the display unit or an image serving as a reference of pass/fail determination generated on the basis of the non-defective product image and a defective product image including the inspection target object that should be distinguished as the defective product displayed on the display unit; a threshold calculating unit configured to calculate a threshold with respect to a matching degree indicating a degree of feature matching of the non-defective product image and the defective product image registered by the image registering unit; and a display control unit configured to cause the display unit to display the non-defective product image and the defective product image as images used for the calculation of the threshold by the threshold calculating unit. The display control unit causes the display unit to display, on a first registration screen for registering one image of the non-defective product image and the defective product image, as a live image, the one image acquired by the imaging unit and, after receiving, with the operation unit, an instruction for registering the one image, causes the display unit to display, on a second registration screen for registering the other image, as the live image, the other image acquired by the imaging unit and, as a still image, the already registered one image. With the configuration explained above, it is possible to prevent defect detection accuracy from being easily affected by a background element and prevent deterioration in the defect detection accuracy. It is possible to simply and easily perform setting work necessary for the above.

Further, according to a third aspect of the present invention, in the image processing sensor, in addition to one of the configurations explained above, the display control unit may cause the display unit to display, on the second registration screen, the live image and the still image side by side on the same screen.

Furthermore, according to a fourth aspect of the present invention, in the image processing sensor, in addition to any one of the configurations explained above, timing when the display control unit transitions the first registration screen to the second registration screen may be set the same as timing when the display control unit registers, with the image registering unit, the one image as the sill image on the first registration screen.

Furthermore, according to a fifth aspect of the present invention, in the image processing sensor, in addition to any one of the configurations explained above, timing when the display control unit transitions the first registration screen to the second registration screen may be set different from timing when the display control unit registers, with the image registering unit, the one image as the sill image on the first registration screen.

Furthermore, according to a sixth aspect of the present invention, in the image processing sensor, in addition to any one of the configurations explained above, the image registering unit may register, on the basis of the instruction from the operation unit, as a background image, an image of a background from which a feature portion of the non-defective product in the inspection target object displayed on the display unit is removed.

Furthermore, according to a seventh aspect of the present invention, in the image processing sensor, in addition to any one of the configurations explained above, the threshold calculating unit may calculate the threshold on the basis of a first differential image calculated from the non-defective product image and the background image and a second differential image calculated from the defective product image and the background image.

Furthermore, according to an eighth aspect of the present invention, in the image processing sensor, in addition to any one of the configurations explained above, the display control unit may transition, on the basis of the instruction from the operation unit, the first registration screen and the second registration screen to a third registration screen for registering the background image.

Furthermore, according to a ninth aspect of the present invention, in the image processing sensor, in addition to any one of the configurations explained above, the display control unit may cause the display unit to display the background image as the live image on the third registration screen.

Furthermore, according to a tenth aspect of the present invention, in addition to anyone of the configurations explained above, the image processing sensor may further include a magnification adjusting unit configured to adjust magnification of the image displayed on the display unit. The display control unit may cause the display unit to display, on the first registration screen, the one image as the live image at the magnification set by the magnification adjusting unit and cause the display unit to display, on the second registration screen, the other image as the live image at the magnification used on the first registration screen.

Furthermore, according to an eleventh aspect of the present invention, in the image processing sensor, in addition to any one of the configurations explained above, the display control unit may be capable of displaying, on the display unit, the threshold calculated by the threshold calculating unit. The image processing sensor may further include a threshold adjusting unit configured to adjust the threshold displayed on the display unit.

Furthermore, according to a twelfth aspect of the present invention, in the image processing sensor, in addition to any one of the configurations explained above, the display control unit may cause, when causing the threshold adjusting unit to adjust the threshold, the display unit to display a matching degree of the defective product image with respect to the non-defective product image.

Furthermore, according to a thirteenth aspect of the present invention, in the image processing sensor, in addition to any one of the configurations explained above, the display control unit may cause, when causing the threshold adjusting unit to adjust the threshold, the display unit to display a matching degree of the non-defective product image as a fixed value.

Furthermore, according to a fourteenth aspect of the present invention, in the image processing sensor, in addition to any one of the configurations explained above, the display unit may be configured by an organic EL element.

Furthermore, according to a fifteenth aspect of the present invention, in any one of the configurations explained above, the image processing sensor may further include an operation/setting-mode switching unit configured to switch an operation mode for distinguishing pass/fail of the inspection target object with the pass-fail determining unit and a setting mode for calculating a threshold used in the operation mode. The display control unit may cause, in the setting mode and the operation mode, the display unit to display, in positions respectively corresponding to the setting mode and the operation mode, image display regions where the image is displayed.

Furthermore, according to a sixteenth aspect of the present invention, in the image processing sensor, in addition to any one of the configurations explained above, in a state in which the image processing sensor is switched to the operation mode by the operation/setting-mode switching unit, the image processing sensor may be capable of displaying, on the display unit, the threshold calculated by the threshold calculating unit and a matching degree.

Furthermore, according to a seventeenth aspect of the present invention, in the image processing sensor, in addition to any one of the configurations explained above, in a state in which the image processing sensor is switched to the operation mode by the operation/setting-mode switching unit, the display control unit may cause the display unit to display the live image of the inspection target object and the already registered still image on the same screen of the display unit.

Furthermore, according to an eighteenth aspect of the present invention, in the image processing sensor, in addition to any one of the configurations explained above, the display control unit may cause the display unit to display, in an image display region where the image is displayed, guide lines serving as indicators for positioning in placing the inspection target object in an imaging position.

Furthermore, according to a nineteenth aspect of the present invention, in the image processing sensor, in addition to any one of the configurations explained above, the display control unit may be capable of displaying, on the display unit, registration order information indicating registration order for performing image registration of the first image and the second image.

An image processing method according to a twentieth aspect of the present invention is an image processing method for performing predetermined image processing on an image of an inspection target object to detect that the inspection target object is a non-defective product or a defective product. The image processing method includes: a step of capturing, with an imaging unit, a non-defective product image including the inspection target object that should be distinguished as the non-defective product or an image serving as a reference of pass/fail determination generated on the basis of the non-defective product image, causing a display unit to display the non-defective product image or the image as a live image on a first registration screen, and urging registration of the non-defective product image or the image as a first image; and a step of, after receiving an instruction for registering the first image from an operation unit, causing the display unit to display the registered first image as a still image, on the other hand, imaging, with the imaging unit, a second image registration screen for registering a second image not including the target object that should be distinguished as the non-defective product, causing the display unit to display the second image registration screen as the live image side by side with the still image, and urging registration of the second image. Consequently, when an image that is not an image of the non-defective product is registered, by displaying the non-defective product image captured in advance side by side with the image as the still image, it is possible to perform the registration while clearly displaying a difference desired to be detected between the image and the non-defective product image. Portions without a difference in the non-defective product image and the image of the product that is not the non-defective product are disposed similarly. Consequently, it is possible to more clearly distinguish the difference.

Furthermore, an image processing program according to a twenty-first aspect of the present invention is an image processing program for performing predetermined image processing on an image of an inspection target object to detect that the inspection target object is a non-defective product or a defective product. The image processing program causes a computer to realize: a function of acquiring, with an imaging unit, a non-defective product image including the inspection target object that should be distinguished as the non-defective product or an image serving as a reference of pass/fail determination generated on the basis of the non-defective product image, causing a display unit to display the non-defective product image or the image as a live image on a first registration screen, and urging registration of the non-defective product image or the image as a first image; and a function of, after receiving an instruction for registering the first image from an operation unit, causing the display unit to display the registered first image as a still image, on the other hand, imaging, with the imaging unit, a second image registration screen for registering a second image not including the target object that should be distinguished as the non-defective product, causing the display unit to display the second image registration screen as the live image side by side with the still image, and urging registration of the second image. Consequently, when an image that is not an image of the non-defective product is registered, by displaying the non-defective product image captured in advance side by side with the image as the still image, it is possible to perform the registration while clearly displaying a difference desired to be detected between the image and the non-defective product image. Portions without a difference in the non-defective product image and the image of the product that is not the non-defective product are disposed similarly. Consequently, it is possible to more clearly distinguish the difference.

Furthermore, a computer-readable recording medium having a computer program recorded therein or a device having the computer program recorded therein according to a twenty-second aspect of the present invention stores the computer program. Examples of the recording medium include magnetic disks, optical disks, and magneto-optical disks such as a CD-ROM, a CD-R, a CD-RW, a flexible disk, a magnetic tape, an MO, a DVD-ROM, a DVD-RAM, a DVD-R, a DVD+R, a DVD-RW, a DVD+RW, a Blu-ray (registered trademark) disk, and a HD DVD, a semiconductor memory, and other media capable of storing computer programs. Examples of the computer program include, besides computer programs stored in the recording media and distributed, a computer program of a form distributed by download through a network line such as the Internet. Examples of the device having the computer program recorded therein include a general-purpose or dedicated device in which the computer program is implemented in a state in which the computer program is executable in a form of software, firmware, or the like. Furthermore, kinds of processing and functions included in the computer program may be executed by program software executable by a computer. Processing of units may be realized by hardware such as a predetermined gate array (FPGA or ASIC) or in a form in which the program software and a partial hardware module for realizing a part of elements of the hardware are mixed.

BRIEF DESCRIPTION OF THE DRAWINGS

FIG. 20 is an image diagram showing a background image.

FIG. 21 is an image diagram showing a state in which an evaluation region is set with respect to the background image shown in FIG. 20.

FIG. 22 is a table showing an example of matching degree threshold setting.

FIG. 37B is a flowchart for explaining the example of the screen transition of the operation mode.

FIG. 42 is a schematic diagram showing a state in which image data is averaged and compressed.

FIG. 43 is a schematic diagram showing a state in which image data is curtailed and compressed.

FIG. 44A is a flowchart for explaining a procedure of setting and operation of two-point registration of a non-defective product image and a background image including resolution reduction processing, FIG. 44B is an image diagram showing an example of the non-defective product image, FIG. 44C is an image diagram showing an example of the background image, FIG. 44D is an image diagram showing an example of a compressed non-defective product image, FIG. 44E is an image diagram showing an example of a compressed background image, and FIG. 44F is an image diagram showing an example of a compressed non-defective product-background differential image.

FIG. 45A is a flowchart for explaining a procedure of setting and operation of two-point registration of a non-defective product image and a background image including the resolution reduction processing, FIG. 45B is an image diagram showing an example of the non-defective product image, FIG. 45C is an image diagram showing an example of the background image, FIG. 45D is an image diagram showing an example of a non-defective product-background differential image, and FIG. 45E is an image diagram showing an example of a compressed non-defective product-background differential image.

FIG. 46A is a flowchart for explaining a procedure of setting and operation of three-point registration of a non-defective product image, a defective product image, and a background image including the resolution reduction processing, FIG. 46B is an image diagram showing an example of the non-defective product image, FIG. 46C is an image diagram showing an example of the defective product image, FIG. 46D is an image diagram showing an example of the background image, FIG. 46E is an image diagram showing an example of a compressed non-defective product image, FIG. 46F is an image diagram showing an example of a compressed defective product image, FIG. 46G is an image diagram showing an example of a compressed background image, FIG. 46H is an image diagram showing an example of a compressed non-defective product-background differential image, and FIG. 46I is an image diagram showing an example of a compressed defective product-background differential image.

FIG. 47A is a flowchart for explaining a procedure of setting and operation of three-point registration of a non-defective product image, a defective product image, and a background image including the resolution reduction processing, FIG. 47B is an image diagram showing an example of the non-defective product image, FIG. 47C is an image diagram showing an example of the defective product image, FIG. 47D is an image diagram showing an example of the background image, FIG. 47E is an image diagram showing an example of a non-defective product-background differential image, FIG. 47F is an image diagram showing an example of a defective product-background differential image, FIG. 47G is an image diagram showing an example of a compressed non-defective product-background differential image, and FIG. 47H is an image diagram showing an example of a compressed defective product-background differential image.

FIG. 48A is a flowchart for explaining a procedure of one-point registration for registering a background image including the resolution reduction processing, FIG. 48B is an image diagram showing the background image, and FIG. 48C is an image diagram showing a compressed background image.

FIG. 51A is a flowchart for explaining a series of image processing before replacement of an image processing algorithm, FIG. 51B is a flowchart for explaining a series of image processing after replacement of a part of the image processing algorithm from FIG. 51A, FIG. 51C is an image diagram showing a non-defective product image, FIG. 51D is an image diagram showing a defective product image, FIG. 51E is an image diagram showing a background image, FIG. 51F is an image diagram showing an evaluation image, FIG. 51G is an image diagram showing an image of work, FIG. 51H is an image diagram showing an image of the work cut out from the evaluation image shown in FIG. 51F, FIG. 51I is an image diagram showing an image of a region of the work cut out by differential processing of the evaluation image shown in FIG. 51F and the background image shown in FIG. 51E, and FIG. 51J is an image diagram showing a work region cut out from the evaluation image shown in FIG. 51H.

FIG. 53A is a schematic diagram showing Sobel X of a Sobel filter, FIG. 53B is a schematic diagram showing Sobel Y, and FIG. 53C is a schematic diagram showing X and Y components of an edge applied with Sobel X and Sobel Y.

FIG. 54A is a schematic diagram showing Roberts X, FIG. 54B is a schematic diagram showing Roberts Y, and FIG. 54C is a schematic diagram showing X and Y components of an edge applied with Roberts X and Roberts Y.

FIG. 55 is an image diagram showing a state in which non-defective work and defective work flow on a manufacturing line.

DESCRIPTION OF EMBODIMENTS

Figure 1A:
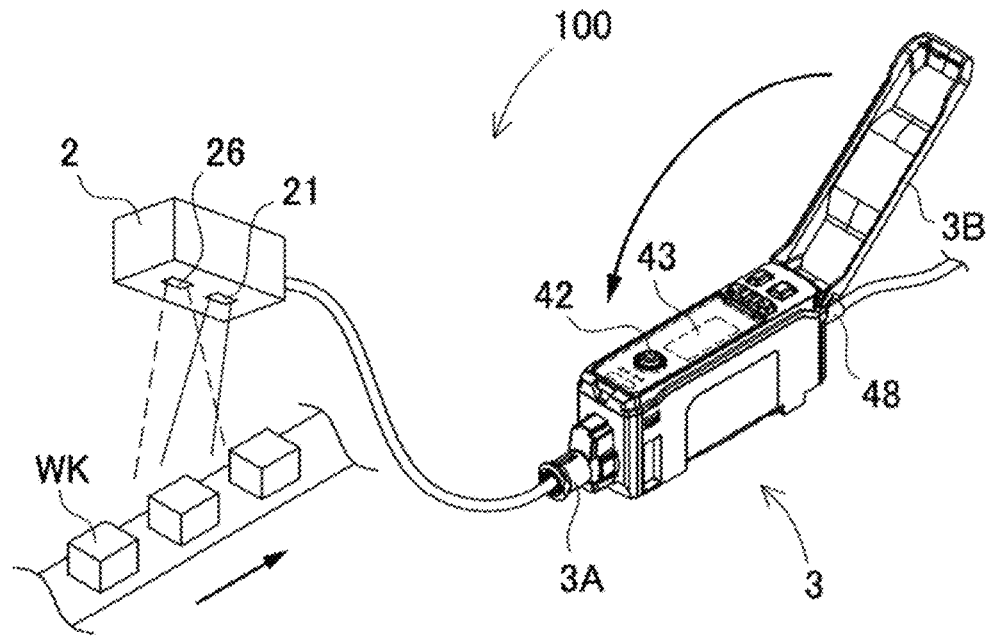
FIG. 1A is a schematic diagram showing an image processing sensor according to a first embodiment of the present invention.

Embodiments of the present invention are explained below with reference to the drawings. However, the embodiments explained below are illustrations for embodying the technical idea of the present invention. The present invention is not limited to the embodiments explained below. This specification does not limit members explained in claims to members explained in the embodiments. Dimensions, materials, shapes, relative dispositions, and the like of constituent components described in the embodiments are not meant to limit the scope of the present invention only thereto unless specifically described otherwise and are only mere explanation examples. Note that sizes, positional relations, and the like of the members shown in the drawings are sometimes exaggerated to clarify explanation. Further, in the following explanation, the same names and the same reference numerals and signs indicate the same or homogenous members. Detailed explanation of the members is omitted as appropriate. Further, as elements configuring the present invention, a plurality of elements may be configured by the same member and one member may be used as the plurality of elements. Conversely, a function of one member can be shared and realized by a plurality of members.

First Embodiment

Figure 1B:
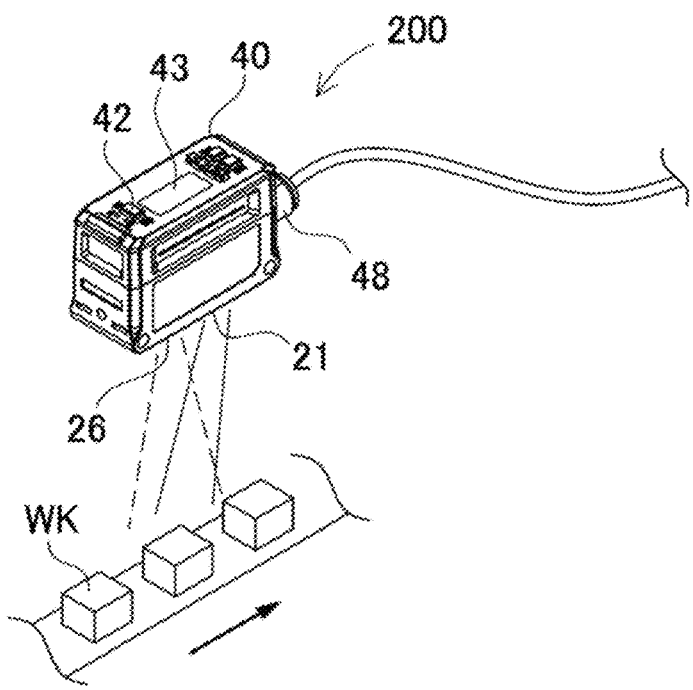
FIG. 1B is a schematic diagram showing an image processing sensor according to a second embodiment of the present invention.

An image processing sensor 100 according to a first embodiment of the present invention is shown in FIG. 1A. An image processing sensor 200 according to a second embodiment is shown in FIG. 1B. The image processing sensors capture an image of an inspection target object (hereinafter referred to as "work (WK)") as well and performs image processing on the image to determine or detect that the inspection target object is a non-defective product or a defective product. The image processing sensors can perform, by outputting determination result to the outside, necessary post processing such as confirmation of the non-defective product or removal of the defective product on the basis of an output of an inspection result.

The image processing sensors can be switched to an operation mode for performing the determination of the non-defective product and the defective product and a setting mode for performing setting. In the setting mode, a user can register a model image such as a non-defective product image obtained by imaging the non-defective product. A matching degree threshold serving as a reference in the determination of the non-defective product and the defective produce is set on the basis of the registered model image (details are explained below). Such setting work performed prior to operation is called teaching or the like.

Figure 2A:
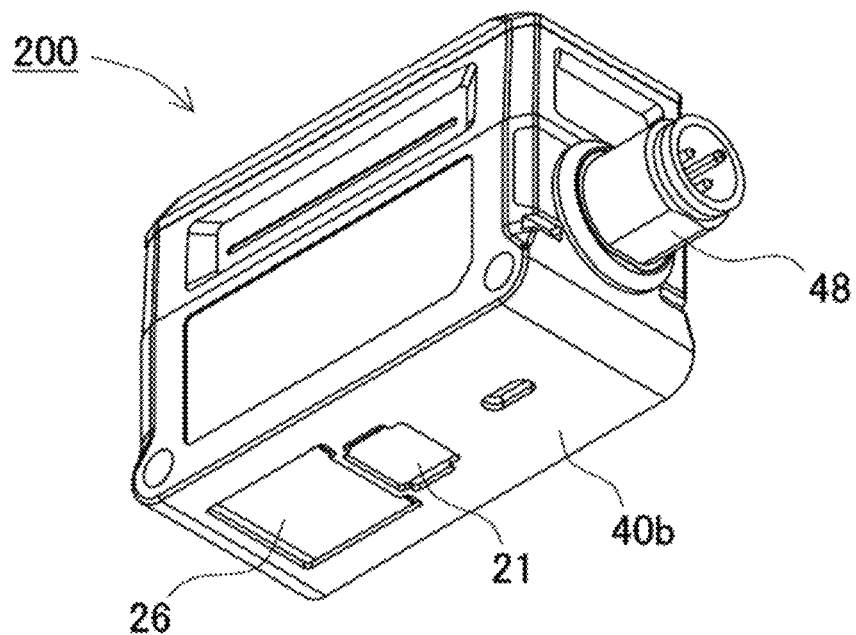
FIG. 2A is a perspective view of the image processing sensor shown in FIG. 1B viewed from a rear obliquely downward direction and FIG. 2B is a vertical sectional view of the image processing sensor.
Figure 2B:
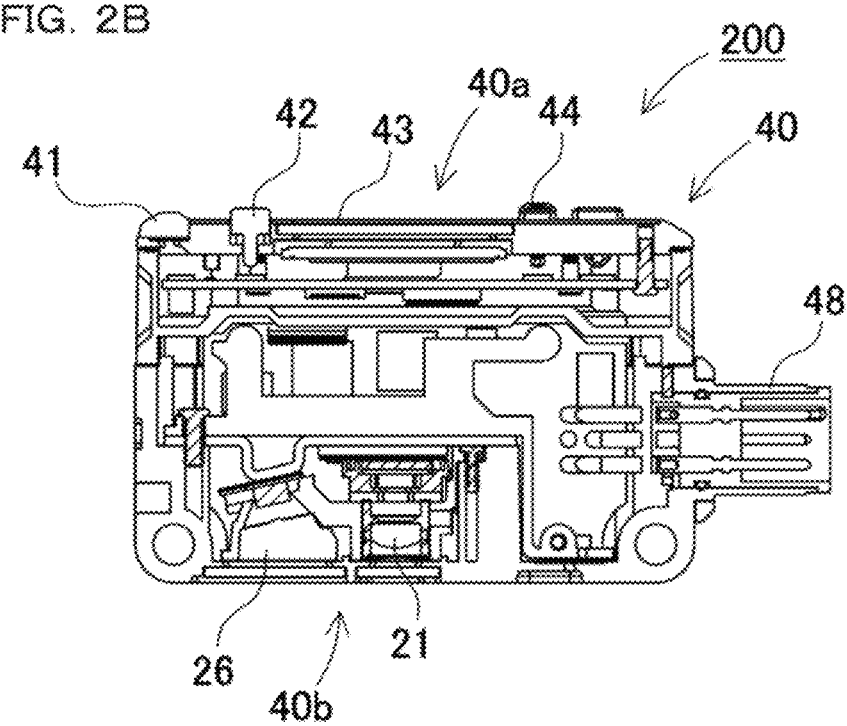

FIG. 1A shows the image processing sensor 100 of a separated type in which a head unit 2 and a controller unit 3 are separated. FIG. 1B shows the image processing sensor 200 of an integrated type in which a head unit and a controller unit are integrated. A perspective view of the image processing sensor 200 shown in FIG. 1B viewed from a rear obliquely downward direction is shown in FIG. 2A. A vertical sectional view of the image processing sensor 200 is shown in FIG. 2B.

The head unit 2 shown in FIG. 1A includes an imaging unit 21 such as a camera and an illuminating unit 26. On the other hand, the controller unit 3 is a member for performing image processing on an image captured by the head unit 2 and is called amplifier unit as well. The head unit 2 and the controller unit 3 can be respectively housed in different casings (housings) as shown in FIG. 1A or can be housed in a common casing 40 as shown in FIG. 1B. The illuminating unit of the head unit can be provided separately from the camera. In the following explanation, mainly as the exterior of the image processing sensor, the casing 40 in which the head unit and the controller unit shown in FIG. 1B are integrated is explained. However, the controller unit 3 shown in FIG. 1A is basically the same.

Note that even the controller unit alone functions as an image processing sensor. In this case, an image input unit for taking in an image captured by an external device such as the head unit functions as an image acquiring unit.

(Casing 40)

The casing 40 of the image processing sensor is configured in a hexahedron shape configured from upper and lower surfaces, left and right surfaces, and front and rear surfaces. Among the surfaces, the upper surface is set as a first principal plane and the lower surface opposed to the upper surface is set as a second principal plane. As shown in FIGS. 2A and 2B, a display unit 43 and an operation unit 51 are provided on the second principal plane on the lower surface side. On the other hand, the display unit 43 and the operation unit 51 are provided on the first principal plane on the upper surface side. In this way, the second principal plane on the bottom surface side is set as an imaging surface 40b and the first principal plane on the upper surface side is set as a display surface 40a. Consequently, it is possible to display an image captured by the imaging surface 40b on the display surface 40a and match a disposition posture and a layout of the image processing sensor 200.

The imaging unit 21 is a member for capturing an image of work and is configured by a camera and the like. As the camera, an imaging element such as a CMOS or a CCD can be used. In this case, an image captured by the imaging unit 21 is an optical image. Note that, when an imaging unit capable of measuring height information is used, a height image obtained by converting height information into luminance can also be used such that an image having the height information can be treated in the same manner as a two-dimensional optical image.

The illuminating unit 26 is a member for irradiating illumination light when an image of work is captured by the imaging unit 21. As a light source of the illumination light, an LED, an organic EL, an incandescent lamp, a halogen lamp, and the like can be used. As the illumination light, various colors can be used. For example, when conveying speed of a line is high, an exposure time that can be consumed to capture one optical image decreases. Therefore, it is desirable to adopt a light source having a large light amount such that sufficient brightness can be secured in a short time. Form such a viewpoint, a red color or the like with which a light source is inexpensive and a light amount can be easily obtained can be suitably used. White light and infrared light may be used. Alternatively, depending on a color and a material of distinction target work, an illumination color that is easily determined is sometimes present. In this case, the illumination color can also be included in parameters of brightness conditions.

As shown in the sectional view of FIG. 2B, the imaging unit 21 is disposed in parallel to the imaging surface 40b and configured such that the optical axis of the imaging element is substantially orthogonal to the imaging surface 40b. Consequently, it is possible to capture an orthogonal image of an inspection target object present in an imaging position below the image processing sensor. On the other hand, a light projection surface of the illuminating unit 26 is slightly inclined with respect to the imaging surface 40b. Since the optical axis of the illumination light is set oblique to the optical axis of the imaging element, it is possible to capture an image with a natural shadow. Note that, in the example shown in FIG. 2A, one light source of the illumination light is provided. However, a plurality of light sources can also be provided. For example, illumination light sources are provided at four corners of the imaging surface to surround the imaging unit. Consequently, it is possible to obtain an image with a less shadow.

(Display Surface 40a)

Figure 3A:
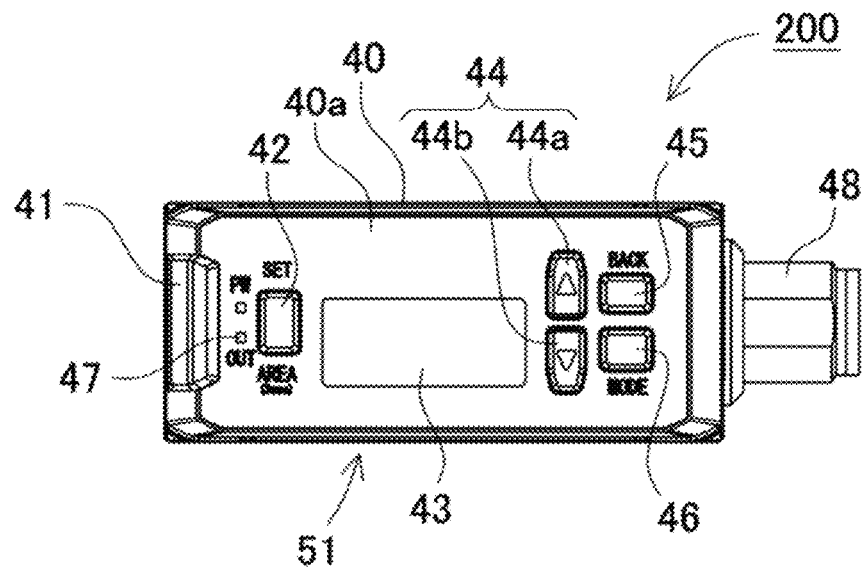
FIG. 3A is a schematic diagram showing a display surface of the image processing sensor according to the second embodiment.

An example of the display surface 40a is shown in the schematic diagram of FIG. 3A. The display surface 40a is formed in a rectangular shape long in one direction. As shown in the figure, the operation unit 51 is provided on the display surface 40a of the image processing sensor 200 in addition to the display unit 43. The operation unit 51 includes a SET key 42 equivalent to a determination key for instructing determination such as an image registration button, up/down keys 44 equivalent to an increase/decrease adjusting unit 51h (FIG. 5 referred to below), a BACK key 45 equivalent to a cancellation instructing unit, and a MODE key 46 equivalent to an operation/setting-mode switching unit 51d (FIG. 5 referred to below) (details are explained below). Further, a display lamp is provided on the display surface 40*a*. The display lamp includes a determination-result display lamp 41 and an output-state display lamp 47.

(Display Unit 43)

The display unit 43 is a member for displaying an image of work captured by the imaging unit 21. As the display unit 43, a display of organic EL, liquid crystal, or the like can be used.

(Increase/Decrease Adjusting Unit 51*h*)

The increase/decrease adjusting unit 51*h* is configured by a pair of members, that is, a switch on an up-side and a switch on a down-side. The increase/decrease adjusting unit 51*h* is used to, for example, change display magnification of an image displayed on the display unit 43. The image displayed by the display unit 43 is, for example, a first image such as a non-defective product image, a second image such as a defective product image, and a third image such as a background image. In particular, the display magnification is adjusted by the increase/decrease adjusting unit 51*h* in order to enlarge and display the non-defective product image and non-defective product candidate images. The matching degree threshold can also be adjusted by the same increase/decrease adjusting unit 51*h* (details of these kinds of adjustment work are explained below). In this example, it is possible to give an instruction such that, when the switch on the up-side is operated, the magnification of the first image and the matching degree threshold increase and, when the switch on the down-side is operated, the magnification of the first image and the matching degree threshold decrease. In this way, the increase/decrease adjusting unit 51*h* enables different kinds of operation, that is, an adjusting function for image display magnification and an adjusting function for the matching degree threshold. The common increase/decrease adjusting unit 51*h* is used for adjustment of different values to reduce the number of operation buttons that should be provided in the display unit, avoid an increase in the size of the display unit, and avoid complication of operation due to an increase in the operation buttons. Consequently, simplification of a configuration, improvement of operability, a reduction in cost, and the like are achieved.

(Switching of the Functions of the Increase/Decrease Adjusting Unit)

The switching of the functions of the increase/decrease adjusting unit may be performed after the functions of the increase/decrease adjusting unit are selected. However, in this case, before the increase/decrease adjusting unit is operated, operation for selecting and switching the functions of the increase/decrease adjusting unit is essential. The user is forced to perform complicated operation. Therefore, the function switching is configured to be automatically executed such that, according to operation modes currently being selected, the functions of the increase/decrease adjusting unit change to functions suitable for the operation modes. Consequently, it is possible to eliminate the need for the operation of the function switching of the increase/decrease adjusting unit. For example, in a state in which the setting mode is selected by the operation/setting-mode switching unit 51*d*, a function of changing the image display magnification is allocated to the increase/decrease adjusting unit 51*h*. On the other hand, in a state in which the operation mode is selected by the operation/setting-mode switching unit 51*d*, a function of adjusting the matching degree threshold is allocated to the increase/decrease adjusting unit 51*h*. In this way, on a screen that needs to be operated, an appropriate function is automatically allocated to the increase/decrease adjusting unit 51*h*, to which a plurality of functions are allocated, without selecting any one of the functions in advance. It is possible to improve operability of the user.

Note that the function allocation for each of the operation modes is an example. For example, in the setting mode, when the adjustment of the image display magnification and the matching degree threshold is performed, in a state in which a screen on which the adjustment of the display magnification is possible (a magnification adjustment mode) and a screen on which the adjustment of the matching degree threshold is possible (a threshold adjustment mode) are displayed, the respective functions may be selected with respect to the increase/decrease adjusting unit.

Figure 3B:
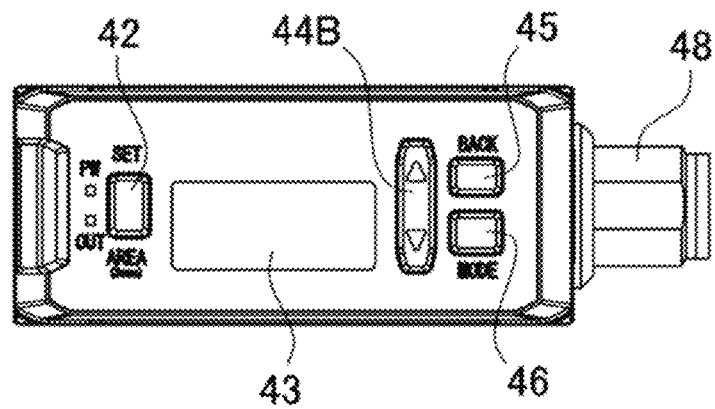
FIG. 3B is a schematic diagram showing a display surface of an image processing sensor according to a modification.

The increase/decrease adjusting unit 51*h* is an increase/decrease button. A pair of up/down keys 44 is equivalent to the increase/decrease adjusting unit 51*h*. The up/down keys 44 include a ↑ key 44*a*, which is a switch on an up-side, and a ↓ key 44*b*, which is a switch on a down-side. The up/down keys 44 are used for adjustment of an increase and a decrease, up and down movements, and the like. Note that, in the example shown in FIG. 3A, the up/down keys 44 are configured by separate keys, that is, the ↑ key 44*a* and the ↓ key 44*b*. However, the present invention is not limited to this configuration. The up/down keys 44 can be integrated. The increase and the decrease can be performed by one up/down key. Such an example is shown in FIG. 3B as a modification. An up/down key 44B shown in the figure is configured in a tiltable seesaw type. It is possible to instruct an increase by tilting the up/down key 44B upward and instruct a decrease by tilting the up/down key 44B downward.

The up/down keys 44 are vertically disposed side by side in this way. Therefore, the user can sensuously operate the up/down keys 44. That is, the user can increase a value by pressing the ↑ key 44*a* disposed in an upper part and reduce the value by pressing the ↓ key 44*b* disposed in a lower part. Therefore, the user can sensuously operate the keys. It is possible to reduce likelihood of erroneous operation. In general, the image processing sensor includes a large number of components compared with a photoelectric sensor. A casing tends to be thick. Therefore, even if the ↑ key 44*a* and the ↓ key 44*b* are vertically arranged in a longitudinally long shape, it is possible to secure width enough for disposing the keys without increasing the casing in size. It is possible to configure the exterior of the up/down keys 44 to match the shape of the up/down keys 44 with the function of the up/down keys 44.

When the display unit 43 having a rectangular shape is disposed on the surface 40*a* having a rectangular shape extending in one direction, it is reasonable in terms of space efficiency to dispose the display unit 43 to match the longitudinal direction of the display unit 43 with the longitudinal direction of the display surface 40*a*. In this case, the up/down keys 44 are desirably disposed on a side surface in the longitudinal direction of the display unit 43. When the up/down keys 44 are disposed in upper and lower parts of the display unit 43, the thickness of the display surface 40*a* increases, leading to an increase in the size of the casing of the image processing sensor. Therefore, the display unit 43 and the up/down keys 44 are disposed side by side along the longitudinal direction of the display surface 40*a*. This can contribute to a decrease in the size of the image processing sensor.

Further, the up/down keys 44 are desirably disposed on the opposite sides across the display unit 43 rather than being collectively disposed on the same side with respect to the display unit 43 together with determination buttons and the like such as the SET key 42. Consequently, it is possible to reduce, by physically separating the up/down keys 44 and the determination key, a risk of erroneous operation in which, after the display magnification and the matching degree threshold are increased or reduced, in operation for sending an instruction for determination from the SET key 42, the SET key 42 is touched by mistake when the up/down keys 44 are operated halfway in the increase or the reduction and an unintended instruction of determination is performed.

Note that the up/down keys 44 are not always limited to be vertically disposed side by side. For example, as shown in a modification in FIG. 3C, up/down keys 44C may be horizontally disposed side by side. In particular, in the conventional photoelectric sensor, up/down keys are configured by a "<" key and a ">" key and horizontally disposed side by side in order to achieve a reduction in thickness. Therefore, in the image processing sensor, the up/down buttons are disposed according to the disposition example in the photoelectric sensor. Consequently, it is easy to provide an operation feeling same as the operation feeling of the photoelectric sensor. It is easy even for a user of the photoelectric sensor to introduce and operate the image processing sensor without discomfort.

Figure 3C:
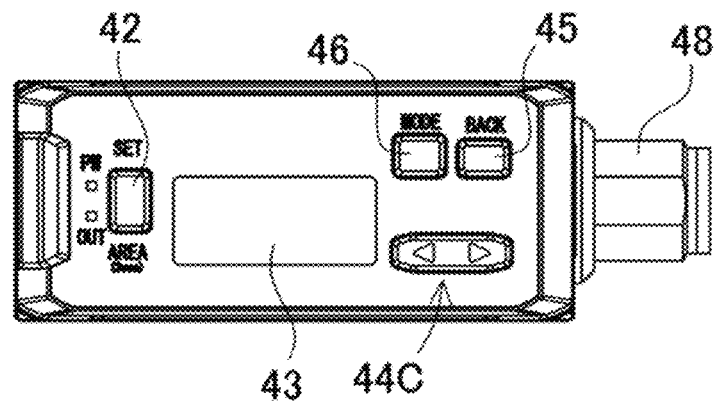
FIG. 3C is a schematic diagram showing a display surface of an image processing sensor according to another modification.

In the examples shown in FIGS. 3A to 3C, the up/down keys 44, the BACK key 45, the MODE key 46, and the like are disposed on the right side of the display unit 43. Since the keys requiring delicate operation are disposed on the right side, it is possible to allow users considered to be often right-handed to easily operate the keys with the right hands.

Further, the shapes of the keys are desirably differentiated from one another. Consequently, the user can distinguish types of the keys with a touch. Therefore, even when it is difficult to directly view the keys disposed in a dark place or in deep positions, it is possible to operate the keys with a tactile sense. For example, in the example shown in FIG. 3A, in the up/down keys 44, the distal end on the upper side of the ↑ key 44a is tapered and the distal end on the lower side of the ↓ key 44b is tapered. The BACK key 45 and the MODE key 46 are horizontally long and vertically disposed side by side. On the other hand, the SET key 42 is formed to be longitudinally long. In particular, by differentiating the shapes of the determination key from the shapes of the BACK key 45 and the MODE key 46, it is possible to cause the user to surely perform work for pressing the determination key after the adjustment in the increase/decrease adjusting unit 51h.

Furthermore, in the increase/decrease adjusting unit 51h, marks such as Δ and ∇ are displayed on key tops by stamping, printing, or the like. Consequently, it is possible to cause the user to visually grasp that the keys are keys for performing an increase and a decrease.

(Increase/Decrease Icon 61)

Figure 7:
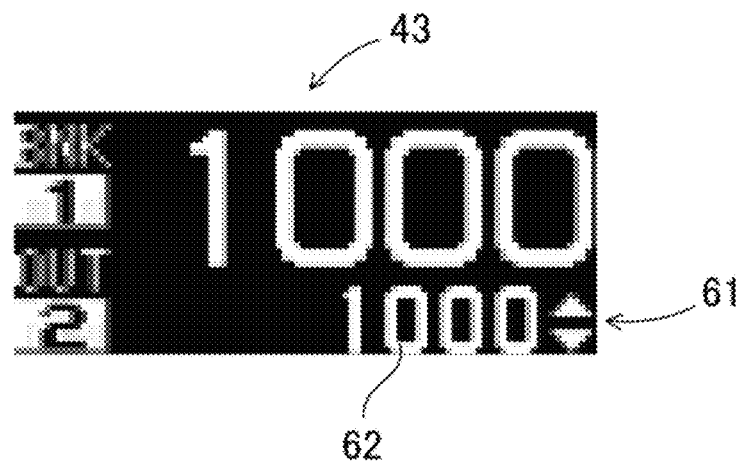
FIG. 7 is an image diagram showing an operation screen of the display unit.
Figure 8:
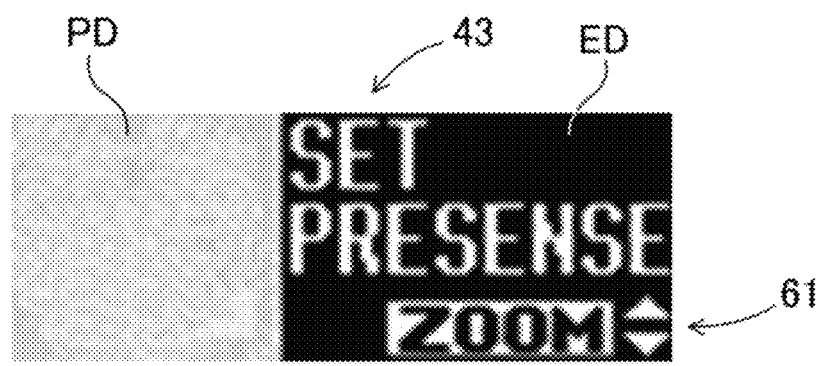
FIG. 8 is an image diagram showing an example of a first registration screen during the two-point registration.
Figure 9:
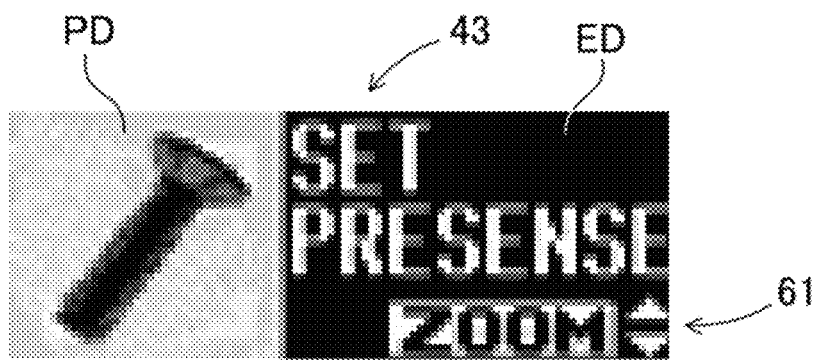
FIG. 9 is an image diagram showing a state in which a non-defective product image is displayed in FIG. 8.

As shown in FIGS. 7 and 8 and the like referred to below, a display form of an increase/decrease icon 61 displayed on the display unit 43 can be changed according to items adjustable by the increase/decrease adjusting unit 51h. For example, as shown in FIG. 7, on a screen on which the matching degree threshold can be changed, the increase/decrease icon 61 indicates that it is possible to display marks such as Δ and ∇ beside a numerical value together with a matching-degree-threshold display region 62 in which a numerical value of the matching degree threshold currently being set is displayed and increase or reduce the displayed value. On the other hand, as shown in FIGS. 8 and 9, on a screen on which an image is displayed in an image display region PD, characters "ZOOM" and marks such as Δ and ∇ beside the characters are displayed as the increase/decrease icon 61 to indicate that it is possible to perform zoom-in and zoom-out with the increase/decrease adjusting unit 51h.

(Reversal Display Function)

Figure 3D:
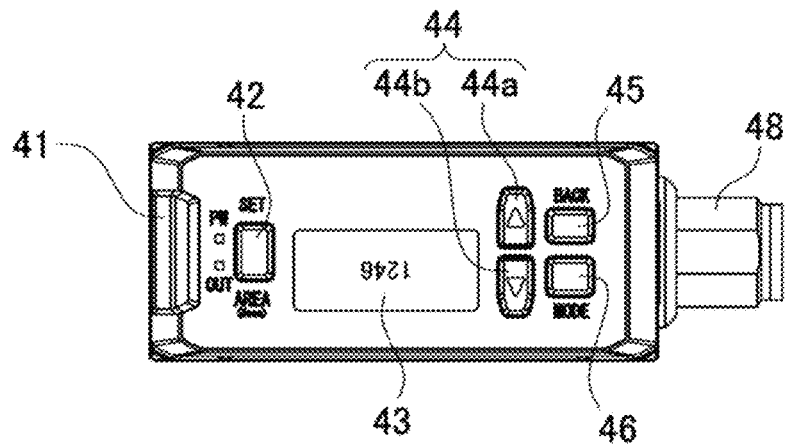
FIG. 3D is a schematic diagram showing an image processing sensor in which a display unit is reversely displayed.

Note that the display of an image, a numerical value, and the like on the display unit 43 can be reversed as shown in FIG. 3D. Consequently, while flexibly changing a posture of the image processing sensor during incorporation in a production line according to a draw-out direction or the like of cables, it is possible to change the display itself on the display unit 43 according to a direction visually recognized by the user and avoid a situation in which the display is reversed upside down and hard to be distinguished. Such a change in the display form on the display unit 43 can be performed by a display control unit 58f explained below.

(Reversal Display Associated Increase/Decrease Function)

In this case, when the display of the display unit 43 is reversed, it is possible to interchange the functions of the up/down keys 44 of the increase/decrease adjusting unit 51h and change the operation of the increase and reduction to match the operation with a numerical value and the top and the bottom of an image displayed on the display unit 43. Consequently, it is possible avoid an environment in which the increase and the reduction have to be performed oppositely to arrows and the top and the bottom and erroneous operation easily occurs when the display is opposite as in the past. It is possible to avoid a setting mistake by performing input operation, which is sensuously easy to understand, for increasing a numerical value and an image in an upward direction and reducing the numerical value and the image in a downward direction.

(Determination-Result Display Lamp 41)

The determination-result display lamp 41 indicates, with lighting, a result determined in the operation mode. For example, when a non-defective product is detected, the determination-result display lamp 41 is lit in blue. When a defective product is detected, the determination-result display lamp 41 is lit in red. As such an output display lamp, a light emitting body such as an LED can be used. A light emission color desirably can be changed. For example, a red LED and a blue LED can be provided. A multicolor LED with variable colors can be used.

The output-state display lamp 47 is a member for displaying a state of an output. An LED and the like can be used as the output/state display lamp 47. Details of the other members are explained below.

Note that the operation unit 51 and the display lamps can also be virtually configured on a display besides being configured by physical buttons and lamps. For example, it is also possible to configure the display surface with a touch panel, display the display unit, the operation unit, and the display lamps as images on the display surface, and cause the display unit, the operation unit, and the display lamps to function as virtual buttons and lamps.

A connector unit 48, to which a cable is connected, is disposed in one of the front surface or the rear surface among the surfaces configuring the hexahedron shape of the casing 40. In the example shown in FIGS. 2A and 2B and the like, the connector unit 48 having a cylindrical shape is provided on the rear surface side (in the figures, the right side). Note that, as shown in FIG. 1A, in the case of the image processing sensor of the separated type in which the head unit 2 and the controller unit 3 are separated, a head-unit-side connector 3A for connecting the head unit 2 is provided on the front surface side.

(Cover Unit 3B)

A cover unit 3B may be provided on the display surface 40a. By providing the cover unit 3B, it is possible to avoid a situation in which a hand or the like of the user touches the operation unit 51 by mistake and, for example, setting of the matching degree threshold is unintentionally changed. In the example shown in FIG. 1A, the cover unit 3B covering the display unit 43 is provided to be capable of opening and closing. In this example, the cover unit 3B is turnably coupled to one end in the longitudinal direction of the display surface 40a in a pivot type to be capable of opening and closing. By configuring the cover unit 3B with a member having light transmissivity, it is possible to visually recognize the display unit 43 even in a state in which the cover unit 3B is closed. The cover unit 3B can be made of resin or the like.

A cover unit does not have to be provided. In FIG. 1B, an example of an image processing sensor in which a cover unit is not provided is shown. A key lock function may be imparted to the operation unit when the cover unit is not provided. When the key lock function is actuated, even if the user touches the operation unit, the operation unit does not respond. It is possible to avoid, for example, an unintended change of setting. When performing operation, the user performs specific release operation to release the key lock function. Such release operation can be, for example, long-press of a specific key.

(Hardware Block Diagram)

Figure 4:
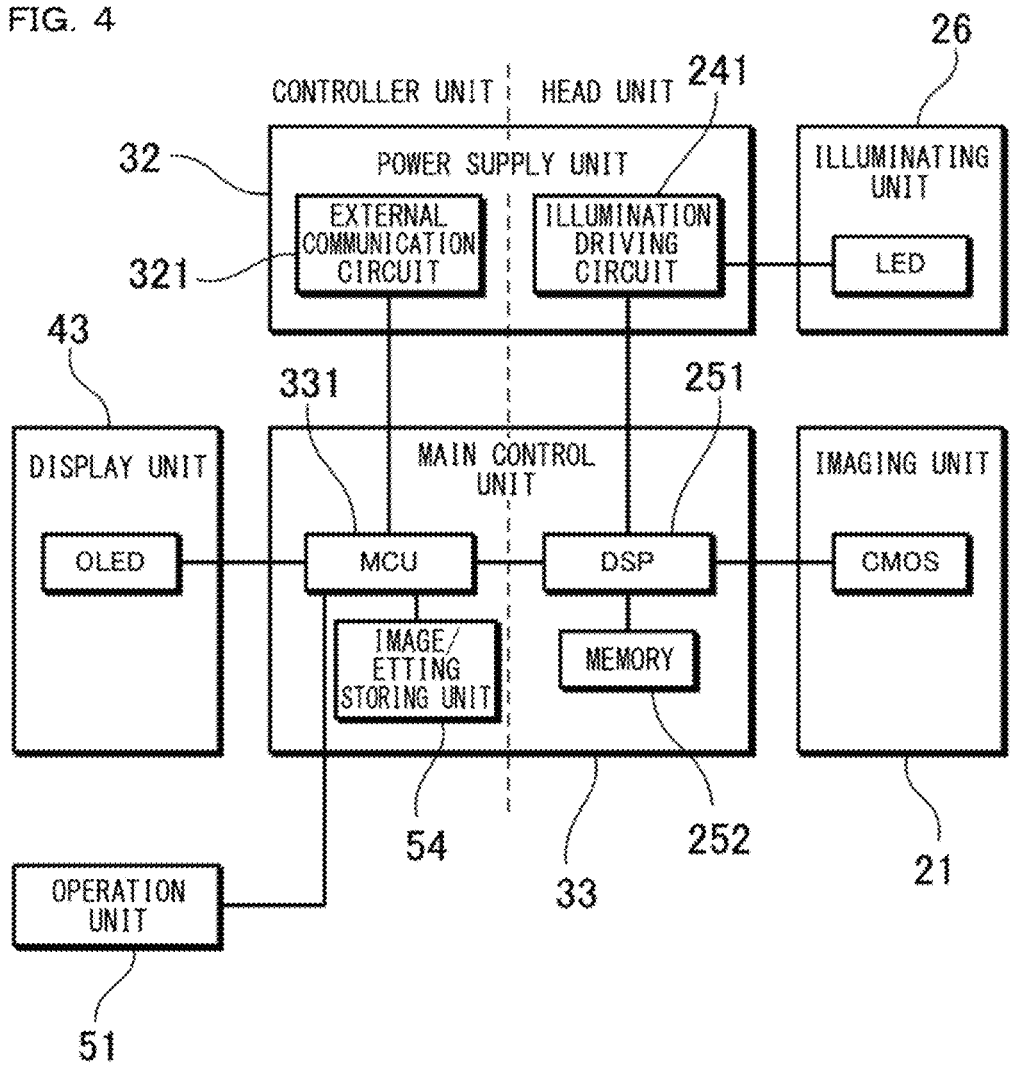
FIG. 4 is a block diagram of an image processing sensor.

A block diagram of the image processing sensor is shown in FIG. 4. As shown in the figure, a hardware configuration of the image processing sensor mainly includes the imaging unit 21, the illuminating unit 26, a power supply unit 32, a main control unit 33, the display unit 43, and the operation unit 51. Note that the figure shows a block diagram of the image processing sensor of the integrated type shown in FIG. 1B. In the case of the image processing sensor of the separated type shown in FIG. 1A, the right side indicated by a broken line in FIG. 4 is equivalent to the head unit 2 and the left side is equivalent to the controller unit 3.

The power supply unit 32 includes a voltage conversion circuit for supplying driving power to the units. In an example shown in FIG. 4, the power supply unit 32 includes an illumination driving circuit 241 that supplies electric power to a light source of the illuminating unit 26 and performs control of ON/OFF of lighting and a light amount of the illuminating unit 26. When the light source of the illuminating unit 26 is an LED, the illumination driving circuit 241 is an LED driver circuit. An external communication circuit 321 for performing data communication with the outside may be provided in the power supply unit 32. The external communication circuit 321 functions as, for example, a determination-result output unit that outputs, for example, a determination result of a non-defective product and a defective product to the outside.

The main control unit 33 is a member for performing driving control of the imaging unit 21, image processing of an image obtained by the imaging unit 21, pass/fail determination, and the like. In the example shown in FIG. 4, the main control unit 33 is configured by a DSP 251, a MCU 331, a memory 252, and the like. The main control unit 33 includes an image/setting storing unit 54 for retaining a model image and setting. The image/setting storing unit 54 is configured by a storage such as a semiconductor memory or a hard disk.

The operation unit 51 is a member for the user to perform various kinds of operation on the image processing sensor. Specifically, various buttons provided on the display surface 40a of the casing 40 correspond to the operation unit 51. The function of the operation unit can be integrated by the display unit by configuring the display unit with a touch panel.

(Functional Block Diagram)

Figure 5:
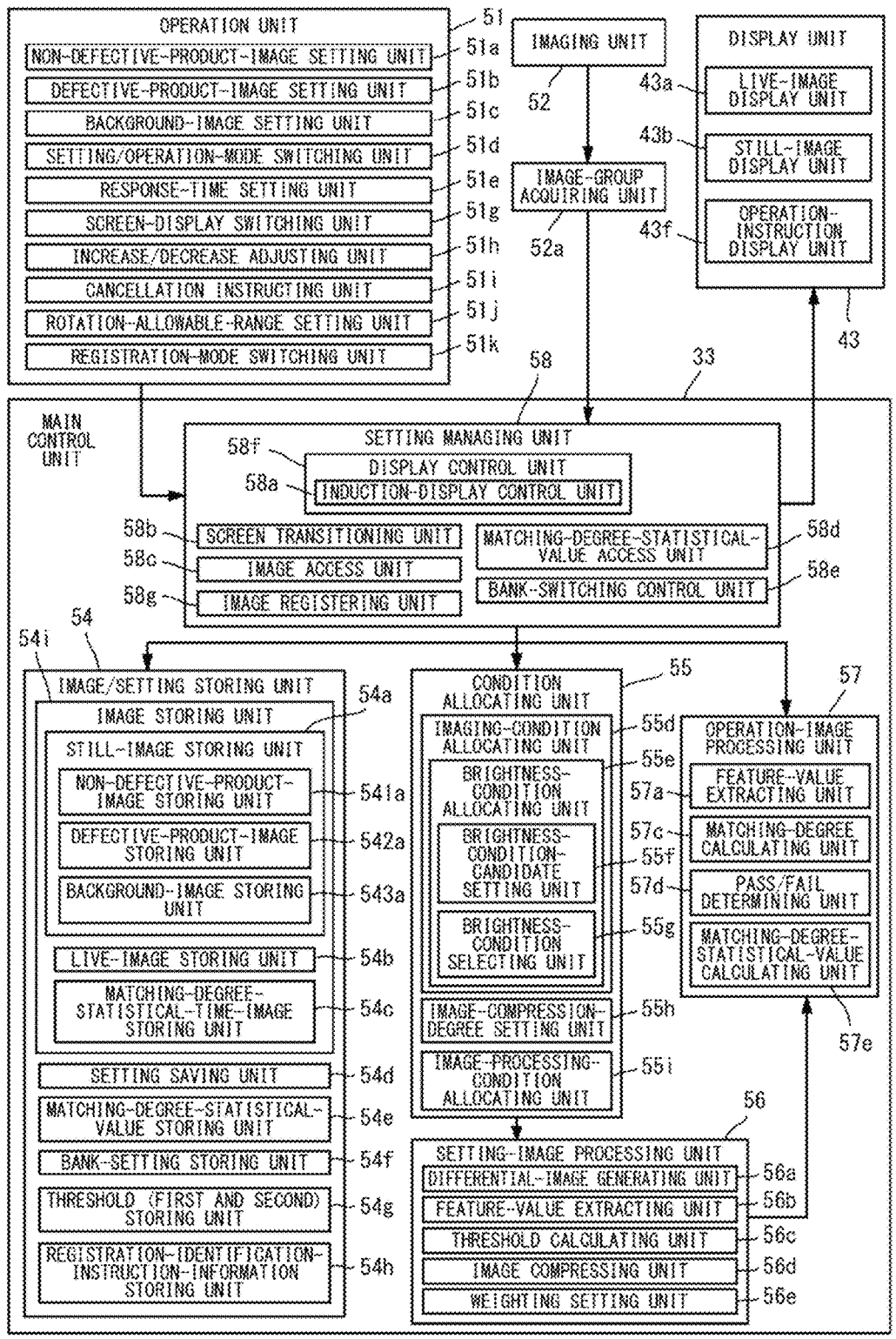
FIG. 5 is a block diagram showing functions of the image processing sensor.

Further, a detailed block diagram grasped in terms of the functions of the image processing sensor is shown in FIG. 5. As shown in the figure, the image processing sensor includes the operation unit 51, the imaging unit 21, the display unit 43, and the main control unit 33. The operation unit 51 is a member for receiving an operation instruction from the user and communicating the operation instruction to the main control unit 33. The imaging unit 52 is a member for capturing an image and passing the captured image to amain control unit 61. The display unit 43 is a member for displaying a current sensor state and displaying content of an instruction to the user.

The main control unit 33 includes a setting managing unit 58, the image/setting storing unit 54, a condition allocating unit 55, a setting-image processing unit 56, and an operation-image processing unit 57. The setting managing unit 58 is a member for controlling the image/setting storing unit 54, the condition allocating unit 55, the setting-image processing unit 56, and the operation-image processing unit 57 on the basis of information inputs from the operation unit 51 and the imaging unit 52 and performing display on the display unit 43. The image/setting storing unit 54 is a member for storing an image and setting. The condition allocating unit 55 is a member for changing a registered condition pattern and deducing an optimum registration condition. The setting-image processing unit 56 is a member for performing image processing registration on the basis of an image to make it possible to perform an evaluation of a target image. The operation-image processing unit 57 is a member for performing the evaluation of the target image and calculating a matching degree. Roles of the blocks are explained below.

(Operation Unit 51)

The operation unit 51 is a member for receiving an operation instruction from the user and communicating the operation instruction to the main control unit 33. In an example shown in FIG. 5, the operation unit 51 includes a non-defective-product-image setting unit 51a, a defective-product-image setting unit 51b, a background-image setting unit 51c, an operation/setting-mode switching unit 51d, a response-time setting unit 51e, a screen-display switching unit 51g, an increase/decrease adjusting unit 51h, a rotation-allowable-range setting unit 51j, a cancellation instructing unit 51i, and a registration-mode switching unit 51k.

(Non-Defective-Product-Image Setting Unit 51a)

The non-defective-product-image setting unit 51a is a member for receiving an operation instruction for registering a non-defective product image from the user and communicating the operation instruction to the main control unit 61. An induction-display control unit 58a of the setting managing unit 58 causes an operation-instruction display unit 43f to display on the display unit 43, a non-defective product image registration instruction read out from a registration-identification-instruction-information storing unit 54h of the image/setting storing unit 54. At the same time, the induction-display control unit 58a causes a live-image display unit 43a to display, on the display unit 43, a live image captured by the imaging unit 52 and repeatedly updated. When the SET key 42 is depressed under this situation, the non-defective-product-image setting unit 51a communicates the operation instruction to an image access unit of the setting managing unit 58. The image access unit saves, on the basis of the operation instruction, a live image at the time when the SET key 42 is depressed in a non-defective-product-image storing unit 541*a* of the image/setting storing unit 54 as a non-defective product image.

(Defective-Product-Image Setting Unit 51*b*)

The defective-product-image setting unit 51*b* is a member for receiving an operation instruction for registering a defective product image from the user and communicating the operation instruction to the main control unit 61. The induction-display control unit 58*a* of the setting managing unit 58 causes the operation-instruction display unit 43*f* to display, on the display unit 43, a defective product image registration instruction read out from the registration-identification-instruction-information storing unit 54*h* of the image/setting storing unit 54. At the same time, the induction-display control unit 58*a* causes the live-image display unit 43*a* to display, on the display unit 43, a live image captured by the imaging unit 52 and repeatedly updated. When the SET key 42 is depressed under this situation, the defective-product-image setting unit 51*b* communicates the operation instruction to the image access unit of the setting managing unit 58. The image access unit stores, on the basis of the operation instruction, a live image at the time when the SET key 42 is depressed in a defective-product-image storing unit 542*a* of the image/setting storing unit 54 as a defective product image.

In setting of the defective product image, a still-image display unit 43*b* of the display unit 43 displays, via the image access unit of the setting managing unit 58, on the display unit 43, the non-defective product image stored in the non-defective-product-image storing unit 541*a* of the image/setting storing unit 54. Consequently, in the setting of the defective product image, the user can set the defective product image while comparing the defective product image with the non-defective product image.

(Background-Image Setting Unit 51*c*)

The background-image setting unit 51*c* is a member for receiving an operation instruction for registering a background image from the user and communicating the operation instruction to the main control unit 61. The induction-display control unit 58*a* of the setting managing unit 58 causes the operation-instruction display unit 43*f* to display on the display unit 43, a background image registration instruction read out from the registration-identification-instruction-information storing unit 54*h* of the image/setting storing unit 54. When the SET key 42 is depressed under this situation, the background-image setting unit 51*c* communicates the operation instruction to the image access unit of the setting managing unit 58. The image access unit stores, on the basis of the operation instruction, a live image at the time when the SET key 42 is depressed in a background-image storing unit 543*a* of the image/setting storing unit 54 as a background image.

(Registration-Mode Switching Unit 51*k*)

The registration-mode switching unit 51*k* is a member for switching and selecting a three-point teaching mode for transitioning a state among a first registration screen, a second registration screen, and a third registration screen with screen transitioning unit 58*b* explained below and a two-point teaching mode for transitioning a state between the first registration screen and the third registration screen with the screen transitioning unit 58*b*. Note that the registration-mode switching unit 51*k* may be capable of switching the two-point teaching mode and the three-point teaching mode to a one-point teaching mode for acquiring, for example, only one image and distinguishing presence or absence of a target object of the image. As explained bellow, for example, when the SET key 42 is short-pressed, as shown in FIG. 57B, a progress bar for staring a setting mode of two-point teaching is displayed using the entire surface of the screen display 43 and the image processing sensor is switched to the setting mode of the two-point teaching. For example, when the SET key 42 is long-pressed, as shown in FIG. 57C, a progress bar for starting a setting mode of three-point teaching is displayed using the entire surface of the screen display 43. The image processing sensor is switched to the setting mode of the three-point teaching.

(Screen-Display Switching Unit 51*g*)

The screen-display switching unit 51*g* is a member for switching screen display by a first display form and screen display by a second display form. The display control unit 58*f* performs, on the display unit 43, various kinds of display in the first display form or the second display form switched by the screen-display switching unit 51*g*. Note that the screen display set as a switching target by the screen-display switching unit 51*g* may be, for example, third to fifth display forms besides the first display form and the second display form and is not limited to these display forms.

(Increase/Decrease Adjusting Unit 51*h*)

The increase/decrease adjusting unit 51*h* is a member for changing display magnification of an image displayed on the display unit. As explained above, the increase/decrease adjusting unit 51*h* can also be used as a member for adjusting the matching degree threshold. The increase/decrease adjusting unit 51*h* is configured by a pair of members of the switch on the up-side and the switch on the down-side.

(Rotation-Allowable-Range Setting Unit 51*j*)

The rotation-allowable-range setting unit 51*j* is a member for setting a rotation allowable parameter indicating a rotation allowable range referred to in image posture positioning processing included in predetermined image processing. The rotation-allowable-range setting unit 51*j* can be used as the increase/decrease adjusting unit 51*h* as well. In the example of the display surface 40*a* shown in FIG. 3A and the like, functions of the rotation-allowable-range setting unit 51*j* are allocated to a ↑ key and a ↓ key.

(Cancellation Instructing Unit 51*i*)

The cancellation instructing unit 51*i* is a member for performing a cancellation instruction according to user operation. In the example of the display surface 40*a* shown in FIG. 3A and the like, the back key 45 corresponds to the cancellation instructing unit 51*i*.

(Specific Example of the Operation Unit 51)

In the image processing sensor shown in FIG. 3A, the operation unit 51 is configured by, as hardware, the SET key 42, the BACK key 45, the MODE key 46, and the like. By button operation of the SET key 42, according to operation states, that is, display screens of the display unit 43, various operation instructions corresponding to the operation states are given to the main control unit 33. For example, on the first registration screen shown in FIG. 9 explained below, when the SET key 42, which is the operation unit 51, is depressed, a non-defective product image registration instruction for registering, as a non-defective product image, a live image displayed in the image display region PD at this point in time (real time display, display content of which is updated at any time) is given. On the second registration screen shown in FIG. 13, when the SET key 42 is depressed, a background image registration instruction for registering, as a background image, a still image displayed in the image display region PD is given.

Further, the operation unit 51 can also give a plurality of operation instructions. For example, on the first registration screen shown in FIG. 9, when the SET key 42 is depressed, in addition to the non-defective product image registration instruction for registering the non-defective product image, a screen transition instruction for transitioning the display of the display unit 43 from the first registration screen to the second registration screen is instructed to the main control unit 33. By performing such allocation of the plurality of operation instruction on the operation unit 51, operability of the user is improved. That is, by executing a plurality of operations according to one operation of the operation unit 51, that is, the depression of the SET 42, it is possible to obtain an advantage that the user can smoothly perform registration work without being aware of, for example, switching of the registration screen.

In this embodiment, the SET key 42 is used for the registration of the non-defective product image, the defective product image, and the background image. The ↑ key 44a and the ↓ key 44b are used for the matching degree threshold adjustment, the magnification setting, the item selection, and the like. The MODE key 46 is used for the display switching and the switching of the various kinds of setting. Examples of the switching of the setting include changes of a response time, a rotation allowable angle, and a registration mode.

(Imaging Unit 21)

The imaging unit 21 is a member for capturing an image and passing the captured image to the main control unit 33. In this embodiment, a CMOS is used as an imaging element of the imaging unit 21. As the imaging element, other imaging elements such as a CCD can also be used. A mode for acquiring an image with a method of, for example, reading out already-captured image data from an external storage device or transferring an image captured by an external imaging element is also included in the imaging unit referred to in this specification. An image-group acquiring unit 52a is provided in order to control the operation of the imaging unit. The image-group acquiring unit 52a can acquire a plurality of non-defective product candidate images, a plurality of defective product candidate images, and a plurality of background candidate images using the imaging unit (details are explained below).

(Display Unit 43)

The display unit 43 is a member for displaying a current sensor state and displaying content of an instruction to the user. As the display unit 43, besides an organic EL element (OLED), a liquid crystal (LCD) and the like can be used. Alternatively, besides incorporating the display unit 43 in the display surface 40a of the casing 40 as shown in FIG. 3A and the like, the display unit may be externally attached. A video signal can be output to such an external display device.

(Setting Managing Unit 58)

Referring back to FIG. 5, the setting managing unit 58 includes the display control unit 58f, the induction-display control unit 58a, an image registering unit 58g, the screen transitioning unit 58b, an image access unit 58c, a matching-degree-statistical-value access unit 58d, and a bank-switching control unit 58e.

The image/setting storing unit 54 includes an image storing unit 54i, a setting saving unit 54d, a matching-degree-statistical-value storing unit 54e, a bank-setting storing unit 54f, a threshold (first and second) storing unit 54g, and a registration-identification-instruction-information storing unit 54h. The image storing unit 54i includes a still-image storing unit 54a, a live-image storing unit 54b, and a matching-degree-statistical-time-image storing unit 54c. The still-image storing unit 54a includes a non-defective-product-image storing unit 541a, a defective-product-image storing unit 542a, and a background-image storing unit 543a.

The condition allocating unit 55 includes an imaging-condition allocating unit 55d, an image-compression-degree setting unit 55h, and an image-processing-condition allocating unit 55i. The imaging-condition allocating unit 55d includes a brightness-condition allocating unit 55e. The brightness-condition allocating unit 55e includes a brightness-condition-candidate setting unit 55f and a brightness-condition selecting unit 55g.

The setting-image processing unit 56 includes a differential-image generating unit 56a, a feature-value extracting unit 56b, a threshold calculating unit 56c, and an image compressing unit 56d.

The operation-image processing unit 57 includes a feature-value extracting unit 57a, a matching-degree calculating unit 57c, a matching-degree-statistical-value calculating unit 57e, and a pass/fail determining unit 57d. A relation among the units is explained below.

(Display Control Unit 58f)

The display control unit 58f is a member for controlling display of an image, a text, and the like on the display unit. For example, the display control unit 58f causes the display unit 43 to display a non-defective product image as a live image on the first registration screen, causes the display unit 43 to display a defective product image as a live image on the second registration screen, and causes the display unit 43 to display a background image as a live image on the third registration screen.

(Induction-Display Control Unit 58a)

The display control unit 58f includes the induction-display control unit 58a. As explained above, the induction-display control unit 58a causes the operation-instruction display unit 43f to display, on the display unit 43, a non-defective product image registration instruction read out from the registration-identification-instruction-information storing unit 54h of the image/setting storing unit 54. At the same time, induction-display control unit 58a causes the live-image display unit 43a to display, on the display unit 43, a live image captured by the imaging unit 52 and repeatedly updated.

(Image Registering Unit 58g)

The image registering unit 58g is a member for registering an image captured by the imaging unit. In the setting mode, the image registering unit 58g also plays a function of retaining, as candidate images, a plurality of image groups acquired by the image-group acquiring unit and registering images selected out of the candidate images. For example, the image registering unit 58g can also temporarily register a plurality of non-defective product image as a non-defective product image group, temporarily register a plurality of background images as a background image group, or temporarily register a plurality of defective product images as a defective product image group. The registered images are retained in the image/setting storing unit 54. In this sense, the image registering function is considered to be realized by the image registering unit 58g and the image/setting storing unit 54. However, the image registering function can also be realized by only the image registering unit or only the image/setting storing unit. For example, a memory for retaining images can be provided on the setting managing unit side or a control unit that performs image registration processing can be provided on the image/setting storing unit side.

Display examples of the display unit 43 are shown in FIGS. 7 to 11. In the display unit 43 shown in the figures, a display region is divided into two and an image display region PD for causing the display unit 43 to display an image and an explanation display region ED for displaying explanation are provided. In the example shown in FIG. 9 and the like, the image display region PD is provided on the left side of the horizontally long display unit 43 and the explanation display region ED is provided on the right side. Naturally, the display region can be displayed in various modes for interchanging the left and the right, forming the display region vertically long and dividing the display region vertically into two.

(Registration Induction Information)

The display control unit 58*f* can cause the display unit 43 to display a live image and a still image in the image display region PD. The display control unit 58*f* can cause the display unit 43 to display characters and figures for explanation and guidance in the explanation display region ED. Specifically, the display control unit 58*f* can cause the display unit 43 to display an image displayed in the image display region PD and display, as characters, figures, and the like, a procedure that should be performed according to the image. The display control unit 58*f* may cause the display unit 43 to display characters and figures for explanation as a moving image. For example, the display control unit 58*f* causes, with the induction-display control unit 58*a* of the display control unit 58*f*, the display unit 43 to display registration induction information in the explanation display region ED. The registration induction information is information for inducing the user to register an image. For example, character information and image information can be used as the registration induction information. Besides a still image, a moving image may be used as the image information. The character information and the image information can also be combined. The registration induction information includes first registration induction information for inducing registration of one image on the first registration screen and second registration induction information for inducing registration of the other image on the second registration screen. Details of the registration induction information are explained below.

(Threshold Calculating Unit 56*c*)

The threshold calculating unit 56*c* is a member for calculating a matching degree threshold with respect to a matching degree indicating a degree of matching of features values of a first image including an inspection target object that should be distinguished as a non-defective product displayed on the display unit 43 and a second image not including the inspection target object that should be distinguished as the non-defective product displayed on the display unit 43. The first image can be, for example, a non-defective product image and the second image can be, for example, a background image or a defective product image.

(Screen Transitioning Unit 58*b*)

The screen transitioning unit 58*b* is a member for transitioning the first registration screen for registering one image of the first image and the second image as an image used for the matching degree threshold calculation by the threshold calculating unit 56*c* to the second registration screen for registering the other image used for the matching degree threshold calculation by the threshold calculating unit 56*c*.

(Display Control Unit 58*f*)

The display control unit 58*f* is a member for controlling display content on the display unit 43. The display control unit 58*f* includes the induction-display control unit 58*a*.

(Induction-Display Control Unit 58*a*)

The induction-display control unit 58*a* causes the display unit 43 to display, as a live image, one image captured by the imaging unit 21 on the first registration screen. Further, the induction-display control unit 58*a* causes the display unit 43 to display the first registration induction information for inducing registration of the one image. The induction control unit causes the display unit 43 to display the live image in the image display region PD of the display unit 43 and causes the display unit 43 to display the first registration induction information in the explanation display region ED.

The induction-display control unit 58*a* can also cause the display unit 43 to display the other image as a live image in the image display region PD on the second registration screen and cause the display unit 43 to display the second registration induction information for inducing registration of the other image in the explanation display region ED.

(Image/Setting Storing Unit 54)

The image/setting storing unit 54 is a member for storing an image and setting. As the image/setting storing unit 54, an internal SRAM, an external Flash ROM, and the like can be used. For example, since the registration induction information needs to be always stored, a Flash ROM or the like, which is a nonvolatile memory, is used as the registration-identification-instruction-information storing unit 54*h* for storing the registration induction information. Note that the image/setting storing unit 54 may be provided as a separate device for each of data. A volatile or nonvolatile memory may be used as the image/setting storing unit 54. Each of data may be saved in separate member or separate device.

(Still-Image Storing Unit 54*a*)

The still-image storing unit 54*a* is a member for storing a registered image. The still-image storing unit 54*a* saves the live image, which is saved in the image/setting storing unit 54, in the still-image storing unit 54*a* (the non-defective-product-image storing unit 541*a*, the defective-product-image storing unit 542*a*, and the background-image storing unit 543*a*) of the image/setting storing unit 54 at timing of an input or timing immediately after the input via the non-defective-product-image setting unit 51*a*, the defective-product-image setting unit 51*b*, and the background-image setting unit 51*c* in the operation unit 51.

(Live-Image Storing Unit 54*b*)

The live-image storing unit 54*b* is a member for storing a live image. The live-image storing unit 54*b* always saves an image obtained from the imaging unit 52 in the image/setting storing unit 54. The live image is requested to move at extremely high speed to be repeatedly updated and temporarily stored. Therefore, an SRAM is used as the live-image storing unit 54*b* for storing the live image.

(Matching-Degree-Statistical-Time-Image Storing Unit 54*c*)

The matching-degree-statistical-time-image storing unit 54*c* is a member for storing, as matching degree statistical time image, a live image at the time when matching degree statistical values, which are all statistical values of a matching degree such as an ON time peak maximum value including a maximum value and a minimum value of the matching degree, are calculated. The matching degree statistical time image can be configured to be read out from the matching-degree-statistical-time-image storing unit 54*c* and displayed instead of a live image in a second representation form and a fourth representation form or representation forms of modifications of the second representation form and the fourth representation form.

(Setting Saving Unit 54*d*)

The setting saving unit 54*d* is a member for saving various setting content.

(Matching-Degree-Statistical-Value Storing Unit 54*e*)

The matching-degree-statistical-value storing unit 54*e* is a member for storing matching degree statistical values, which are all statistical values of a matching degree such as an ON time peak maximum value including a maximum value and a minimum value of the matching degree.

(Bank-Setting Storing Unit 54f)

The bank-setting storing unit 54f is a member for storing a plurality of settings switched by the bank switching unit 511 and read out. When the MODE button 64 and the up/down keys 44 are simultaneously depressed, BNK is switched among BNK1 to BNK4. The BNK is stored in the bank-setting storing unit 54f in association with BNK displayed on the display unit 43.

(Threshold (First and Second) Storing Unit 54g)

The threshold (first and second) storing unit 54g is a member for storing a first threshold and a second threshold compared with a matching degree of an input image when an output-channel setting unit 51m sets a channel for outputting a first determination result and a second determination result.

(Registration-Identification-Instruction-Information Storing Unit 54h)

The registration-identification-instruction-information storing unit 54h is a member for storing registration induction information for inducting registration of images that should be registered such as a non-defective product image, a defective product image, and a background image. The registration induction information is displayed in the explanation display region ED by the operation-instruction display unit 43f under the management by the induction-display control unit 58a. A nonvolatile memory, a semiconductor memory, a hard disk, and the like can be used as the registration-identification-instruction-image storing unit 54h.

(Condition Allocating Unit 55)

The condition allocating unit 55 is a member for performing adjustment for changing registration setting conditions and determining optimum registration setting conditions.

Specifically, in the setting mode, the condition allocating unit sets, according to a response time given from the response-time setting unit 51e, candidates of a plurality of different registration setting conditions that can be set, performs an evaluation on candidate images obtained under the registration setting condition candidates, registers a candidate image suitable for pass/fail determination as a registration image, and retains the registration setting conditions at this point such that an image is captured under the registration setting conditions in the operation mode to perform the pass/fail determination.

The condition allocating unit 55 includes the imaging-condition allocating unit 55d, the image-compression-degree setting unit 55h, and the image-processing-condition allocating unit 55i. The imaging-condition allocating unit 55d is capable of adjusting imaging conditions for an image such that predetermined image processing for performing the pass/fail determination can be performed within the response time set by the response-time setting unit. The imaging-condition allocating unit 55d includes the brightness-condition allocating unit 55e capable of adjusting conditions concerning brightness of an image, that is, parameters of brightness. Examples of the parameters of brightness include an exposure time and illumination intensity. The brightness-condition allocating unit 55e further includes the brightness-condition-candidate setting unit 55f and the brightness-condition selecting unit 55g.

(Brightness-Condition-Candidate Setting Unit 55f)

The brightness-condition-candidate setting unit 55f is a member for setting each of a plurality of brightness conditions as a brightness condition candidate such that a determination result is output within the give response time.

(Brightness-Condition Selecting Unit 55g)

The brightness-condition selecting unit 55g is a member for selecting brightness conditions out of a plurality of brightness condition candidates according to selection conditions on the basis of a matching degree calculated for each of the plurality of brightness condition candidates by the matching-degree calculating unit 57c.

The condition allocating unit 55 explained above determines the evaluation methods for cutting out, respectively from, for example, a non-defective product image and a background image and a defective product image and the background image, a non-defective product image from which a background is removed and a defective product image from which the background is removed and deducing, on the basis of the images from which the background is removed, optimum registration conditions for distinguishing a non-defective product and a defective product. For example, the image-compression-degree setting unit 55h changes the resolution of an image, the image-processing-condition allocating unit 55i changes a processing flow of image processing, and the brightness-condition allocating unit 55e changes brightness in capturing an image. Alternatively, the condition allocating unit 55 may include a feature-value-extraction-processing allocating unit that changes an extraction method for internal feature values. In this way, the condition allocating unit 55 changes a registration condition pattern and sets, as an optimum registration condition, a registration condition pattern under which a matching degree calculated by the threshold calculating unit 56c of the setting-image processing unit 56 is optimum. Note that this functional block may be assumed by, for example, the setting managing unit 58.

(Setting-Image Processing Unit 56)

The setting-image processing unit 56 is a member for performing image processing registration on the basis of an image to make it possible to perform an evaluation of a target image. The setting-image processing unit 56 performs registration of an image processing algorithm on the basis of at least one image among a non-defective product image, a defective product image, and a background image given to the setting-image processing unit 56, determines weight parameters of internal feature values, performs an evaluation of a target image in the operation-image processing unit 57 during registration processing, calculates a matching degree, and calculates a threshold for distinguishing the non-defective product image and the defective product image. Note that, during the registration processing in the setting mode, operation is sometimes performed to calculate a matching degree threshold. Therefore, in FIG. 5, the setting-image processing unit 56 is shown to be connected the operation-image processing unit 57.

(Differential-Image Generating Unit 56a)

The differential-image generating unit 56a is a member for excluding a background image from a non-defective product image and generating a simple differential image in which only non-defective work is extracted or excluding the background image from a defective product image and generating a simple differential image in which only defective work is extracted. In the differential images, corresponding pixels of the two images are subtracted from each other to obtain a difference. However, "differential" in this specification is not limited to simple differential processing for subtracting the corresponding pixels from each other. For example, "differential" used in a meaning including excluding an element common to a background to specify a work region.

(Feature-Value Extracting Unit 56b)

The feature-value extracting unit 56b is a member for extracting feature values from image data. The feature values are called feature points or simply called features or the like as well. Examples of the feature values include a contour (an edge), the number of edge pixels, and a luminance average/dispersion. As an algorithm for extracting such feature values from the image data, for example, for an edge feature, a known algorithm such as a Sobel filter can be used.

(Threshold Calculating Unit 56c)

The threshold calculating unit 56c is a member for calculating a threshold with respect to a matching degree indicating a degree of feature matching between a non-defective product image including an inspection target object that should be distinguished as a non-defective product or an image serving as a reference of pass/fail determination (corresponding to an example of the "first image" in claims) generated on the basis of the non-defective product image displayed on the display unit 43 and a background image (corresponding to an example of the "second image" in claims) or a defective product image (corresponding to another example of the "second image" in claims) not including the inspection target object that should be distinguished as the non-defective product displayed on the display unit 43. The threshold calculating unit 56c automatically calculates the threshold with respect to the matching degree indicating the degree of feature matching between the non-defective product image and the background image or the defective product image. When teaching is performed from two points of the non-defective product image and the background image, the threshold calculating unit 56c respectively calculates feature values of the non-defective product image and the background image and draws a threshold between the feature values. When teaching is performed from three points of the non-defective product image, the defective product image, and the background image, the threshold calculating unit 56c respectively cuts out, from the non-defective product image and the background image and the defective product image and the background image, a non-defective product image from which a background is removed and a defective product image from which the background is removed, calculates feature values of the non-defective product image and the defective product image from which the background is removed, and draws a threshold between the feature values.

(Image Compressing Unit 56d)

The image compressing unit 56d is a member for compressing an image to reduce the resolution of the image. As an image compressing method, known methods such as a Lanczos method, an average pixel method, and a bicubic method can be used. The image compressing unit 56d also functions to compress, on the basis of a given response time, an input image of a compression target to be a data size processable by predetermined image processing within the response time.

(Operation-Image Processing Unit 57)

The operation-image processing unit 57 is a member for performing the evaluation of the target image and calculating a matching degree. In a state in which the image processing algorithm is registered by the setting-image processing unit 56, the operation-image processing unit 57 causes the registered image processing algorithm to operate on an evaluation target image and calculates a matching degree of an operation image with a non-defective product image. The operation-image processing unit 57 compares the matching degree calculated with respect to the operation image and the threshold calculated by the threshold calculating unit 56c of the setting-image processing unit 56 and determines whether the work WK is a non-defective product or a defective product.

(Feature-Value Extracting Unit 57a)

The feature-value extracting unit 57a is a member for extracting feature values from image data. The feature values are called feature points or simply called features or the like as well. Examples of the feature values include a contour (an edge), the number of edge pixels, and a luminance average/dispersion. As an algorithm for extracting such feature values from the image data, for example, for an edge feature, a known algorithm such as a Sobel filter can be used. Note that the feature-value extracting unit 57a can also be used in common with the feature-value extracting unit 56b of the setting-image processing unit 56 explained below. In this case, the feature-Value extracting unit 57a can calculate feature values and send the feature values to the setting-image processing unit 56 during registration. Conversely, the feature-value extracting unit 56b of the setting-image processing unit 56 can calculate feature values and send the feature values to the operation-image processing unit 57 during operation. Alternatively, the setting-image processing unit 56 and the operation-image processing unit 57 may be integrated.

(Matching-Degree Calculating Unit 57c)

The matching-degree calculating unit 57c is a member for performing an evaluation of a target image and calculating a matching degree. The matching degree means a degree of matching with a non-defective product image. For example, when a matching degree of a target image, which is the non-defective product image, is represented as 100%, if a degree of matching of a background image and the non-defective product image is 70%, a matching degree of the background image is 70%. 85% in the middle of the matching degree of the non-defective product image and the matching degree of the background image is set as a threshold. The matching degree may be calculated as a ratio in this way. Alternatively, scores may be distributed for each of feature values. Rather than a degree, a total value of the scores distributed for each of the feature values may be set as the matching degree. In the embodiment explained above, the matching degree is defined as the degree of matching with the non-defective product image or scored values of the feature values. However, the matching degree may be defined as a degree of matching with the defective product image or can be defined as a degree of matching with a target image desired by the user by selecting the first image as appropriate.

(Matching-Degree-Statistical-Value Calculating Unit 57e)

The matching-degree-statistical-value calculating unit 57e is a member for calculating a matching degree statistical value of the matching degree, which is calculated by the matching-degree calculating unit 57c, from an operation start time or from hold clear of the matching degree statistical value. The matching-degree-statistical-value calculating unit 57e calculates an ON time peak value, ON time peak maximum/minimum values, an OFF time bottom value, and OFF time bottom maximum/minimum values tied to a maximum value, a minimum value, and a setting threshold of the matching degree. If a matching degree updated, for example, at every 3 ms exceeds a maximum value in the past, the matching-degree-statistical-value calculating unit 57e calculates a value of the matching degree as a maximum matching degree. Similarly, if the matching degree updated, for example, at every 3 ms falls below a minimum value in the past, the matching-degree-statistical-value calculating unit 57e calculates a value of the matching degree at this time as a minimum matching degree.

At an ON time when a matching degree exceeds a threshold and an inspection target object is distinguished as a non-defective product and at an end time of a current sampling period, if an ON time peak value in the sampling period exceeds an ON time peak maximum value in the past, the matching-degree-statistical-value calculating unit 57e calculates the ON time peak value as an ON time peak maximum value. If the ON time peak value in the sampling period falls below an ON time peak minimum value in the past, the matching-degree-statistical-value calculating unit 57e calculates the ON time peak value as an ON time peak minimum value. Furthermore, at an OFF time when the matching degree falls below the threshold and the inspection target object is distinguished as a defective product and at the end time of the current sampling period, if an OFF time bottom maximum value in the sampling period exceeds an OFF time bottom maximum value in the past, the matching-degree-statistical-value calculating unit 57e calculates the OFF time bottom value as an OFF time bottom maximum value. If the OFF time bottom value in the sampling period falls below the OFF time bottom maximum value in the past, the matching-degree-statistical-value calculating unit 57e calculates the OFF time bottom value as an OFF time bottom minimum value.

(Setting Managing Unit 58)

The setting managing unit 58 is a member for supervising the functional blocks. The setting managing unit 58 controls the image/setting storing unit 54, the condition allocating unit 55, the setting-image processing unit 56, and the operation-image processing unit 57 on the basis of information input by the operation unit 51 and the imaging unit 52 and displays a necessary image and information on the display unit 43. For example, in the setting mode, in a live image setting waiting state, the setting managing unit 58 always saves an image obtained from the imaging unit 21 in a memory (volatile or nonvolatile). At timing when an image registration command is received from the operation unit 51, the setting managing unit 58 registers, as a non-defective product image, a defective product image, or a background image, a live image saved in the memory. Alternatively, the setting managing unit 58 registers a live image immediately after the operation unit 51 is depressed as the non-defective product image, the defective product image, or the background image not through image data saved in the memory. The setting managing unit 58 transfers the registered image to the condition allocating unit 55 and causes the display unit 43 to display a registration result. On the other hand, in the operation mode, the setting managing unit 58 receives a live image of an evaluation target from the imaging unit 21, sends the live image to the operation-image processing unit 57, and causes the display unit 43 to display an evaluation result of the operation-image processing unit 57.

During the setting, the setting managing unit 58 always saves an image obtained from the imaging unit 52 in the image/setting storing unit 54. At timing of an input via the non-defective-product-image setting unit 51a, the defective-product-image setting unit 51b, and the background-image setting unit 51c in the operation unit 51 or at timing immediately after the input, the setting managing unit 58 saves the live image, which is saved in the image/setting storing unit 54, in the still-image storing unit 54a (the non-defective-product-image storing unit 541a, the defective-product-image storing unit 542a, and the background-image storing unit 543a) of the image/setting storing unit 54 and displays the live image on the still-image display unit 43b of the display unit 43 as a registration result.

During the operation, the setting managing unit 58 outputs an image obtained from the imaging unit 52 to the operation-image processing unit 57 as a target image and displays an evaluation result by the operation-image processing unit 57 on a determination-result display unit of the display unit 43.

(Display Control Unit 58f)

The display control unit 58f is a member for controlling display content in the display unit 43 as explained above. The display control unit 58f may include the induction-display control unit 58a. The display control unit 58f performs, on the display unit 43, various kinds of display in the first to fifth display forms switched by the screen-display switching unit 51g.

(Induction-Display Control Unit 58a)

The induction-display control unit 58a is a member for controlling display content in the display unit 43. The induction-display control unit 58a may include the screen transitioning unit 58b. A parallel display function of a live image and a non-defective product image registered last time on the second registration screen is imparted to the image access unit 58c. However, the induction-display control unit 58a may assume the function.

(Screen Transitioning Unit 58b)

The screen transitioning unit 58b is a member for transitioning the first registration screen for registering one image of the first image and the second image as an image used for the threshold calculation by the threshold calculating unit 56c to the second registration screen for registering the other image used for the threshold calculation by the threshold calculating unit 56c. The screen transitioning unit 58b causes the display unit 43 to display, as a live image, one image captured by the imaging unit 52 on the first registration screen. Further, the screen transitioning unit 58b causes the display unit 43 to display the first registration induction information for inducing registration of the one image. The screen transitioning unit 58b causes the display unit 43 to display the live image in the image display region PD of the display unit 43 and causes the display unit 43 to display the first registration induction information in the explanation display region ED.

On the second registration screen as well, the screen transitioning unit 58b can cause the display unit 43 to display the other image in the image display region PD as the live image and cause the display unit 43 to display the second registration induction information for inducing registration of the other image in the explanation display region ED.

(Image Access Unit 58c)

The image access unit 58c is a member for performing saving, deletion, and readout of a non-defective product image, a defective product image, a background image, a live image, a matching degree statistical time image, and the like. For example, on the second registration screen during teaching, the image access unit 58c causes the display unit 43 to display the live image on the left side of the display unit 43 via the live-image display unit 43a and causes the display unit 43 to display the non-defective product image registered last time on the right side via the still-image display unit 43b. Consequently, the user can register the defective product image, for example, while viewing the registered image of the non-defective product image. Therefore, it is possible to prevent unintended registration.

On the first registration screen shown in FIG. 9 in the case of the teaching of the two points of the non-defective product image and the background image, when the SET key 42, which is the operation unit 51, is depressed, the image access unit 58c saves the live image displayed in the image display region PD at this point in time in the non-defective-product-image storing unit 541a as the non-defective product image. On the second registration screen shown in FIG. 8, when the SET key 42 is depressed, the image access unit 58c saves the live image displayed in the image display region PD in the background-image storing unit 543a as the background image.

Figure 17:
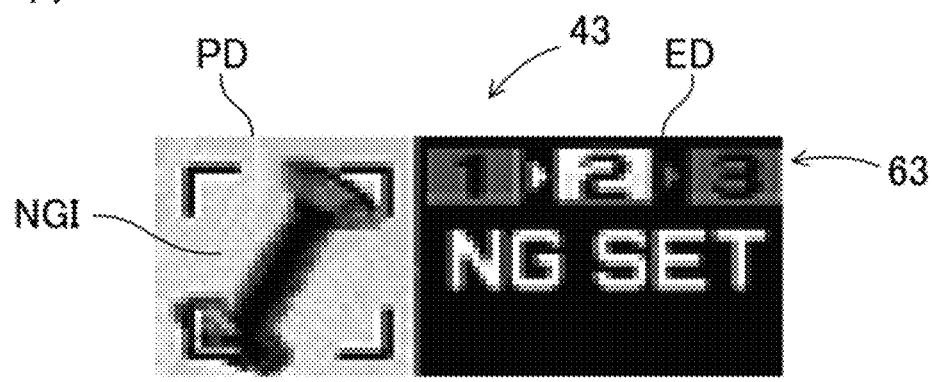
FIG. 17 is an image diagram showing an example of a second registration screen during the three-point registration.

On the second registration screen shown in FIG. 17 in the case of the teaching of the three points of the non-defective product image, the defective product image, and the background image, when the SET key 42 is depressed, the image access unit 58c saves the live image displayed in the image display region PD in the defective-product-image storing unit 542a as the defective product image. On the third registration screen shown in FIG. 18, when the SET key 42 is depressed, the image access unit 58c saves the live image displayed in the image display region PD in the background-image storing unit 543a as the background image.

(Matching-Degree-Statistical-Value Access Unit 58d)

The matching-degree-statistical-value access unit 58d is a member for performing saving, deletion, and readout of a matching degree statistical value. For example, during the operation, the matching-degree-statistical-value access unit 58d causes the matching-degree-statistical-value calculating unit 57e to calculate a matching degree statistical value, saves the matching degree statistical value in the matching-degree-statistical-value storing unit 54e, reads out the matching degree statistical value saved in the matching-degree-statistical-value storing unit 54e, and causes the display unit 43 to display the matching degree statistical value.

(Bank-Switching Control Unit 58e)

The bank-switching control unit 58e is a member for enabling a plurality of BNKs to be switched, causing the bank-setting storing unit 54f to store setting in association with BNK, reading out the setting in association with the BNK, and performing control for performing operation in the read-out setting.

(Registration of an Image in the Setting Mode)

In the image processing sensor, examples of a method of registering an image in the setting mode include the following four methods.

1. Three-Point Registration

In three-point registration, a non-defective product image, a defective product image, and a background image are registered. An object of the three-point registration is identification of a non-defective product and a defective product. When the image processing sensor is switched to the operation mode after the three-point registration is performed, a matching degree for evaluating how close an input image is to the non-defective product image is calculated.

2. Two-Point Registration (the Non-Defective Product Image and the Defective Product Image are Registered)

In the two-point registration, the non-defective product image and the defective product image are registered. An object of the two-point registration is also identification of a non-defective product and a defective product. When the image processing sensor is switched to the operation mode after the two-point registration is performed, a matching degree for evaluating how close an input image is to the non-defective product image is calculated.

Note that a difference between the two-point registration and the three-point registration is that possibility of work specifying is different depending on presence or absence of the background image. That is, in a situation in which the background image is not registered, since the differential processing cannot be performed, a non-defective work and a defective work cannot be satisfactorily specified. Since work cannot be specified, information concerning a non-defective product/a defective product during registration is "a non-defective product including a background" and "a defective product including a background". Since the background and a work region cannot be identified, when a background included in the non-defective product image and a background included in the defective product image are different (e.g., the sizes of the non-defective work and the defective work are different), identification is attempted according to a difference between the backgrounds that should originally be excluded from an evaluation target, leading to erroneous detection.

Not only during the registration but also during the operation, since a non-defective product or a defective product cannot be cut out from an input image, pass/fail determination is performed according to work including a background. In this case, even when the background unrelated to the non-defective product and the defective product changes, a matching degree changes on the basis of the change. In this way, since an unstable element (i.e., the background) is included in the identification focused only on the non-defective product and the defective product, a best identification result cannot be expected. Therefore, a difference occurs in detection performance according to presence or absence of the background image. The three-point registration capable of specifying work is expected to have higher determination performance.

3. Two-Point Registration (the Non-Defective Product Image and the Background Image are Registered)

On the other hand, as another kind of the two-point registration, an example is assumed in which the non-defective product image is registered and the background image is registered instead of the defective image. An object of the two-point registration is distinction of presence or absence of non-defective work. When the image processing sensor is switched to the operation mode after the two-point registration is performed, a probability of presence of seemingly non-defective work is calculated at a matching degree of 0 to 100%.

The two-point registration for registering the non-defective product image and the background image can also be used for the identification use. In this case, since the non-defective work is specified during registration, it is possible to perform identification operation by identifying whether the non-defective work is present on the operation screen. However, since a defective work is absent, a matching degree needs to be evaluated in the entire non-defective work. In this case, if work, which is partially chipped non-defective work, is assumed as the defective work, the matching degree has to be changed on the basis of the size of the chip. A large matching degree difference cannot be calculated with respect to a small chip. It is likely that distinction sensitivity of a non-defective product/a defective product is insufficient.

On the other hand, in the three-point registration, since the non-defective work and the defective work are registered, a region including a difference can be specified in advance. Therefore, irrespective of work and the magnitude of a difference, by performing matching degree determination in a portion including the difference, it is possible to calculate a large matching degree difference even with respect to a small chip. Therefore, a difference occurs in the identification performance according to presence of absence of the defective product image. The three-point registration capable of specifying a defective produce is expected to have higher determination performance. According to the registration of the plurality of images, a high identification property and high stability are realized compared with a method of performing registration processing with one image as in the past.

4. One-Point Registration (the Non-Defective Product Image or the Background Image is Registered)

In one-point registration, the non-defective product image or the background image is registered. An object of the one-point registration is to evaluate what is different from a registration state. For example, the one-point registration is used in a mode for registering the background image to cause the user to grasp a background state and, when some work is conveyed, reacting to the conveyance of the work. (Procedure of the Two-Point Registration for Registering the Non-Defective Product Image and the Defective Product Image)

Figure 6:
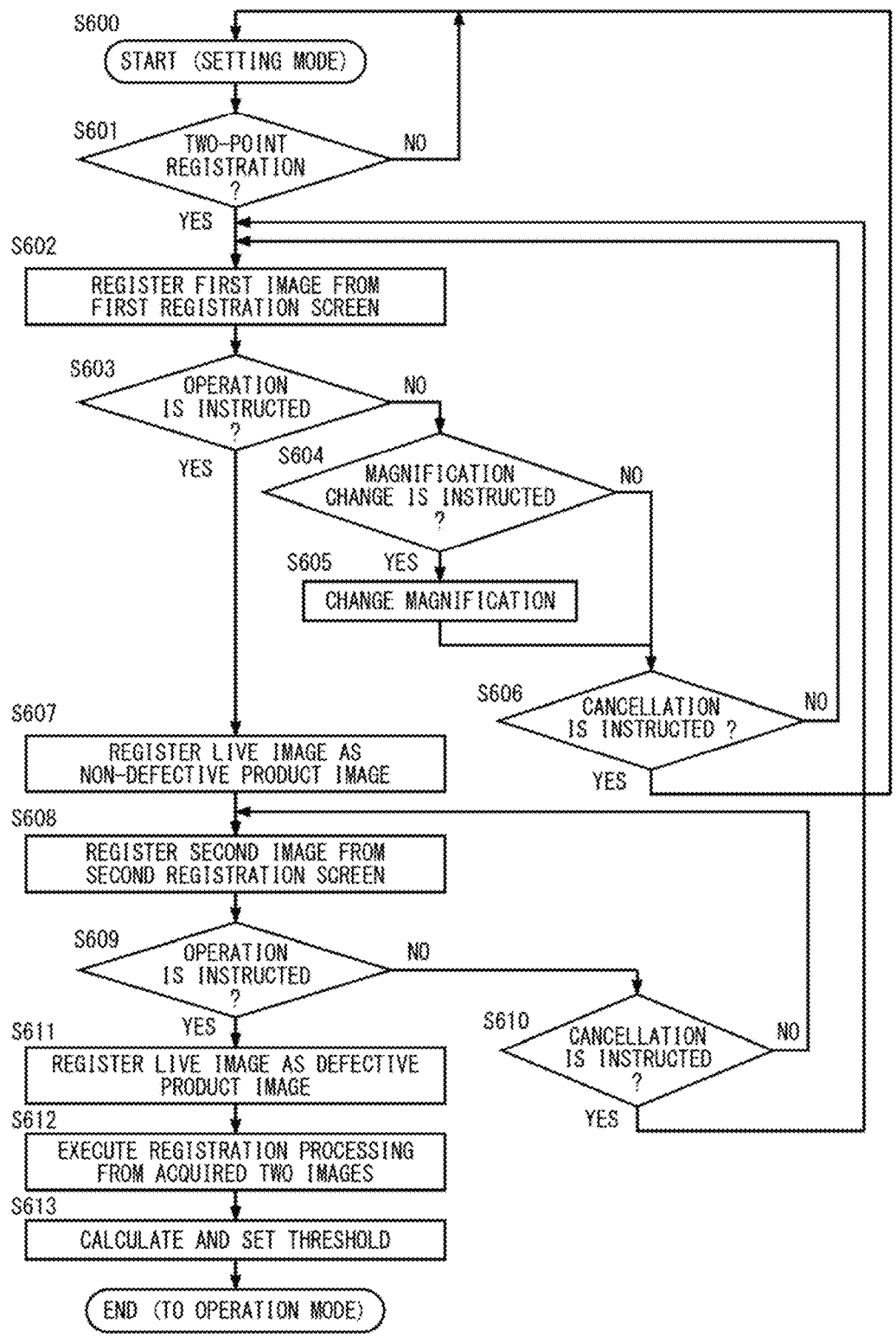
FIG. 6 is a flowchart for explaining a procedure of two-point registration for registering a non-defective product image and a defective product image.

As specific teaching, a procedure of the two-point registration is explained with reference to a flowchart of FIG. 6 viewed from the image processing sensor side and FIGS. 7 to 11. As an example of the two-point registration, two images of a non-defective product image and a defective product image are registered.

First, in step S600, the image processing sensor starts processing. In step S601, the image processing sensor determines presence or absence of switching to a two-point registration mode. The image processing sensor determines presence or absence of short-press of the SET key 42, which is a form of the operation unit 51. Specifically, the image processing sensor measures, from the operation screen of the display unit 43 operating in the operation mode shown in FIG. 7, a time in which the SET key 42 is depressed. When the time is equal to or shorter than a predetermined number of seconds (e.g., three seconds), the image processing sensor determines that the short-pressed is performed. When the short-press is detected, the image processing sensor proceeds to step S602. When the short-press is not detected, the image processing sensor stops the processing of the two-point registration mode. In an example shown in FIG. 6, the image processing sensor returns to step S600. Note that, instead of returning to step S600, the image processing sensor may shift the two-point registration mode to a three-point registration mode explained below.

Subsequently, in step S602, the image processing sensor performs registration of the first image on the first registration screen. The image processing sensor causes the display unit 43 to display a captured image. Specifically, first, the image processing sensor reads out, from the registration-identification-instruction-information storing unit, the first registration induction information, which is instruction information for registering a non-defective product image, and causes the display unit 43 to display the first registration induction information. A display example of the first registration screen on the display unit 43 is shown in FIG. 8. In the display unit 43, the image display region PD (the left side in FIG. 8) and the explanation display region ED (the right side) are provided. The display unit 43 displays a live image in the image display region PD and displays registration induction information in the explanation display region ED. The registration induction information indicates, to the user, guidance for instructing the user to register a non-defective product image as the first image. In this example, the image processing sensor causes the display unit 43 to display "SET PRESENCE" to instruct registration of an image in a "detected work presence (non-defective product)" state. In this way, the display control unit 58f causes the display unit 43 to display the first registration induction information to urge the user to place non-defective work, which should be registered as a non-defective product image, in a screen visual field and cause the imaging unit 21 to image the non-defective work. According to such display, the user can understand that a motion for placing the non-defective work is necessary at this timing. The user is guided to place the non-defective work according to the induction.

Subsequently, the display control unit 58f causes the display unit 43 to display a current image captured by the imaging unit 21 on the first registration screen. As explained above, the image display region PD is in the live image display state for updating display content on a real-time basis. When the user places the non-defective work in the screen visual field according to the first registration induction information, the user can check the non-defective work on the display unit 43 on a real-time basis as shown in FIG. 9 according to a live image display function. A live image displayed on the display unit 43 at this stage is a candidate of a non-defective product image. In this way, the display form of candidate images of the first image is the live image display. Therefore, when the user changes a position where the non-defective work is placed and a rotation angle, display content of the display unit 43 is immediately reflected. Therefore, there is an advantage that the user can easily adjust an image registered as a non-defective product image obtained by imaging the non-defective work to a desired state. That is, the user visually checks, on the display unit 43, whether size, a visual field, and the like are appropriate in registering the image as the non-defective product image. When there is no problem, the user performs registration of the image currently displayed on the display unit 43.

(Display Magnification Adjusting Function)

It is also possible to adjust display magnification of the live image displayed in the image display region PD and enlarge or reduce and display the image. According to such an enlarging and reducing function, it is possible to effectively utilize the display unit 43 having a limited display area. The enlargement and the reduction may be magnification adjustment of an optical lens provided in the imaging unit 21 besides digital zoom of a captured optical image.

Figure 10:
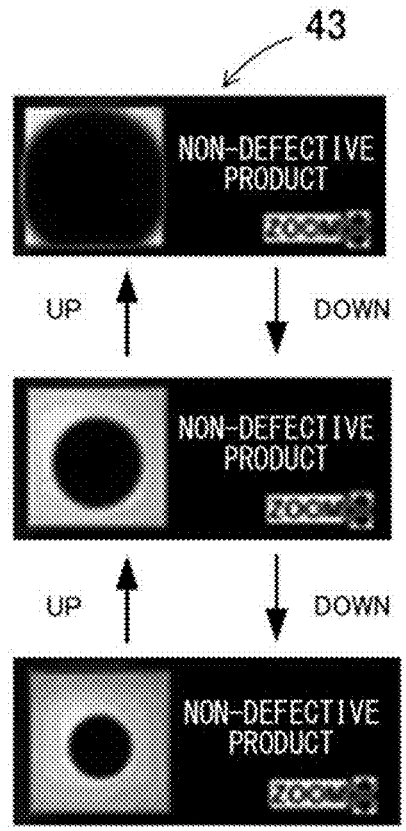
FIG. 10 is an image diagram showing an image enlarging and reducing function.

In the example shown in FIG. 9, in order to indicate that such enlarging and reducing operation is possible, an icon showing characters "ZOOM" and an increase/decrease icon 61 showing up/down arrows are displayed in the explanation display region ED as enlargement and reduction possibility display information. According to such visual display, the user is informed that enlargement and the like of an image are possible on the screen. Specifically, the user can perform image enlarging or reducing operation by operating the up/down keys 44, which are a form of the increase/decrease adjusting unit 51h provided on the display surface 40a shown in FIG. 3A and the like. For example, as shown in FIG. 10, when the ↑ key 44a of the up/down keys 44 is depressed, the image is enlarged and displayed. When the ↓ key 44b is depressed, the image is reduced and displayed. Note that, by matching a mark of the increase/decrease icon 61 and a mark attached to the up/down keys 44, which are the increase/decrease adjusting unit 51h, it is possible to cause the user to visually grasp a correspondence relation between the marks and urge smoother operation. In the examples shown in FIG. 3A and FIG. 9, $\Delta$ and $\nabla$ are displayed on the up/down keys 44 and Δ and ∇ are displayed on the increase/decrease icon 61. By matching these kinds of display, the correspondence relation is visually shown.

The display unit can be formed as a touch panel. The increase/decrease icon 61 provided side by side with the "ZOOM" icon can be caused to function as the increase/decrease adjusting unit 51*h*. For example, the image may be enlarged when the Δ icon is touched and may be reduced when the ∇ icon is touched.

In this way, the "ZOOM" icon, which is an example of the increase/decrease icon 61, is displayed on a screen on which the image enlargement and reduction display is possible. The "ZOOM" icon is not displayed on a screen on which the image enlarging and reducing function is disabled. Consequently, it is possible to inform the user that the image enlarging and reducing function can be used.

Note that, in the example shown in FIG. 9, the enlargement and reduction possibility display information is displayed in the explanation display region ED. However, for example, the display of the enlargement and reduction possibility display information is not limited to this configuration. For example, the enlargement and reduction possibility display information may be displayed in the image display region or may be displayed across the image display region and the explanation display region.

In this way, in a state in which the non-defective product image, the visual field and the magnification of which are appropriately adjusted according to necessity, is displayed in the image display region PD, the user depresses the SET key 42, which is a form of the operation unit 51, to register, as a non-defective product image, a live image displayed in the image display region PD. A specific flow of this processing is explained referring back to the flowchart of FIG. 6.

First, in step S603, the image processing sensor detects presence or absence of an operation instruction from the operation unit 51. The image processing sensor determines whether the user operates the SET key 42, which is a form of the operation unit 51. When the operation instruction is absent, that is, the user does not depress the SET key 42, the image processing sensor proceeds to step S604 and detects presence or absence of a magnification change instruction. The image processing sensor detects presence or absence of operation of the increase/decrease adjusting unit 51*h*. In the example of the display surface 40*a* shown in FIG. 3A and the like, the up/down keys 44, which are increase/decrease buttons, correspond to the increase/decrease adjusting unit 51*h*.

When the operation of the increase/decrease adjusting unit 51*h* is detected in step S604, the image processing sensor proceeds to step S605 and changes display magnification in the display unit 43. In the example shown in FIG. 3A and the like, the display magnification is increased and an image is enlarged and displayed (zoom-in or tele) when the ↑ key 44*a* of the up/down keys 44 is depressed. On the other hand, the display magnification is reduced and the imaging region is widened (zoom-out or wide) when the ↓ key 44*b* is depressed. Thereafter, the image processing sensor proceeds to step S606. Alternatively, the image processing sensor may return to step S602 and repeat the display.

On the other hand, when the operation of the increase/decrease adjusting unit 51*h* is not detected in step S604, the image processing sensor proceeds to step S606 and determines presence or absence of a cancellation instruction. The cancellation instruction is performed from the cancellation instructing unit. In the example of the display surface 40*a* shown in FIG. 3A and the like, the BACK key 45 corresponds to the cancellation instructing unit. The BACK key 45 is a key that the user operates when stopping the image registration processing and the like. When the cancellation instruction is detected, the image processing sensor stops the processing (e.g., returns to step S600 or stops the two-point registration and returns to the operation screen shown in FIG. 7).

When the operation instruction is received in step S603, that is, when the user depresses the SET key 42, the image processing sensor proceeds to step S607 and registers, as a non-defective product image, a live image currently being displayed in the image display region PD.

Figure 11:
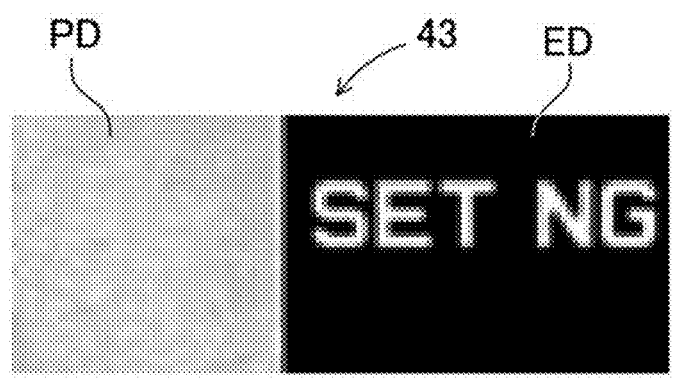
FIG. 11 is an image diagram showing an example of a second registration screen during the two-point registration. An image diagram showing an example in which a background image is displayed excluding work from FIG. 9.

Further, in step S608, the image processing sensor performs registration of the second image from the second registration screen. Therefore, the image processing sensor needs to capture an image anew and cause the display unit to display the image. The image processing sensor reads out, from the registration-identification-instruction-information storing unit, the second registration induction information, which is instruction information or induction information for registering a defective product image, causes the display unit 43 to display the second registration induction information, and configures the second registration screen. Specifically, as shown in FIG. 11, the display control unit 58*f* causes the display unit 43 to display the second registration induction information and urges the user to place, in the screen visual field, defective work that should be registered as a defective product image. Consequently, the user can understand that work for placing the defective work is necessary at this timing. The user is guided to work that the user should perform. In other words, with visual induction through the display unit 43, it is possible to avoid a risk that the user mistakes timing for placing non-defective work and timing for placing defective work.

When the user places the defective work according to the second registration induction information displayed on the second registration screen of the display unit 43 in this way, an image captured anew by the imaging unit 21 is displayed on the display unit 43. Specifically, the display control unit 58*f* causes the display unit 43 to display, as a live image, a current image serving as a candidate of a defective product image. In this state, as shown in FIG. 11, the user can check a live image serving as a candidate of a defective product image obtained by imaging the defective work on the display unit 43. Specifically, before registering the live image as the defective product image, the user can visually check whether there is no problem in size, a visual field, and the like and can register the defective product image after determining that the defective product image can be registered. In an example shown in FIG. 11, "SET NG" is displayed in the explanation display region ED to instruct to register a "detected work is present (defective product)" state as the second registration induction information. On the other hand, an image serving as a candidate of the defective product image is displayed in the image display region PD as a live image.

Subsequently, in step S609, the image processing sensor detects whether an operation instruction is received from the operation unit 51. When the operation instruction is not received, that is, the user does not depress the SET key 42, the image processing sensor proceeds to step S610 and determines presence or absence of a cancellation instruction. When depression of the BACK key 45 is detected, the image processing sensor returns to step S602. When operation of the BACK key 45 is not detected, the image processing sensor returns to step S608 and repeats the processing.

Note that, in the registration of the defective product image, the display magnification changing function is not carried out. This is because, in image processing such as acquisition of a difference explained below, it is necessary to match magnifications of the non-defective product image and the defective product image. Therefore, by maintaining, during the registration of the defective product image, display magnification set during the registration of the non-defective product image, it is possible to directly register images having the same magnification and smoothly perform subsequently image work. Scales of the non-defective product image and the defective product image are often generally the same degree. Therefore, it is considered that the defective product image can also be often appropriately captured even at magnification set in the non-defective product image.

However, for example, when the defective work is larger than the non-defective work, the user may desire to change the magnification. In this case, change of the display magnification may be added with respect to the candidate of the defective product image as in the candidate of the non-defective product image. For example, the image processing sensor causes the display unit 43 shown in FIG. 11 to display the enlargement and reduction possible display information like the "ZOOM" icon. Note that, in this case, it is desirable to register the non-defective product image again in order to match display magnification of a registered non-defective product image with display magnification of the defective product image. However, the non-defective product image and the defective product image may be enlarged or reduced to match the magnification of the non-defective product image and the magnification of the defective product image using digital zoom or the like. In this case, it is possible to save labor and time for capturing the non-defective product image again.

On the other hand, when the operation instruction is received in step S609, that is, when the user depresses the SET key 42, the image processing sensor proceeds to step S611 and registers, as the defective product image, a live image being currently displayed in the image display region PD.

Further, the image processing sensor proceeds to step S612 and saves the registered non-defective product image and the registered defective product image in the image/setting storing unit 54. The image processing sensor proceeds to step S613, calculates a matching degree threshold from the non-defective product image and the defective product image, and further sets the calculated matching degree threshold. In this way, the image processing sensor can perform the two-point registration, automatically calculate an appropriate matching degree threshold from the non-defective product image and the defective product image, and set the matching degree threshold. The image processing sensor may cause the display unit 43 to display the set matching degree threshold. The image processing sensor may enable the user to check the matching degree threshold by switching the registration screen of the setting mode to the operation screen during the operation. For example, by returning to the operation mode after the end of the setting mode of the two-point registration, on the operation screen shown in FIG. 7, the image processing sensor may cause the display unit 43 to display the set matching degree threshold and enable the user to check a numerical value. The image processing sensor may be configured to cause the display unit 43 to flash and display a matching degree threshold set anew or updated and indicate that the matching degree threshold is set or updated.

As explained above, the registration of the non-defective product image (step S607) and the switching to the screen for registration of the defective product image (step S608) are simultaneously performed by operating the operation unit 51 once. The registration of the defective product image (step S611) and the registration processing to the calculation of the matching degree threshold (step S612 and subsequent steps) are also simultaneously performed by operating the operation unit 51 once. Consequently, the user can advance the setting work of the two-point registration simply by pressing the SET key 42. In other words, it is possible to set a matching degree threshold suitable for the pass/fail determination by performing the work for placing work and depression of the SET key 42 according to the induction displayed on the screen of the display unit 43 without requiring complicated operation.

Note that power saving is achieved by collectively performing these operations by operating the operation unit 51 once. However, on the other hand, the respective operations can be individually instructed. For example, it is also possible to operate the operation unit to perform the registration of the non-defective product image and further operate the operation unit to perform the switching to the screen for registration of the defective product image.

As explained above, it is possible to select feature values in which a difference between the non-defective product image and the defective product image conspicuously appears. That is, since a work region of the non-defective product and the defective product are extracted using the difference, it is possible to perform adjustment for maximizing a feature difference in the region. It is possible to obtain an advantage that the registration work can be easily performed. That is, the user only has to push the SET key 42 while viewing an image. It is possible to eliminate the need for a tool frame and parameter setting of the image processing sensor in the past.

(Procedure of the Two-Point Registration for Registering the Non-Defective Product Image and the Background Image)

Figure 12:
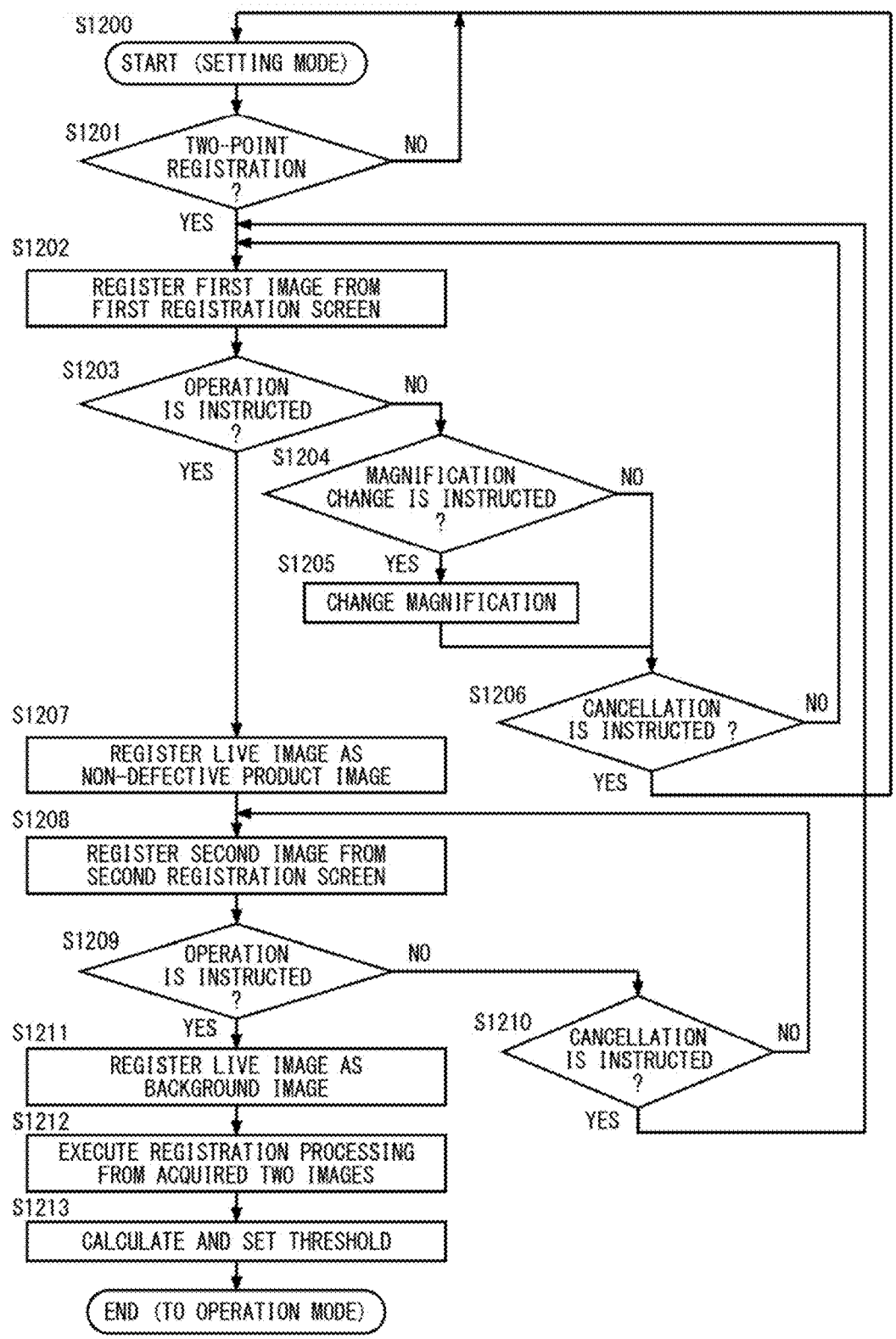
FIG. 12 is a flowchart for explaining a procedure of two-point registration for registering a non-defective product image and a background image.

In the example explained above, the two-point registration for registering the two images of the non-defective product image and the defective product image is explained. However, the two-point registration is not limited to the combination of the images and can be a combination of other images. For example, the two-point registration of the two images of the non-defective product image and the background image without work may be performed. Such an example is explained with reference to a flowchart of FIG. 12.

First, in step S1200, the image processing sensor starts processing. In step S1201, the image processing sensor determines presence or absence of switching to the two-point registration mode. The image processing sensor determines presence or absence of short-press of the SET key 42. When the short-press is detected, the image processing sensor proceeds to step S1202. When the short-press is not detected, the image processing sensor stops the processing of the two-point registration mode.

Subsequently, in step S1202, the image processing sensor performs registration of the first image on the first registration screen. The image processing sensor causes the display unit 43 to display a captured image. Specifically, first, the image processing sensor reads out, from the registration-identification-instruction-information storing unit, the first registration induction information, which is instruction information for registering a non-defective product image, and causes the display unit 43 to display the first registration induction information (FIG. 8). The display control unit 58f causes the display unit 43 to display the first registration induction information to urge the user to place non-defective work, which should be registered as a non-defective product image, in the screen visual field and cause the imaging unit 21 to image the non-defective work. According to such display, the user can understand that a motion for placing the non-defective work is necessary at this timing. The user is guided to place the non-defective work according to the induction.

Subsequently, in step S1203, the display control unit 58f causes the display unit 43 to display a current image captured by the imaging unit 21. The display unit 43 is in the live image display state for updating display content on a real-time basis. In this state, the user can check the live image serving as a candidate of a non-defective product image, which is obtained by imaging the non-defective work, on the display unit 43 as shown in FIG. 9. Specifically, the user checks whether there is a problem in size, a visual field, and the like in registering the non-defective work as the non-defective product image. When there is no problem, the user operates the operation unit 51 (the SET key 42).

Subsequently, in step S1204, the image processing sensor detects whether an operation instruction from the operation unit 51 is received. When the operation instruction is not received, that is, when the user does not operate the operation unit 51, the image processing sensor proceeds to step S1205 and determines whether a "return" instruction is received. For example, in the example of the operation unit 51 shown in FIG. 3A and the like, the BACK key 45 corresponds to the return instruction. The BACK key 45 is a key that the user operates to stop the registration of the non-defective product image. When the operation of the BACK key 45 is detected, the image processing sensor returns to step S1200. When the operation of the BACK key 45 is not detected, the image processing sensor returns to step S1203 and repeats the processing.

On the other hand, when the operation instruction is received in step S1204, that is, when the user operates the operation unit 51, the image processing sensor proceeds to step S1206 and registers, as a non-defective product image, a live image being currently displayed in the image display region PD. The procedure explained above is the same as the procedure of the two-point registration for registering the non-defective product image and the defective product image shown in FIG. 6 explained above.

Figure 13:
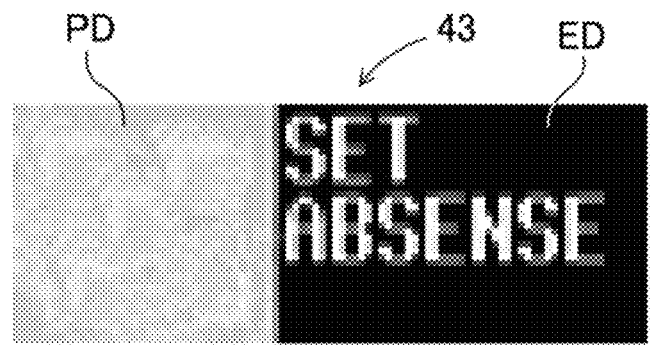
FIG. 13 is an image diagram showing a second registration screen for registering an image "without detected work" during the two-point registration.

Further, in step S1207, the image processing sensor performs registration of the second image on the second registration screen. Specifically, the image processing sensor reads out, from the registration-identification-instruction-information storing unit, the second registration induction information, which is instruction information for registering a background image, and causes the display unit 43 to display the second registration induction information. As shown in FIG. 13, the display control unit 58f causes the display unit 43 to display the second registration induction information and urges the user to remove non-defective work, which should be registered as a background image, from an imaging position. The user can understand that a motion for removing work is necessary according to the displayed second registration induction information. The user is induced to perform a motion necessary at this stage. In other words, with visual induction through the display unit 43, it is possible to avoid a risk that the user mistakes timing for placing non-defective work and timing for removing defective work.

Subsequently, in step S1208, the image processing sensor causes the display unit 43 to display a current image (a candidate of a background image) captured by the imaging unit 21. The display unit 43 may display the background image as a still image besides displaying the background image as a live image (FIG. 13). That is, unlike the work, adjustment of the visual field and the size of the background image is unnecessary. Therefore, it is sufficient to confirm that the work is absent. Therefore, the object can be achieved even if the background image is displayed as the live image. There is an advantage that it is possible to simplify the processing by displaying the still image. When there is no problem in registering the non-defective work as the background image, the user operates the operation unit 51 (the SET key 42). Note that the display of the background image may be omitted.

Subsequently, in step S1209, the image processing sensor detects whether an operation instruction is received from the operation unit 51. When the operation instruction is not received, that is, when the user does not operate the operation unit 51, the image processing sensor proceeds to step S1210 and determines whether a "return" instruction is received. When the operation of the BACK key 45 is detected, the image processing sensor returns to step S1201. When the operation of the BACK key 45 is not detected, the image processing sensor returns to step S1208 and repeats the processing.

On the other hand, when the operation instruction is received in step S1209, that is, when the user operates the operation unit 51, the image processing sensor proceeds to step S1211 and registers, as a background image, an image currently being displayed in the image display region PD.

Further, in step S1212, the image processing sensor saves the registered two images in the image/setting storing unit 54. In step S1213, the image processing sensor calculates a matching degree threshold from the non-defective product image and the background image and sets the matching degree threshold. In this way, it is possible to perform the two-point registration, automatically calculate an appropriate matching degree threshold from the non-defective product image and the background image, and set the matching degree threshold.

As explained above, it is possible to perform distinction processing with the influence of a background eliminated. That is, by registering the background image, it is possible to perform an evaluation that is less easily affected by background elements.

Note that, in the example explained above, the procedure for registering the non-defective product image as the first registration screen and subsequently registering the background image as the second registration screen is explained. In this way, the order of registering images during teaching is specified in advance. The registration induction information is used such that the user does not mistake images that should be registered and the order of the registration. However, the order of registering the images is not limited to the example explained above. It goes without saying that it is possible to specify the order as any order for, for example, registering the background image first and subsequently registering the non-defective product image.

(Three-Point Registration)

The two-point registration for registering the two points of the non-defective product image and the other image is explained above. However, in the present invention, images to be registered are not limited to the two images. Three or more images can also be registered. Most of image processing sensors in the past register only one image and enable a plurality of image processing tools to be set with respect to the image. In other words, an image processing sensor that registers a plurality of images is hardly present. When work for setting a plurality of image processing tools with respect to one image is assumed as work on the user side, the user needs to perform work for, for example, selecting, out of a plurality of image processing tools prepared in advance, a tool necessary for detection of image processing desired by the user, setting a window as a region to which the tool is applied, selecting parameters of the image processing, and setting or finely adjusting the parameters. It is difficult for a user to appropriately perform such work unless the user understands effects and uses of prepared image processing tools and has a certain degree of knowledge. Further, the work itself is also troublesome.

From the image processing sensor side, when one non-defective product image is registered, since the non-defective product image is registered as a whole, the non-defective product image is registered as an image including a background. Therefore, the image processing of the image including the background image is performed and the pass/fail determination is performed. A background portion is present not only in the non-defective product image but also in the defective product image. Therefore, if the background portion is large, a difference between the defective product image and the non-defective product image decreases. It is difficult to detect a defective product. On the other hand, when a light amount of the sunlight changes between the daytime and the night and a light amount and a tint of illumination light change, it is likely that even a non-defective product is distinguished as a defective product according to a difference of the illumination light. In this way, the image processing sensor in the past cannot determine a boundary between a region of target work and a background. Therefore, the image processing is performed on a portion including the portion of the background, which is originally unnecessary, in the pass/fail determination and fail/pass determination. As a result, a difference between the non-defective product and the defective product depends on the background and the illumination light as well. The image processing cannot be appropriately performed on the basis of the difference between the non-defective product and the defective product desired to be detected.

On the other hand, in this embodiment, the three images of the non-defective product image, the defective product image, and the background image are registered. Therefore, it is possible to extract non-defective work and defective (NG) work excluding the background can be extracted. It is possible to improve the accuracy of the pass/fail determination. Specifically, by registering not only the non-defective product image but also the background image, it is possible to extract an unnecessary portion such as the background and exclude the unnecessary portion from the distinction target. Further, in the registration of the images, it is possible to calculate and set an appropriate matching degree threshold simply be sequentially registering the three images. It is possible to eliminate the need for the complicated work for, for example, setting a window and setting image processing parameter as in the past. Substantial power saving of the setting work itself is realized.

More specifically, in this embodiment, in the three-point registration, the three images of the non-defective product image, the defective product image, and the background image are registered. A difference between the non-defective product image and the background image and a difference between the defective product image and the background image are extracted according to the three images. Consequently, it is possible to extract non-defective work and defective work excluding the background.

Figure 14A:
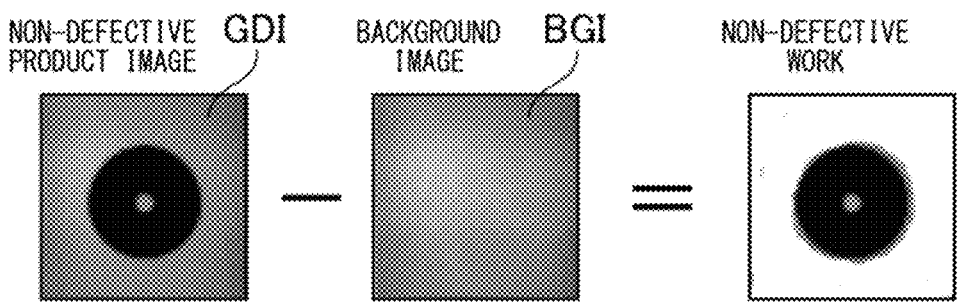
FIG. 14A is a schematic diagram showing a state in which a simple differential image from which only non-defective work is extracted is generated excluding a background image from a non-defective product image and FIG. 14B is a schematic diagram showing a state in which simple differential image from which only defective work is extracted is generated excluding the background image from a defective product image.
Figure 14B:
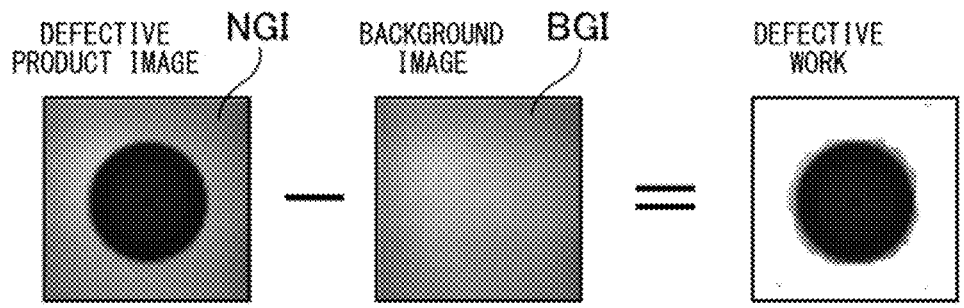
Figure 15A:
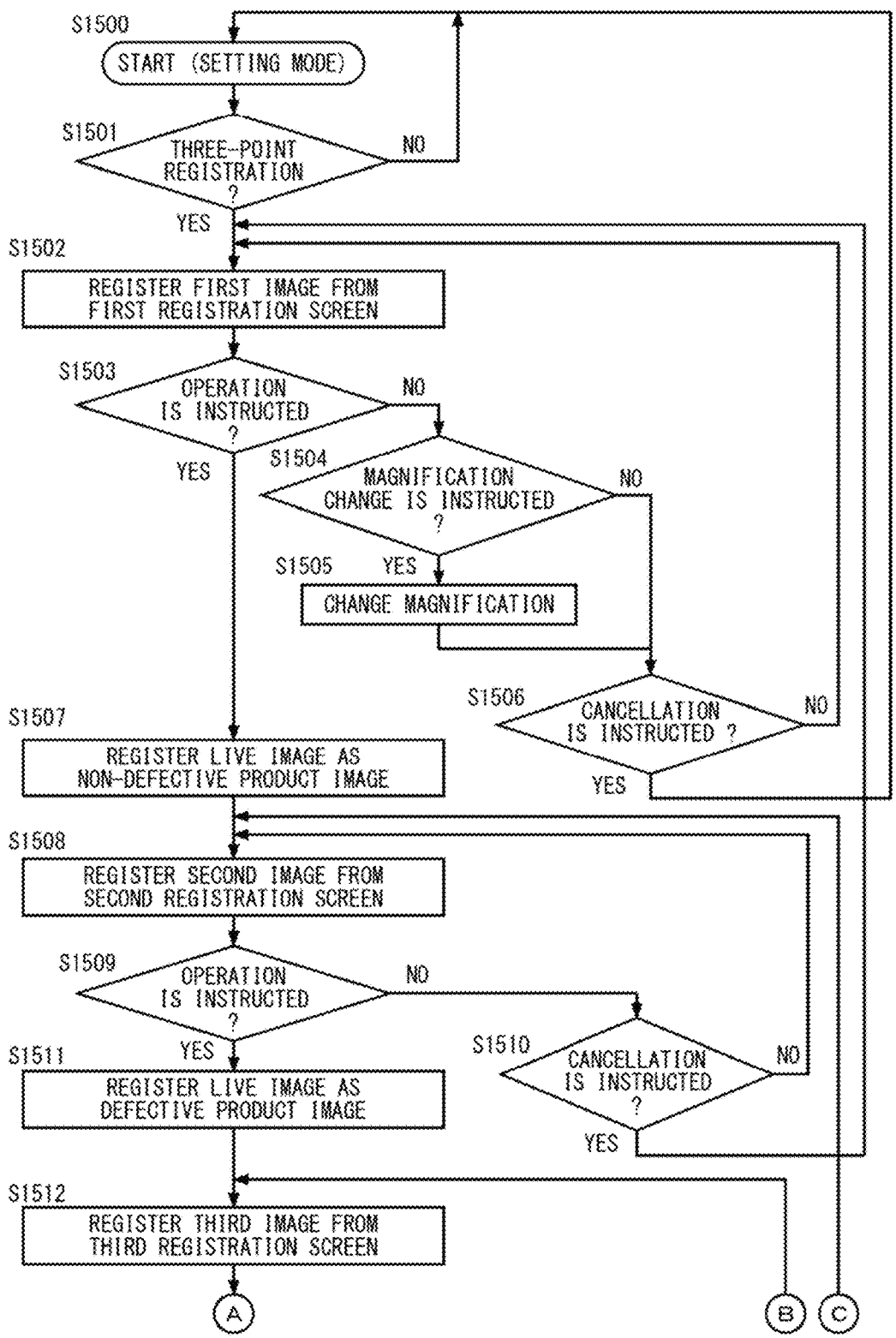
FIG. 15A is a flowchart for explaining a part of a procedure of three-point registration.
Figure 15B:
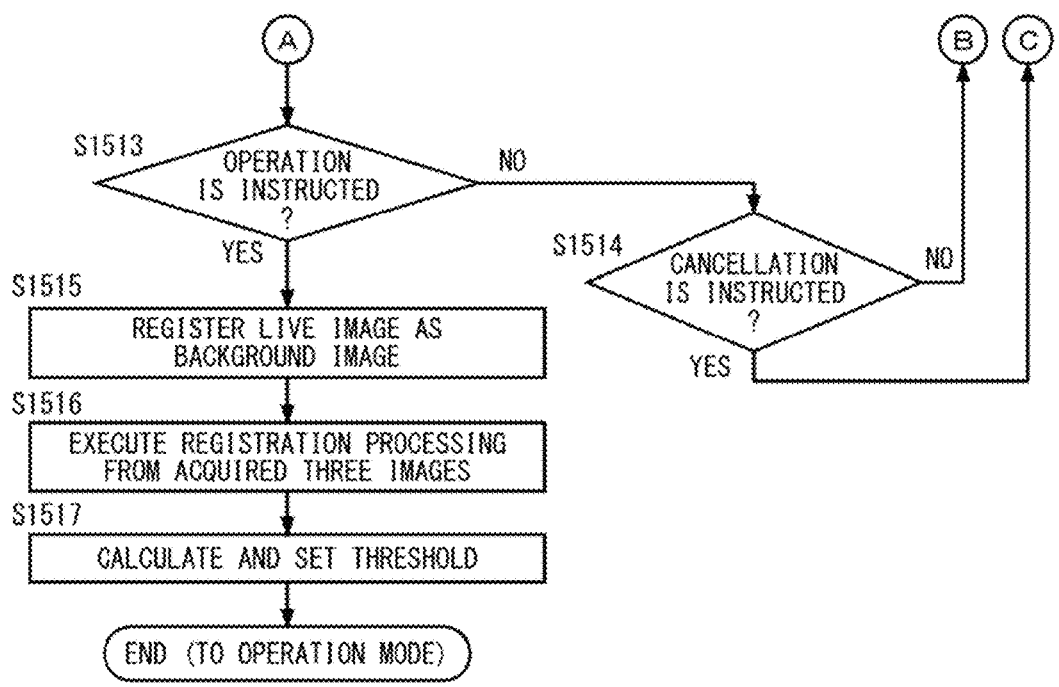
FIG. 15B is a flowchart for explaining a procedure of the three-point registration following FIG. 15A.

In FIG. 14A, an example is shown in which a simple differential image from which only the non-defective work is extracted is generated excluding a background image BGI from a non-defective product image GDI. In FIG. 14B, an example is shown in which a simple differential image from which only defective work is extracted is generated excluding the background image BGI from a defective product image NGI. In such a differential image, a difference is obtained by subtracting corresponding pixels of the two images from each other.

However, "differential" in this specification is not limited to simple differential processing for subtracting the corresponding pixels from each other. For example, "differential" used in a meaning including excluding an element common to a background to specify a work region.

(Procedure of the Three-Point Registration)

A procedure for performing the three-point registration for registering the three images of the non-defective product image, the defective product image, and the background image in the setting mode is explained below with reference to a flowchart of FIGS. 15A and 15B and FIGS. 16 to 18.

First, in step S1500, the image processing sensor starts processing. In step S1501, the image processing sensor determines presence or absence of switching to the three-point registration mode. The image processing sensor determines presence or absence of long-press of the SET key 42. Specifically, the image processing sensor measures, from the operation screen of the display unit 43 shown in FIG. 7, a time in which the SET key 42 is depressed. When the time is equal to or longer than a predetermined number of seconds (e.g., three seconds), the image processing sensor determines that the long-press is performed. When the long-press is detected, the image processing sensor proceeds to step S1502. When the long-press is not detected, the image processing sensor stops the processing of the three-point registration mode. In an example shown in FIGS. 15A and 15B, the image processing sensor returns to step S1500. Note that the image processing sensor may shift the three-point registration mode to the two-point registration mode in the case of the short-press.

Subsequently, in step S1502, the image processing sensor performs registration of the first image on the first registration screen. The image processing sensor causes the display unit 43 to display a captured image. Specifically, first, the image processing sensor reads out, from the registration-identification-instruction-information storing unit, the first registration induction information, which is instruction information for registering a non-defective product image, and causes the display unit 43 to display the first registration induction information. The display control unit 58f causes the display unit 43 to display the first registration induction information to urge the user to place non-defective work, which should be registered as a non-defective product image, in the screen visual field and cause the imaging unit 21 to image the non-defective work. According to such display, the user can understand that a motion for placing the non-defective work is necessary at this timing. The user is guided to place the non-defective work according to the induction.

Figure 16:
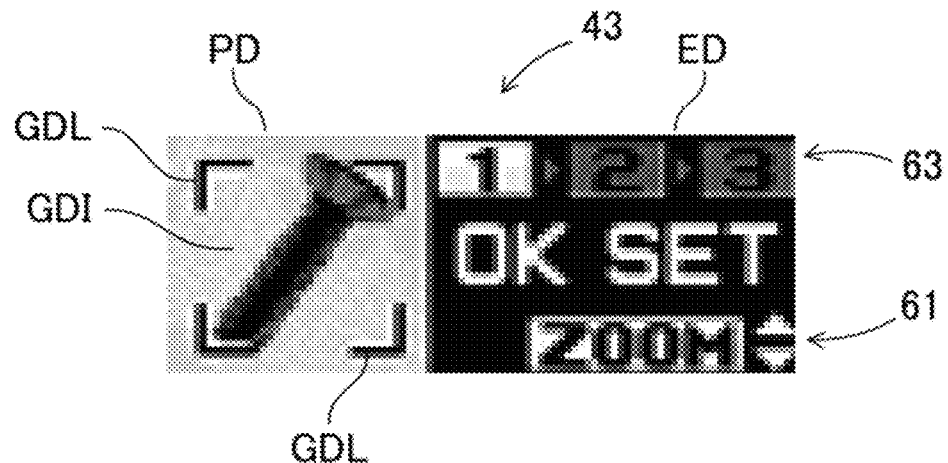
FIG. 16 is an image diagram showing an example of a first registration screen during the three-point registration.

Further, the image processing sensor causes the display unit 43 to display a current image captured by the imaging unit 21. The display unit 43 is in the live image display state for updating display content on a real-time basis. In this state, as shown in FIG. 16, the user can check, on the display unit 43, a live image serving as a candidate of the non-defective product image GDI obtained by imaging the non-defective work. Specifically, in registering the live image as the non-defective product image GDI, the user checks whether there is no problem in size, a visual field, and the like. When there is no problem, the user operates the operation unit 51 (the SET key 42).

Note that, in an example shown in FIG. 16, registration order information 63 indicating the order of the images that should be registered is displayed on the explanation display region ED (details are explained below). A "ZOOM" icon is also provided as enlargement and reduction possibility display information. The registration order information 63 is arranged in an upper part of the explanation display region ED and the enlargement and reduction possibility display information is arranged in a lower part of the explanation display region ED. However, the registration order information 63 and the enlargement and reduction possibility display information are not limited to this arrangement example. Further, in the image display region PD, guide lines GDL for absorbing differences of work are displayed (details are explained below).

Subsequently, in step S1503, the image processing sensor detects whether an operation instruction from the operation unit 51 is received. When the operation instruction is not received, that is, when the user does not depress the SET key 42, the image processing sensor proceeds to step S1504 and detects presence or absence of a magnification change instruction. The image processing sensor detects presence of absence of operation of the increase/decrease adjusting unit 51h. In the example of the display surface 40a shown in FIG. 3A and the like, the image processing sensor detects presence or absence of depression of the up/down keys 44, which are the increase/decrease buttons. When the operation of the increase/decrease adjusting unit 51h is detected in step S1504, the image processing sensor proceeds to step S1505 and changes display magnification. Thereafter, the image processing sensor proceeds to step S1506. Alternatively, the image processing sensor may return to step S1502 and repeat the display. On the other hand, when the operation of the increase/decrease adjusting unit 51h is not detected in step S1504, the image processing sensor proceeds to step S1506 and determines presence or absence of a cancellation instruction. The image processing sensor determines whether a "return" instruction is received. When the operation of the BACK key 45 is detected, the image processing sensor returns to step S1500. When the operation of the BACK key 45 is not detected, the image processing sensor returns to step S1502 and repeats the processing. Alternatively, the image processing sensor may stop the three-point registration and return to the operation screen shown in FIG. 7.

On the other hand, when the operation instruction is received in step S1503, that is, when the user operates the operation unit 51, the image processing sensor proceeds to step S1507 and registers, as the non-defective product image GDI, a live image being currently displayed in the image display region PD.

Further, in step S1508, the image processing sensor performs registration of the second image on the second registration screen. Specifically, the image processing sensor reads out, from the registration-identification-instruction-information storing unit, the second registration induction information, which is instruction information for registering a defective product image, and causes the display unit 43 to display the second registration induction information. The display control unit 58f causes the display unit 43 to display the second registration induction information and urges the user to place defective work, which should be registered as a defective product image, in the screen visual field.

Further, the image processing sensor causes the display unit 43 to display a current image (a candidate of a defective product image) captured by the imaging unit 21. An example of such a second registration screen is shown in FIG. 17. The image processing sensor causes the display unit 43 to display a candidate of the defective product image NGI in the image display region PD as a live image. In order to register the current image as the defective product image NGI, the user performs adjustment of an imaging position, a posture, and magnification according to necessity. When determining that the current image can be registered on the live image, the user operates the operation unit 51 (the SET key 42).

Subsequently, in step S1509, the image processing sensor detects whether an operation instruction from the operation unit 51 is received. When the operation instruction is not received, that is, when the user does not operate the operation unit 51, the image processing sensor proceeds to step S1510 and determines whether a cancellation instruction is received. When a "return" instruction, for example, the depression of the BACK key 45 is detected, the image processing sensor performs predetermined operation for, for example, stopping the processing and returning to step S1500. When the depression of the BACK key 45 is not detected, the image processing sensor returns to step S1508 and repeats the processing.

On the other hand, when the operation instruction is received in step S1509, that is, when the user operates the operation unit 51, the image processing sensor proceeds to step S1511 and registers, as the defective product image NGI, a liver image currently being displayed in the image display region PD.

Figure 18:
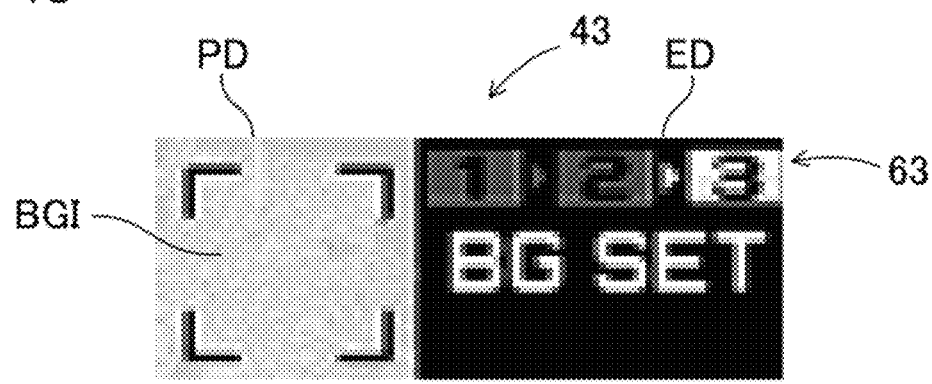
FIG. 18 is an image diagram showing an example of a third registration screen during the three-point registration.

Further, in step S1512, the image processing sensor performs registration of the third image on the third registration screen. Specifically, the image processing sensor reads out third registration induction information, which is instruction information for registering a background image, and causes the display unit 43 to display the third registration induction information. The display control unit 58f causes the display unit 43 to display the second registration induction information and urges the user to remove the defective work from the imaging position in order to capture a background image. According to the displayed third registration induction information, the user is instructed to remove the work and induced to perform necessary work, that is, capture a background image without the work. Consequently, the captured background image BGI is displayed in the image display region PD. An example of such a third registration screen is shown in FIG. 18. Note that the background image can be displayed as a still image as explained above besides being displayed as the live image. That is, unlike the work, adjustment of the visual field and the size of the background image is unnecessary. Therefore, it is sufficient to confirm that the work is absent. Therefore, the object can be achieved even if the background image is displayed as the live image. There is an advantage that it is possible to simplify the processing by displaying the still image. Alternatively, the display of the background image may be omitted. When there is no problem in registering the non-defective work as the background image, the user operates the operation unit 51 (the SET key 42).

Further, in step S1513, the image processing sensor detects whether an operation instruction from the operation unit 51 is received. When the operation instruction is not received, for example, when the user does not depress the SET key 42, the image processing sensor proceeds to step S1514 and determines whether a cancellation instruction is received. When, for example, the operation of the BACK key 45 is detected as a "return" instruction, the image processing sensor performs predetermined processing for, for example, returning to step S1512. When the operation of the BACK key 45 is not detected, the image processing sensor returns to step S1512 and repeats the processing.

On the other hand, when the operation instruction is received in step S1513, for example, when the user depresses the SET key 42, the image processing sensor proceeds to step S1515 and registers, as the background image BGI, an image currently being displayed in the image display region PD.

Further, in step S1516, the image processing sensor saves the registered three images in the image/setting storing unit 54. In step S1517, the image processing sensor calculates a matching degree threshold from the non-defective product image GDI, the defective product image NGI, and the background image BGI and sets the matching degree threshold. In this way, the image processing sensor can perform the three-point registration, automatically calculate an appropriate matching degree threshold from the non-defective product image GDI, the defective product image NGI, and the background image BGI, and set the matching degree threshold.

In the example of the three-point registration, the image processing sensor causes the enlarging and reducing function to function only when the non-defective product image GDI is registered on the first registration screen and does not cause the enlarging and reducing function to work on the second registration screen and the third registration screen. That is, the image processing sensor registers the second image and the third image while keeping the magnification set on the first registration screen fixed. Complication and disorder of setting work of the user are avoided by control for automatically turning on/off such an enlarging and reducing function to achieve simplification of operation. However, the enlarging and reducing function may be turned on the second registration screen and the third registration screen.

In the example of the three-point registration explained above, the procedure for registering the non-defective product image GDI as the first registration screen first, subsequently registering the defective product image NGI as the second registration screen, and registering the background image BGI as the third registration screen is explained. The order of registering the images is not limited to the order explained above. It goes without saying that it is possible to specify any order for, for example, registering the background image as the second registration screen first and subsequently registering the defective product image.

(Procedure of the One-Point Registration for Registering the Non-Defective Product Image or the Background Image)

Figure 19:
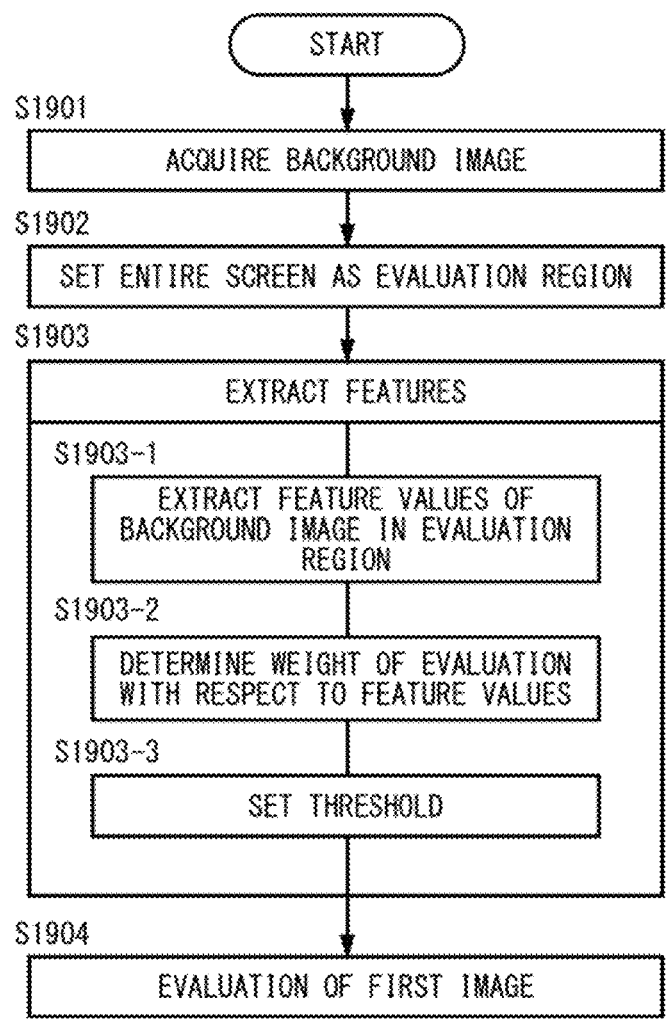
FIG. 19 is a flowchart for explaining a procedure of one-point registration for registering a non-defective product image or a background image.

Further, a procedure of the one-point registration for registering a non-defective product image or a background image is explained with reference to FIG. 19. First, in step S1901, the image processing sensor acquires a background image. For example, the image processing sensor acquires the background image BGI shown in FIG. 20 and saves the background image BGI in the image storing unit 54*i*. Note that the background image may be reduce in resolution on the basis of a response time set in advance as explained below.

Subsequently, in step S1902, the image processing sensor sets the entire screen as an evaluation region. For example, an evaluation region EVD is automatically set with respect to the background image BGI shown in FIG. 20 as indicated by a frame in FIG. 21.

Further, in step S1903, the image processing sensor extracts feature values. Specifically, first, in step S1903-1, the image processing sensor extracts feature values of the background image BGI in the evaluation region EVD. For example, feature values such as the number of edges of 0 and a luminance average of 70 are obtained with respect to the background image BGI shown in FIG. 21.

Subsequently, in step S1903-2, the image processing sensor determines weighting of an evaluation with respect to the feature values. For example, the image processing sensor selects 50% of the number of edges and 50% of the luminance average is selected as feature values of the pass/fail determination.

Further, in step S1903-3, the image processing sensor sets a matching degree threshold. The image processing sensor automatically sets the matching degree threshold with respect to, for example, the number of edges and the luminance average.

When the setting mode ends in this way, the image processing sensor shifts to the operation mode. In the operation mode, in step S1904, the image processing sensor performs an evaluation of an input image. Note that the image processing sensor does not perform processing such as specifying of work and cutout of work and regards the entire screen as one work and performs distinction processing.

(Desirable Registration State)

In registering an image in the image/setting storing unit 54 in the setting mode, the image processing sensor performs the registration under desirable registration setting conditions. The desirable registration setting conditions are conditions under which, when the pass/fail determining unit 57*d* performs the pass/fail determination in the operation mode, the pass/fail determining unit 57*d* can stably distinguish a non-defective product and a defective product. In the determination, it is important how the non-defective product and the defective product can be stably distinguished. In the operation mode, the pass/fail determining unit 57*d* performs the pass/fail determination using, as an evaluation value, a matching degree of an input live image and a non-defective product image. As a matching degree calculated by the matching-degree calculating unit 57*c* with respect to the input live image, an evaluation value of 0% to 100% is calculated. When the input live image is a non-defective product image obtained by imaging a non-defective product, a matching degree of the input live image is ideally calculated as 100%. However, when the input live image is a defective product image obtained by imaging a defective product, in general, a matching degree is not 0%. This is because, since a part of the non-defective product image is different depending on a chip, a crack, and the like, the defective product image often includes a portion coinciding with the non-defective product image.

(Matching Degree Threshold)

A matching degree threshold serving as a reference of the pass/fail determination is determined on the basis of a matching degree of a defective product and a matching degree of a non-defective product. For example, the threshold calculating unit sets, as the matching degree threshold, an intermediate value between the matching degree of the non-defective product, which is generally high, and the matching degree of the defective product, which is generally low. In order to stably distinguish the non-defective product and the defective product, that is, stabilize a determination result, it is desirable to separate the matching degree of the non-defective product and the matching degree of the defective product as much as possible such that a difference between the matching degrees is large. Therefore, under a condition in which dispersion of the matching degree with respect to the non-defective product can be regarded as constant, the matching degree of the non-defective product and the matching degree of the defective product are separated such that the difference between the matching degrees is larger as the matching degree of the defective product is calculated lower. Stable pass/fail determination can be expected. Therefore, a registration state is considered to be good. Accordingly, it is necessary to calculate brightness and resolution of an image to be captured and conditions of image processing such that the non-defective product and the defective product are separated and a stable determination result is obtained. Consequently, it is possible to appropriately set the matching degree threshold serving as the reference of the pass/fail determination.

Note that the matching-degree calculating unit 57c and the threshold calculating unit 56c are shown as the separate members in the example shown in the block diagram of FIG. 5. However, the present invention is not limited to this configuration. For example, the matching-degree calculating unit and the threshold calculating unit may be configured by the same member.

(Method in which the Threshold Calculating Unit Sets the Matching Degree Threshold)

The setting of the matching degree threshold serving as the reference of the pass/fail determination is performed by the threshold calculating unit 56c. The threshold calculating unit 56c sets the matching degree threshold between a matching degree of a defective product image and a matching degree of a non-defective product image calculated by the matching-degree calculating unit 57c. The matching degree threshold is desirably set in the middle of the matching degrees of the non-defective product image and the defective product image. As an example, an example in which, when the matching degree of the non-defective product image is set to 100%, the matching degree threshold is set according to the matching degree of the defective product image is shown in a table of FIG. 22. For example, when the matching degree of the defective product image is 80%, the matching degree threshold is set to (100%+80%)/2=90%. Similarly, when the matching degree of the defective product image is 70%, the matching degree threshold is set to (100%+70%)/2=85%. When the matching degree of the defective product image is 60%, the matching degree threshold is set to (100%+60%)/2=80%. When the matching degree of the defective product image is 50%, the matching degree threshold is set to (100%+50%)/2=75%.

In this way, it is considered that, as the matching degree of the defective product image is lower, the non-defective product image and the defective product image are further separated and stability of the pass/fail determination is improved. Therefore, in registration of an image in the image/setting storing unit 54, the aim is to achieve an image registration state in which the matching degree of the defective product image is low in this way. In an example shown in FIG. 22, the lowest matching degree threshold of 50% is desirable because the difference between the matching degrees of the non-defective product image and the defective product image is the largest.

(Determination of Feature Values During Registration)

On the other hand, when the pass/fail determination is performed with only feature values in which a difference in the matching degree threshold is the lowest, erroneous determination is sometimes performed in a specific case. For example, in feature values A to D in which the matching degrees of the non-defective product image and the defective product image indicate values shown in Table 1, the feature value D is considered to be desirable because a difference between the matching degrees of the non-defective product image and the defective product image is the largest. However, specific noise resistance is sometimes deteriorated.

TABLE 1

|  | Non-defective product image | Defective product image |
| --- | --- | --- |
| Feature value A | 100 | 60 |
| Feature value B | 100 | 90 |
| Feature value C | 100 | 100 |
| Feature value D | 100 | 50 |

Therefore, it is possible to stabilize a non-defective product determination result by, rather than performing the pass/fail determination with one feature value, performing an evaluation of the pass/fail determination taking into account other feature values. For example, in the case of Table 1, the pass/fail determination is not performed with only the feature value D. The other feature values A and B with which the non-defective product and the defective product can be distinguished are also evaluated.

(Weighting Setting Unit 56e)

The image processing sensor can also include a weighting setting unit 56e for setting, in the setting mode, according to a matching degree of each of a plurality of different image processing algorithms, for each of the image processing algorithms, weighting used in calculating the matching degree threshold with the threshold calculating unit 56c.

In order to perform an evaluation in which a plurality of feature values are combined in this way, for example, weighting is performed on the plurality of feature values. The weighting is set larger for the feature values in which the difference between the matching degrees of the non-defective product and the defective product is larger. Conversely, the weighting is set smaller for the feature values in which the difference between the matching degrees is smaller. For example, in an example shown in Table 1, weighting of 40% is performed with respect to the feature value A, weighting of 10% is performed with respect to the feature value B, weighting of 0% is performed with respect to the feature value C, and weighting of 50% is performed with respect to the feature value D. In this case, the feature value C has the weighting of 0%. Even if the feature value C is calculated, the feature value C is not evaluated. Therefore, processing of the feature value C does not have to be performed during execution of the evaluation of the pass/fail determination. In this way, the weighting setting unit 56e is configured to, for example, set large weighting with respect to a processing flow with a low image matching degree calculated by the matching-degree calculating unit 57c and, conversely, set small weighting with respect to a processing flow with a high image matching degree. When the image matching degree is low, separability of the non-defective product and the defective product is considered to be excellent. Therefore, the weighting is increased. Conversely, when the image matching degree is high, the separability of the non-defective product and the defective product is considered to be inferior. Therefore, it is possible to improve the accuracy of the pass/fail determination as a whole by adjusting to reduce the weighting.

Note that, in the example shown in FIG. 5, the calculation of the matching degree is performed by the matching-degree calculating unit 57c in both of the setting mode and the operation mode. In the setting mode, after performing, with the setting-image processing unit 56, image registration operation, the image processing sensor operates the operation-image processing unit 57 to calculate matching degrees of the non-defective product and the defective product with the matching-degree calculating unit 57c. The image processing sensor calculates a threshold from a result of the calculation of the matching degrees. On the other hand, in the operation mode, the matching-degree calculating unit 57c calculates a matching degree with respect to an input image on the basis of the weighting calculated during the setting. In this case, the matching-degree calculating unit 57c calculates a weighted addition matching degree obtained by adding the weighting set by the weighting setting unit 56e to the image matching degrees calculated for each of a plurality of different processing flows. For example, a final score of a matching degree in evaluating the feature values A to D shown in Table 1 with the weighting explained above can be calculated by (a score of the feature value A)×(weight of the feature value A)+(a score of the feature value B)×(weight of the feature value B)+(a score of the feature value C)×(weight of the feature value C)+(a score of the feature value D)×(weight of the feature value D).

Further, in the operation mode, when the image matching degree calculated by the matching-degree calculating unit 57c reaches a predetermined prohibition threshold, the execution of the processing flow may be prohibited.

(Guide Lines GDL)

In the example shown in FIG. 16 and the like, the guide lines GDL serving as the indicators for positioning of work are shown in the image display region PD. The guide lines GDL are displayed in a frame shape surrounding four corners in an L shape. In this way, it is possible to urge the user to perform positioning to arrange, for example, in work, which is an inspection target object, characteristic portions such as parts where signs of a defective product appear are included in the frames of the guide lines GDL. In other words, an effect of causing the user to be aware that an important image is arranged near the center is obtained. As a result, an evaluation with weight added to a feature difference is expected. It is possible to stably perform determination of a matching degree and obtain a determination result with high reliability. The guide lines GDL are not limited to such a frame shape. It is possible to appropriately adopt other forms such as display for inducing the user to arrange work in the center, for example, forming the guide lines GDL as cross lines or target shapes passing the center of the image display region PD. Note that ON/OFF of the display of the guide lines GDL may be capable of being switched.

Figure 23:
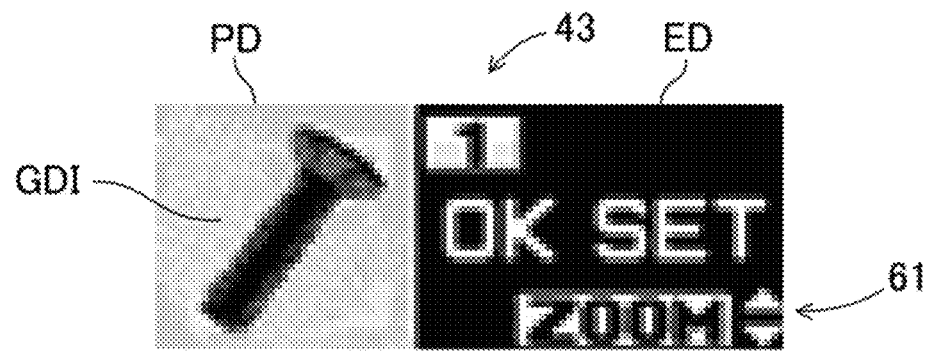
FIG. 23 is an image diagram showing another example of the first registration screen during the two-point registration.
Figure 24:
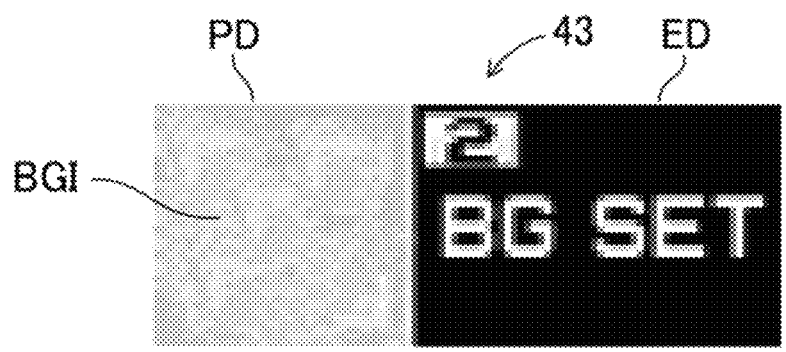
FIG. 24 is an image diagram showing another example of the second registration screen during the two-point registration.

Note that, in the example shown in FIGS. 9 and 13, the character information is displayed in two rows as the first registration induction information. However, the character information may be displayed in one row. Such an example is shown in FIGS. 23 and 24. In FIG. 23, "OK SET" is displayed in the explanation display region ED as the first registration induction information for registering the non-defective product image GDI on the first registration screen. In FIG. 24, "BG SET" is displayed in the explanation display region ED as the second registration induction information for registering the background image BGI on the second registration screen.

(Registration Order Information 63)

Further, the registration order information 63 indicating registration order may be included as registration induction information. For example, "1" is displayed on the first registration screen shown in FIG. 23 and "2" is displayed on the second registration screen shown in FIG. 24. The user can visually grasp a stage of image registration from these displays. In this way, not only character strings but also numbers can be used as the registration induction information. The numbers may indicate types of display screens other than registration order of images. For example, "1" may be displayed on the first registration screen, "2" may be displayed on the second registration screen, and "3" may be displayed on the third registration screen.

(Induction Information)

Figure 25:
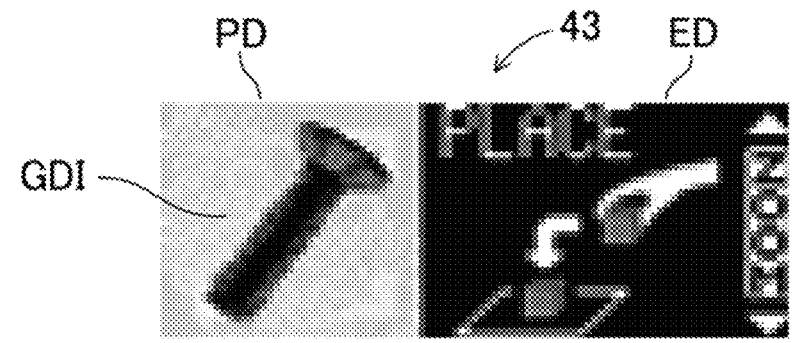
FIG. 25 is an image diagram showing still another example of the first registration screen during the two-point registration.
Figure 26:
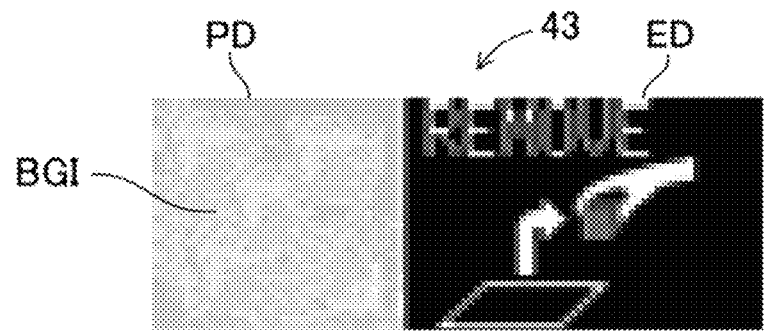
FIG. 26 is an image diagram showing still another example of the second registration screen during the two-point registration.

In the example explained above, the display control unit 58f causes the display unit 43 to display the character information as the induction information. However, the present invention is not limited to guidance by characters. The user can also be induced to follow a procedure of registration in another form such as figures, sound, a combination of the figures and the sound, or the like. An example in which a figure is combined with characters to perform a registration instruction is shown in FIGS. 25 and 26. In FIG. 25, a state in which work is placed in the screen visual field is indicated by a figure as the first registration induction information for instructing registration in a "detected work is present" state. FIG. 25 corresponds to FIGS. 9 and 23 referred to above. In the figure, the "ZOOM" icon may be displayed as the enlargement and reduction possible display information in the explanation display region ED in order to indicate that enlargement and reduction display of a live image displayed in a display region is possible. Such enlargement and reduction possible display information is not limited to be written horizontally as in the example shown in FIG. 9 and can be indicated by vertical writing as shown in FIG. 25. Consequently, it is possible to effectively utilize the display region having a limited area.

In FIG. 26, a state in which the work is removed from the imaging position is indicated by a figure as the second registration induction information for instructing registration in a "detected work is absent" state. FIG. 26 corresponds to FIG. 13 and the like. By displaying the figure on the display unit 43 in this way, it is possible visually instruct a motion that should be performed and provide an operation environment easily understood by the user unaccustomed to operation. The figure is not limited to a still image and can also be displayed as a moving image. For example, by displaying, as a moving image or an animation, a state in which the work is placed by a hand or a state in which the work is removed by the hand, it is possible to more clearly instruct the user about operation that should be performed.

(Display Switching)

Figure 27:
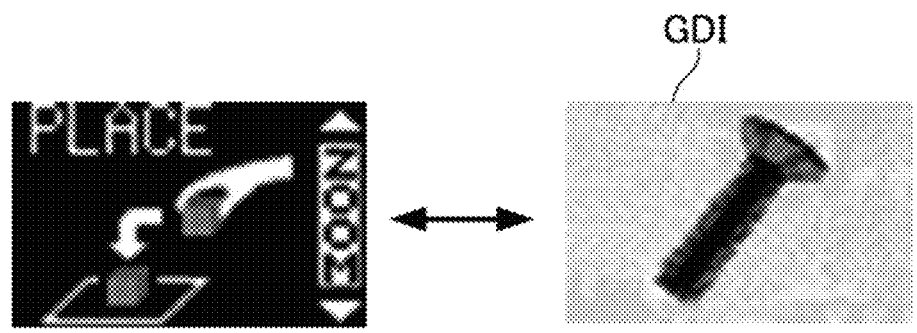
FIG. 27 is an image diagram showing an example in which the first registration screen is switched and displayed.
Figure 28:
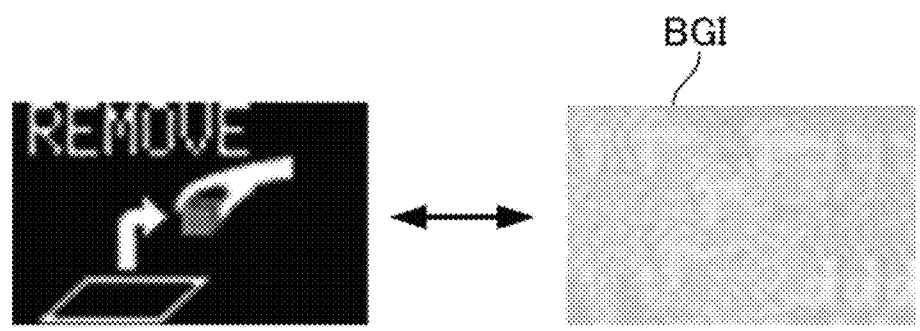
FIG. 28 is an image diagram showing an example in which the second registration screen is switched and displayed.
Figure 29:
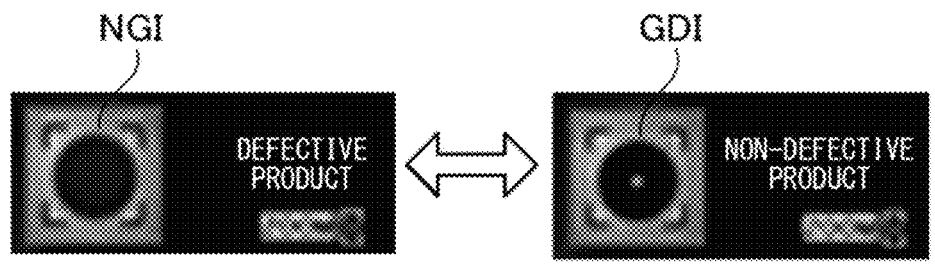
FIG. 29 is an image diagram showing an example in which candidate images about to be registered and registered non-defective product images are switched and displayed on the second registration screen.
Figure 30:
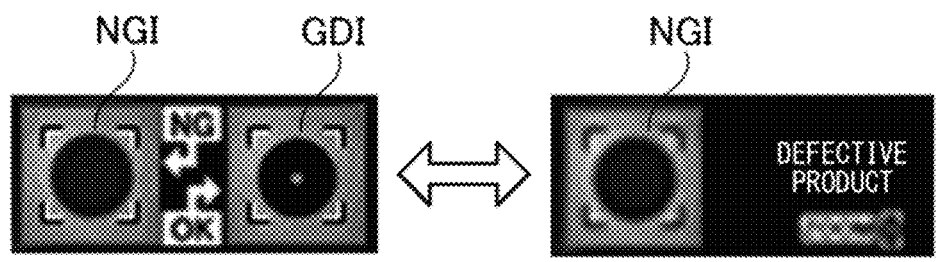
FIG. 30 is an image diagram showing an example in which the candidate images about to be registered and parallel display are switched and displayed on the second registration screen.

Further, the display unit 43 may be capable of switching and displaying a plurality of display screens. For example, in the example shown in FIGS. 25 and 26, the image display region PD and the explanation display region ED are simultaneously displayed on one screen. However, as shown in FIGS. 27 and 28, the image display region PD and the explanation display region ED can also be switched and displayed. Alternatively, not only the image display region PD and the explanation display region ED but also images may be switched and displayed. For example, as shown in FIG. 29, candidate images about to be registered and the non-defective product image GDI already registered are switched and displayed on the second registration screen. Consequently, explanations can be displayed together with the images. Therefore, it is easier to grasp what is displayed by which image. Further, by switching and displaying the images, it is also possible to compare both the images. Alternatively, as shown in FIG. 30, in the second registration screen, the candidate images about to be registered and parallel display explained below (the non-defective product image GDI and the candidate images) can also be switched and displayed. In this way, the limited display area of the display unit 43 can be more effectively utilized. In particular, when the display area of the display unit 43 is narrow, it is possible to avoid a problem in that displayed images and characters are small and the display unit 43 having high resolution needs to be prepared. As the switching of the screens, displays can be automatically alternately switched at a fixed cycle. Alternatively, besides such an automatic alternate display function, the user may operate a switching button or the like to manually perform the switching of the screens.

(Parallel Display Function)

Figure 31:
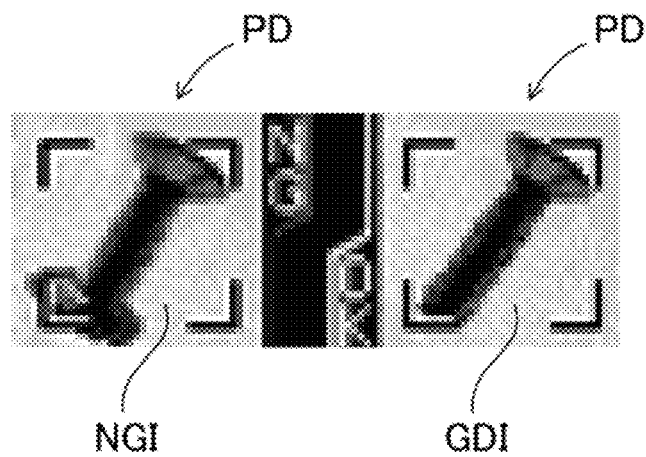
FIG. 31 is an image diagram showing an example in which the second registration screen during the three-point registration is a parallel display screen.

In the two-point registration and the three-point registration, a plurality of images can also be displayed side by side on one screen. For example, after one image is registered in the setting mode, when the other image is registered, the registered image is displayed as a still image and the image being currently registered is displayed as a live image. An example of such parallel display is shown in FIG. 31. The figure shows the second registration screen of the two-point registration. It is assumed that the non-defective product image GDI is registered as the first image in advance on the first registration screen of the two-point registration. In this state, on the second registration screen on which the defective product image NGI is registered as the second image, as shown in FIG. 31, a first image display region PD for displaying the first image and a second display image region PD for displaying the second image are provided in the image display region PD of the display unit 43. Consequently, the user can register the defective product image NGI while taking into account the registered non-defective product image GDI. Such a second registration screen can be used instead of the second registration screen shown in FIGS. 11 and 13 and the like. Such a parallel display function can also be applied not only to the second registration screen but also to the third registration screen.

(Still Image/Live Image Simultaneous Display Function)

Further, in the parallel display, it is also possible to display a part of images as a still image and display the other image as a live image. That is, by displaying, as a live image, an image about to be registered while displaying a registered image as a still image, it is easy to adjust, which checking, on a real-time basis, a state in which the position of work, illumination, and the like are changed, the state to an optimum state. For example, in the example shown in FIG. 31, the non-defective product image GDI serving as the first image is displayed as a still image in the first image display region PD on the right side. A live image of the defective product image NGI registered as the second image is displayed in the second image display region PD on the left side. The user can adjust a placing method while viewing the non-defective product image GDI on the right side such that the posture, the size, and the like of the defective produce coincide with the posture, the size, and the like of the non-defective product image GDI. A light amount of illumination and the like can also be adjusted. Consequently, the non-defective product image GDI and the defective product image NGI can be registered such that the same portions are easily matched, in other words, in a state in which differences easily become distinct when a difference is extracted. Therefore, it is easy to more highly accurately calculate a matching degree. This is also advantageous in setting a matching degree threshold for distinguishing the non-defective product image GDI and the defective product image NGI. The non-defective product image GDI already registered is also displayed. Therefore, the user can check whether the non-defective product image GDI registered earlier is correctly registered. For example, when an unintended cut or the like of a background with respect to the non-defective product image occurs, the user can notice the cut or the like and can determine to perform imaging again. Further, by displaying the non-defective product image GDI and the defective product image NGI side by side on the screen of the display unit 43, it is possible to compare the non-defective product image GDI and the defective product image NGI and determine as what kind of a difference an actual object of work is reflected on the screen. By enabling the user to be aware of a state of the registered image in which way, it is possible to easily create a satisfactory registration state, leading to stabilization of detection.

Figure 32:
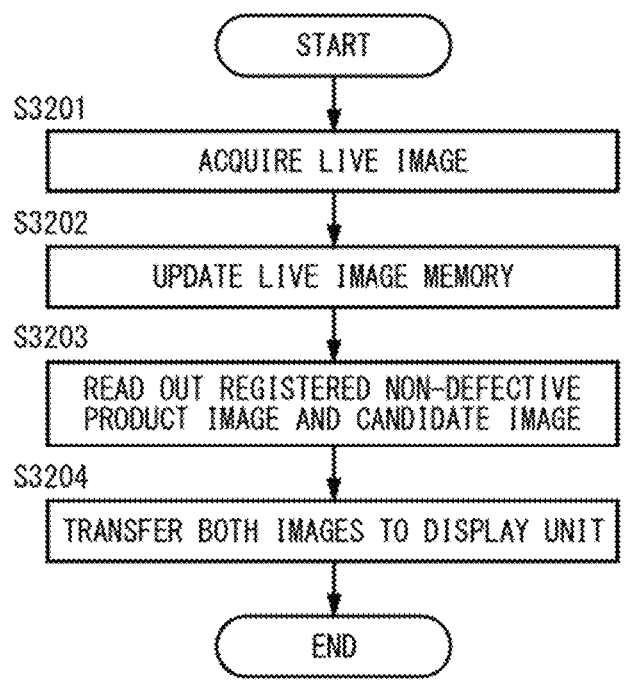
FIG. 32 is a flowchart for explaining a procedure of still image/live image simultaneous display.

An example of a procedure for realizing such a still image/live image simultaneously display function is shown in a flowchart of FIG. 32. The flowchart corresponds to a detailed flow of step S608 in the two-point registration shown in FIG. 6. First, in step S3201, the image processing sensor acquires a live image. The image processing sensor captures, with the imaging unit 21, as the second image, a live image of an optical image serving as a candidate of a defective-product image. Subsequently, in step S3202, the image processing sensor updates content of a memory that retains the live image. Specifically, the image processing sensor overwrites data of a live image captured last time and stored in the live image memory with data of the live image acquired anew and saves the data. Note that the memory may be a dedicated memory for the live image or may be a common memory. Subsequently, in step S3203, the image processing sensor reads out the saved live image and the non-defective product image already registered on the first registration screen. In step S3204, the image processing sensor transfers the images to the display screen. The image processing sensor causes the display unit 43 to display the non-defective product image as a still image and display the candidate of the defective product image as a live image on the second registration screen. Thereafter, the image processing sensor repeats these steps and realizes real-time display for updating display content of the display unit 43. In this way, the image processing sensor adjusts a position where defective work is placed, the posture of the defective work, and the like while, in registering the defective product image, displaying the defective product image as the live image and taking into account the non-defective product image of the still image to make it possible to check an image after the adjustment on the display unit 43 on a real time basis. Consequently, an environment in which registration work of a desired image can be easily performed is provided.

In the example explained above, the non-defective product image registered on the first registration screen is displayed as the still image on the second registration screen and the defective product image is displayed as the live image. However, the present invention is not limited to this configuration. For example, it is also possible to display, on the second registration screen, as still image, the non-defective product image registered on the first registration screen and display the background image as the live image. Conversely, it is also possible to register the background image and the defective product image on the first registration screen and display and register the non-defective production image as the live image while displaying the registered images as still image on the second registration screen. Further, the still image/live image simultaneous display function can be used not only in the two-point registration but also in the three-point registration. That is, it is also possible to display, as the still image on the second registration screen, the non-defective product image registered on the first registration screen, display the defective product image as the live image, and display the background image as the live image while displaying the non-defective product image as the still image on the third registration screen as well. Alternatively, it is also possible to display the background image as the live image while displaying the defective product image as the sill image on the third registration screen.

Alternatively, in the three-point registration, the parallel display and the still image/live image simultaneously display may be combined with independent display. For example, when the defective product image is registered on the second registration screen, the parallel display of the non-defective product image of the still image and the defective product candidate images of the live image is performed. When the non-defective product image is registered on the first registration screen and when the background image is registered on the third registration screen, independent image display is performed. In particular, in general, it is often sufficient to capture the background image as it is. Therefore, simplification of the processing is achieved by eliminating the need for the parallel display.

Figure 33:
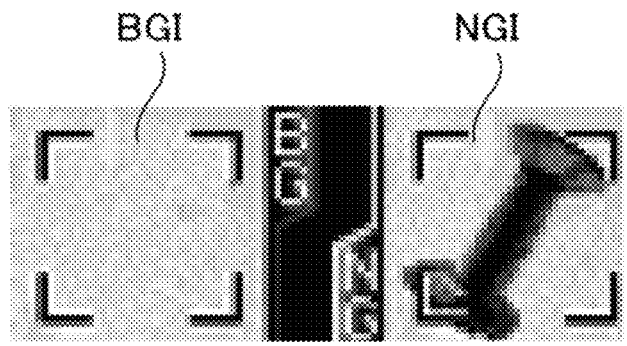
FIG. 33 is an image diagram showing an example in which the third registration screen during the three-point registration is a parallel display screen.

As such a parallel display screen, for example, a registered image and a current live image are displayed side by side. As an example, the display unit 43 shown in FIG. 31 displays the registered non-defective product image GDI (an OK image) and the current live image (an NG image) serving as a candidate of the defective product image NGI side by side. In this case, the normal registration screen and the parallel display screen may be switched and displayed. For example, in the three-point registration, the second registration screen shown in FIG. 17 and the parallel display screen shown in FIG. 31 can be switched and displayed. Consequently, in the registration of the defective product image, it is possible to register the defective product image while comparing the defective product image with the non-defective product image. Similarly, in the registration of the background image, for example, when the third registration screen shown in FIG. 18 is displayed, the third registration screen and a parallel display screen shown in FIG. 33, on which the registered defective product image NGI and an image (a still image or a live image) currently being registered serving as a candidate of the back ground image BGI are displayed side by side, may be switched and displayed. Alternatively, the parallel display screen may be a combination of the non-defective product image and the background image rather than the combination of the defective product image and the background image. Further, the parallel display screen is not limited to the configuration in which the two images are displayed in parallel. Three or more images may be displayed on one screen.

Figure 34:
FIG. 34 is an image diagram showing an example in which an image display region and an explanation display region are caused to partially overlap.
Figure 35:
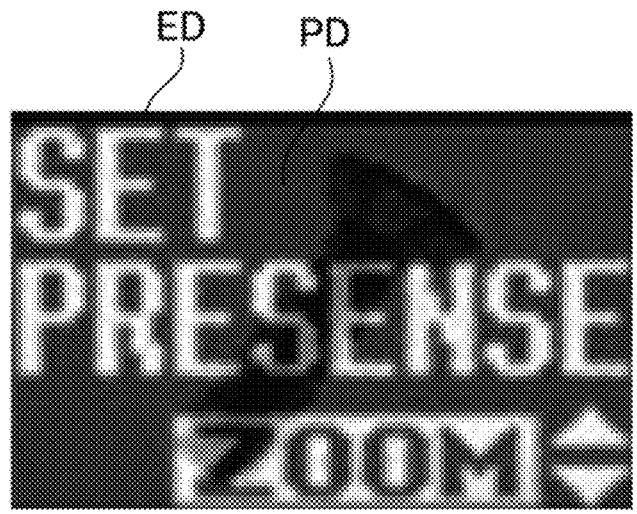
FIG. 35 is an image diagram showing an example in which the image display region and the explanation display region are caused to completely overlap.

Note that, in the example explained above, the image display region PD and the explanation display region ED are divided. However, the image display region PD and the explanation display region ED may be partially superimposed and displayed or may be caused to overlap. For example, in an example shown in FIG. 34, the image display region PD and the explanation display region ED are caused to partially overlap to display character information, which is the first registration induction information. Alternatively, as shown in FIG. 35, the image display region PD and the explanation display region ED may be caused to completely overlap to display the character information. It is also possible to integrate the image display region and the explanation display region without distinguishing the regions and incorporate and display the first registration induction information in display of an image. In this way, it is possible to effectively utilize a limited region of the display unit. Therefore, in this embodiment, it is not always necessary to exclusively provide the image display region and the explanation display region and clearly mark off a boundary. This embodiment includes a form in which character information is superimposed on an image by, for example, arranging the image display region and the explanation display region to partially or entirely overlap or integrating the image display region and the explanation display region.

Note that, in these examples, the character string and the icon on the display unit are written in English. However, a language is not limited to English. It goes without saying that the character string and the icon may be written in Japanese and other languages.

In this way, the user is guided to proceed with the setting work in the setting mode according to the depression of the SET key 42. Therefore, there is an excellent convenience that even a beginner not understanding the operation principle and the like of the image processing sensor can easily use the image processing sensor. In particular, in the image sensor in the past, the setting registration is complicated and, on the other hand, the registration work is completed by simply performing SET key operation twice in a state in which work is present and a state in which work is absent. Therefore, there is a large difference in difficulty of setting between the photoelectric sensor in the past and the image sensor. There are many users who can perform setting in the photoelectric sensor in the past but cannot perform setting of the image sensor. On the other hand, in the image sensor according to this embodiment, the user can perform the setting of the image processing sensor in feeling same as feeling of setting the photoelectric sensor. Therefore, it is possible to mitigate a barrier in introducing the image processing sensor.

(Operation Mode)

When the setting of the matching degree threshold with respect to the image matching degree ends as explained above, it is possible to shift the image processing sensor from the setting mode to the operation mode. In the operation mode, the image processing sensor captures an image of work actually conveyed on a conveyance line, calculates a matching degree with respect to an obtained input image, and compares the matching degree with the matching degree threshold to perform determination of a non-defective product and a defective product.

(A Selecting Function for a Distinction Target and an Operation Principle)

A selecting function for a distinction target and an operation principle are explained with reference to FIGS. 55, 56, and 57. FIG. 55 is an image diagram showing a state in which non-defective work WK and defective work WK are flowing on a manufacturing line. As shown in FIG. 55, a detection region of the image processing sensor 100 has width. A spot diameter of the image processing sensor 100 is, for example, as a large size, approximately 6 cm×6 cm and, as a small size, approximately 2 mm×2 mm. In view of the fact that a spot diameter of a normal photoelectric sensor is approximately 1.2 mmφ, the spot diameter of the image processing sensor 100 is considered to be larger than the spot diameter of the normal photoelectric sensor.

Figure 56A:
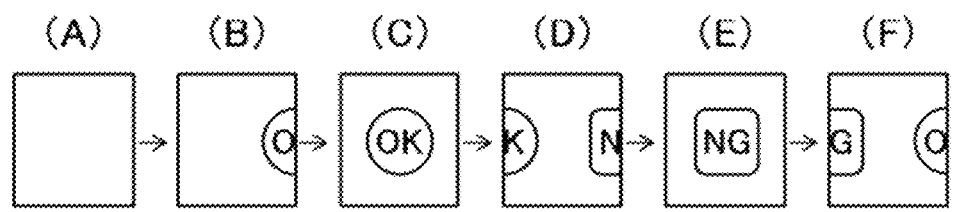
FIG. 56A is a schematic diagram of showing a flow of work for explaining an output state at the time when a master image is a non-defective product image.
Figure 56B:
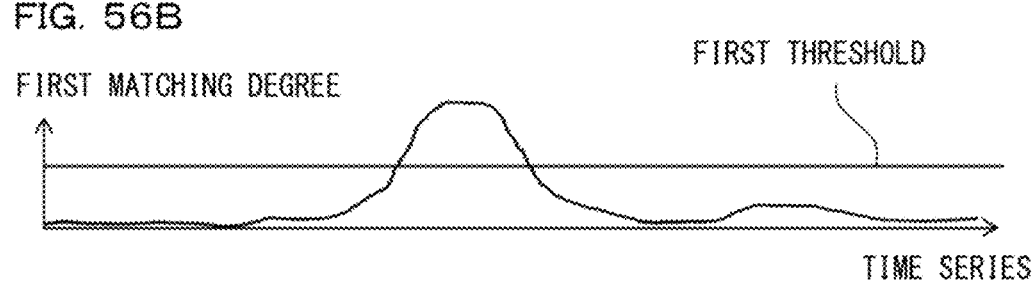
FIG. 56B is a graph showing a time series change of a first matching degree.
Figure 56C:
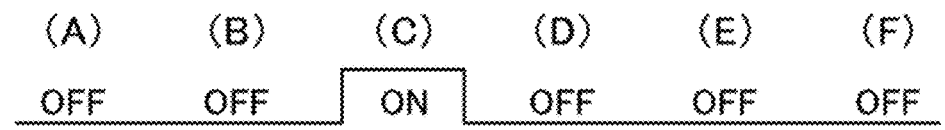
FIG. 56O is a schematic diagram showing a time series change of an output.
FIG. 56D is a schematic diagram showing a time series change of an output at the time when setting for reversing an output logic with respect to the time series change of the output shown in FIG. 56C or changing the output to ON when the matching degree is smaller than a threshold.

Therefore, in the detection region imaged by the imaging unit 52, for example, as shown in FIG. 56A, the work WK change in the order of (A) to (F). At this point, in a normal operation state, that is, when a master image is a non-defective product image, as shown in FIG. 56B, which is an image diagram of a time-series change of a first matching degree, the first matching degree gradually increases from the periphery of (B), reaches a peak at a point in time of (C), and gradually decreases in (D). A slight increase of the first matching degree in (E) means that elements coinciding with features of the non-defective product image are present in a defective product image. An image diagram showing an output state in this case is shown in FIG. 56C. As shown in the figure, an output is turned on when the first matching degree exceeds the first threshold. That is, the output is turned on only when the non-defective work WK comes.

Figure 56D:
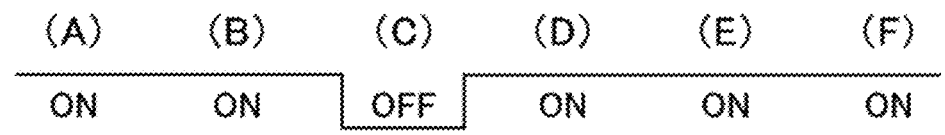

A time-series change of the output at the time when setting for inverting an output logic like, for example, a negative output of the photoelectric sensor or turning on the output when the matching degree is smaller than a threshold is performed on the time-series change of the output shown in FIG. 56C is shown in FIG. 56D. As shown in the figure, in all the cases, (1) a state in which the work WK is absent in the detection region (a state of (A)) or a state in which the work WK enters the detection region halfway (states of (B), (D), and (F)) and (2) a state in which the defective work WK comes (a state of (E)) cannot be separated by outputs.

Therefore, in order to recognize that the defective work' WK enters the detection region, it is necessary to notify the sensor with another means that "the work WK enters the detection region and it is timing to perform determination" (the states of (C) and (E)). That is, if "it is timing to perform determination" and "the determination output is OFF", it is possible to recognize that the defective product WK comes.

Figure 57A:
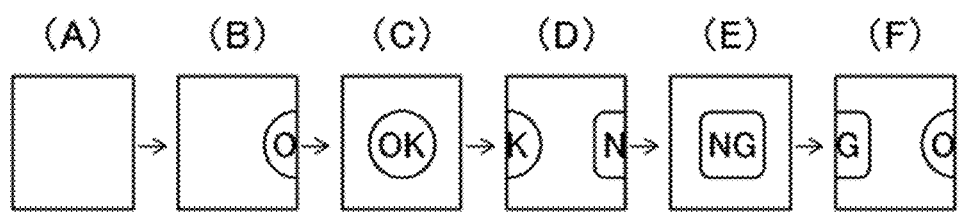
FIG. 57A is a schematic diagram showing a flow of work for explaining an output state at the time when the master image is a defective product image.
Figure 57B:
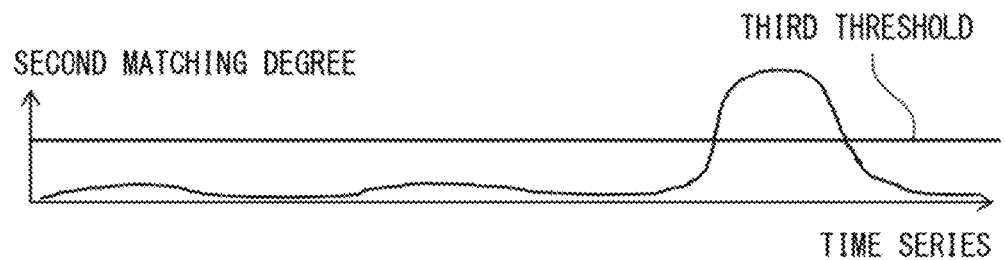
FIG. 57B is a graph showing a time series change of a second matching degree.
Figure 57C:
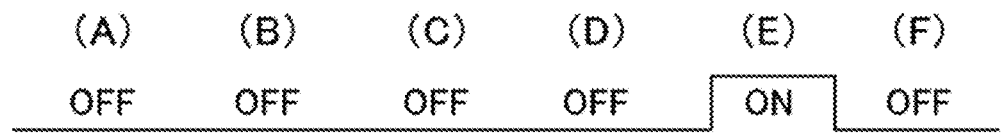
FIG. 57C is a schematic diagram showing a time series change of an output.

When setting for causing the defective product image to operate as the master image is selected, a time-series change of the second matching degree shown in FIG. 57B and a time-series change of the output shown in FIG. 57C are obtained with respect to, for example, the flow of the work WK that changes in the order of (A) to (F) shown in FIG. 57.

That is, during the defective product output setting, the second matching degree gradually increases from the periphery of (D), reaches a peak at a point in time (E), and gradually decreases in (F). In this case, as shown in FIG. 57C, when the second matching degree exceeds the third threshold, the output is turned on. That is, the output is turned on only when the defective work comes.

When the setting for causing the defective product image to operate as the master image is selected in this way, it is possible to perform control for discharging the defective product using the output as a trigger. The image processing sensor 100 according to this embodiment can select whether to cause the non-defective product image to operate as the master image or to cause the defective product image to operate as the master image. Therefore, the image processing sensor 100 is capable of coping with, with one setting change, both of a user who performs discharge control and the like when the defective product comes (a user who desires to learn that the defective product comes) and a user who performs counting and the like when the non-defective product comes (a user who desires to learn that the non-defective product comes).

For example, when a desired determination result is not obtained according to the determination result in the operation mode or when the user desires to adjusts the setting to setting further improved in accuracy, it is possible to shift to the setting mode again and perform update of the setting. Alternatively, during the operation mode, it is also possible to temporarily change registration setting conditions. For example, the matching degree threshold is finely adjusted according to a result of the pass/fail determination (details are explained below).

Figure 36:
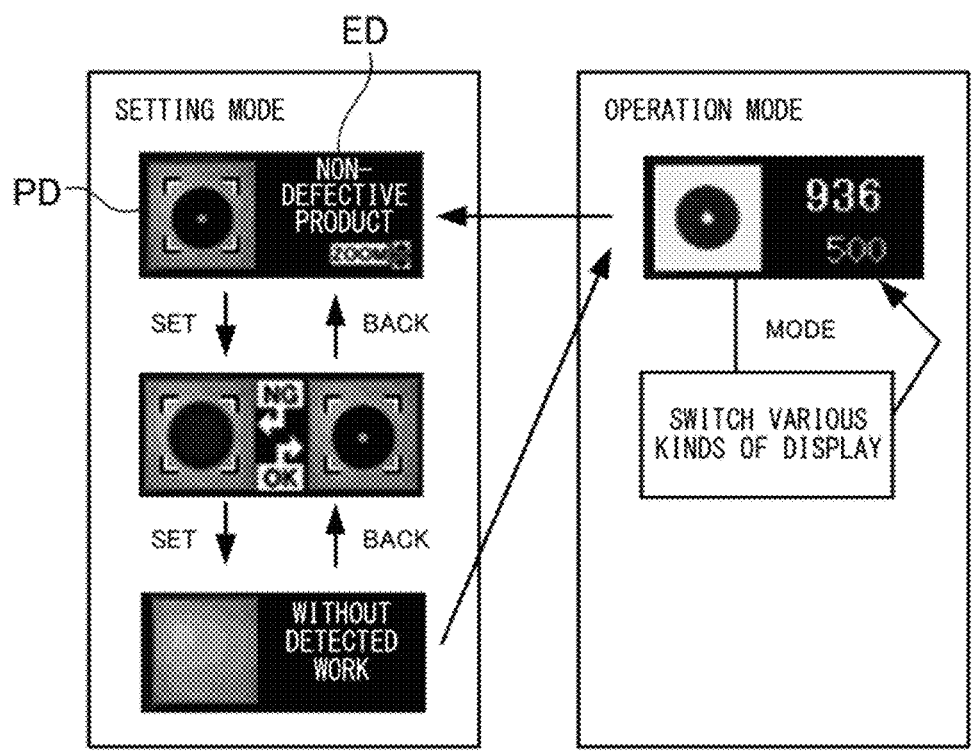
FIG. 36 is a schematic diagram showing a state in which an operation mode and a setting mode are switched.

Such switching of the operation mode and the setting mode is performed from the operation/setting-mode switching unit 51d. As an example of the operation/setting-mode switching unit 51d, the SET key 42 is used in the image processing sensor shown in FIG. 3A and the like. As shown in FIG. 36, it is possible to switch the operation mode and the setting mode by depressing the SET key 42. For example, in the setting mode explained above, when the SET key 42 is depressed in a state in which registration of a necessary image ends, the setting mode is switched to the operation mode. In the setting mode, the SET key 42 is used in order to instruct screen transition to, for example, shift the first registration screen to the second registration screen. It is possible switch the setting mode to the operation mode by depressing the SET key 42 at a stage when final setting ends. In this way, means for screen transition in the setting mode and switching means from the setting mode to the operation mode are set as common operation, that is, the depression of the SET key 42. Therefore, the user can perform necessary setting by repeating work for pressing the SET key 42 and perform the switching from the setting mode to the operation mode. Smooth setting work is realized. Further, the switching from the setting mode to the operation mode can be performed in common with final work in the setting mode. For example, in the three-point registration shown in FIG. 36, the SET key 42 is depressed on the first registration screen to register the non-defective product image, the SET key 42 is depressed on the second registration screen to register the defective product image, the SET key 42 is depressed on the third registration screen to register the background image. The switching work from the setting mode to the operation mode is simultaneously executed. Consequently, the setting mode is automatically switched to the operation mode after the necessary setting ends. Therefore, the user can smoothly perform the switching from the setting work to the operation mode without being confused.

(Operation Mode Screen)

On the operation mode screen displayed on the display unit 43 in the operation mode, the image display region PD and the explanation display region ED are provided. In the example shown in FIG. 36, the image display region PD is disposed on the left side of the display unit 43 and the explanation display region ED is disposed on the right side.

(Common Position Display Function)

As display content of the display unit 43, layouts of the image display region PD and the explanation display region ED are desirably used in common in the setting mode and the operation mode. In particular, when a region where an image is displayed is set in a common position in the setting mode and the operation mode, the user can check the image without being confused. More specifically, when a region where a live image is displayed is fixed in a fixed position, the user can easily grasp which image is a target image. In the example shown in FIG. 36, in both of the setting mode and the operation mode, the image display region PD is fixed on the left side of the display unit 43. In this way, a relative positional relation is used in common during the setting and during the operation. Therefore, it is possible to give security of operation to the user. On the second registration screen, the registered first image and the live image serving as the candidate of the second image are displayed on one screen. However, if the live image is fixed on the left side, the user can recognize that the live image of the registration target is on the left side of the common position and is less confused about which image is an image that should be registered.

The matching degree and the matching degree threshold are displayed on the operation mode screen. Consequently, the user can check, on one screen, a matching degree of an input image of sequentially imaged work and a non-defective product image calculated in the image and a matching degree threshold set in the setting mode.

A result of the pass/fail determination is output to the outside. For example, a signal indicating the determination result such as an OK signal or an NG signal is transmitted. The determination result may be displayed on the outside. For example, the determination-result display lamp 41 provided on the display surface 40*a* of the image processing sensor shown in FIG. 3A and the like is lit according to the determination result.

Figure 37A:
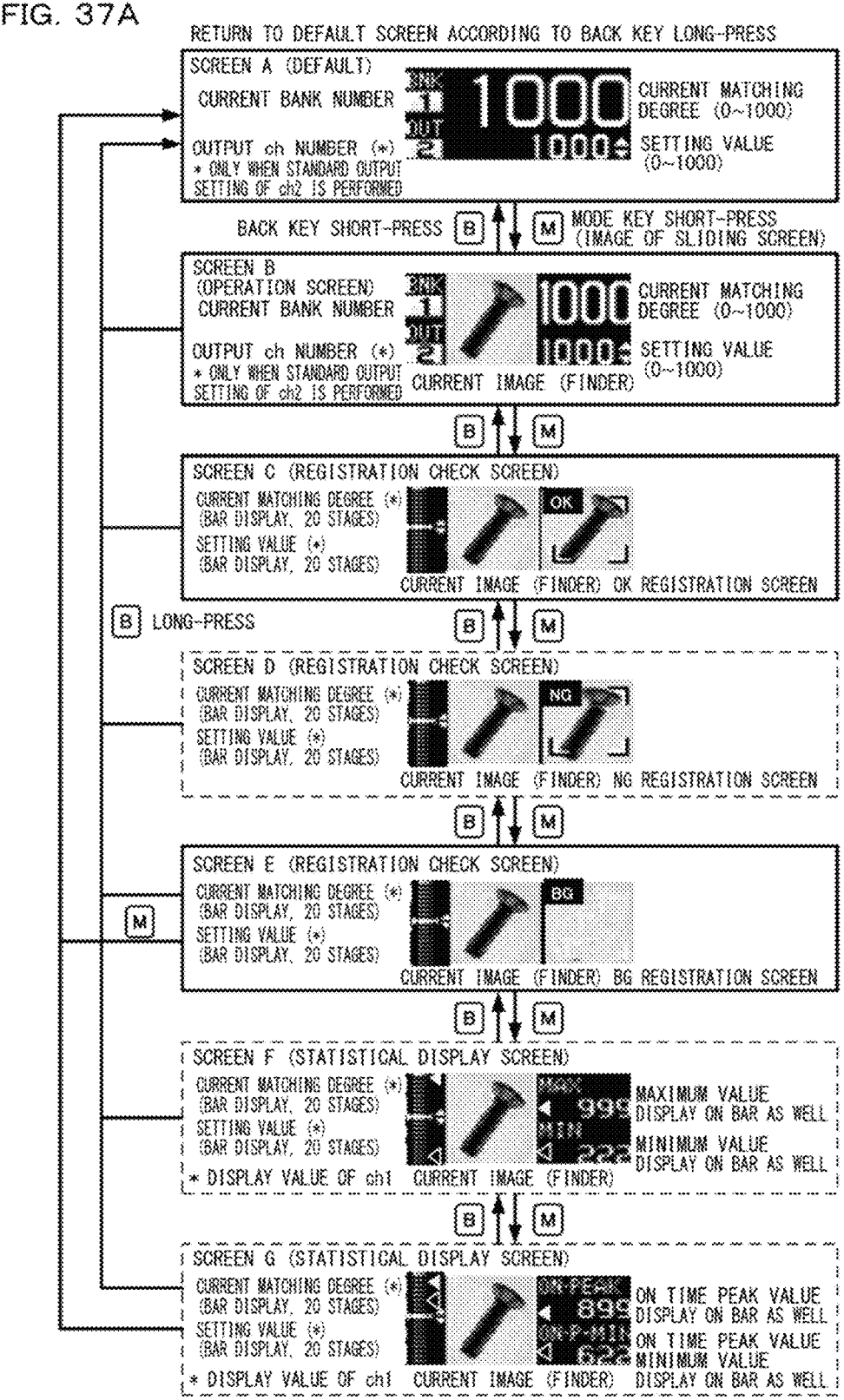
FIG. 37A is a flowchart for explaining an example of screen transition of the operation mode.

Note that the pass/fail determination in this specification is used in meaning including not only operation for determining whether the inspection target object is a non-defective product but also operation for determining whether the inspection target object is a defective product. For example, the pass/fail determination includes, besides a mode in which the pass/fail determining unit 57*d* performs an output when detecting a defective product and does not perform an output while not detecting a defective product, a mode in which the pass/fail determining unit 57*d* performs an output when detecting a non-defective product and does not perform the output while not detecting a non-defective product. An example of a flow of the operation in the operation mode is shown in a flowchart of FIGS. 37A and 37B.

Note that the display of the display unit may be turned off in the operation mode.

Figure 38A:
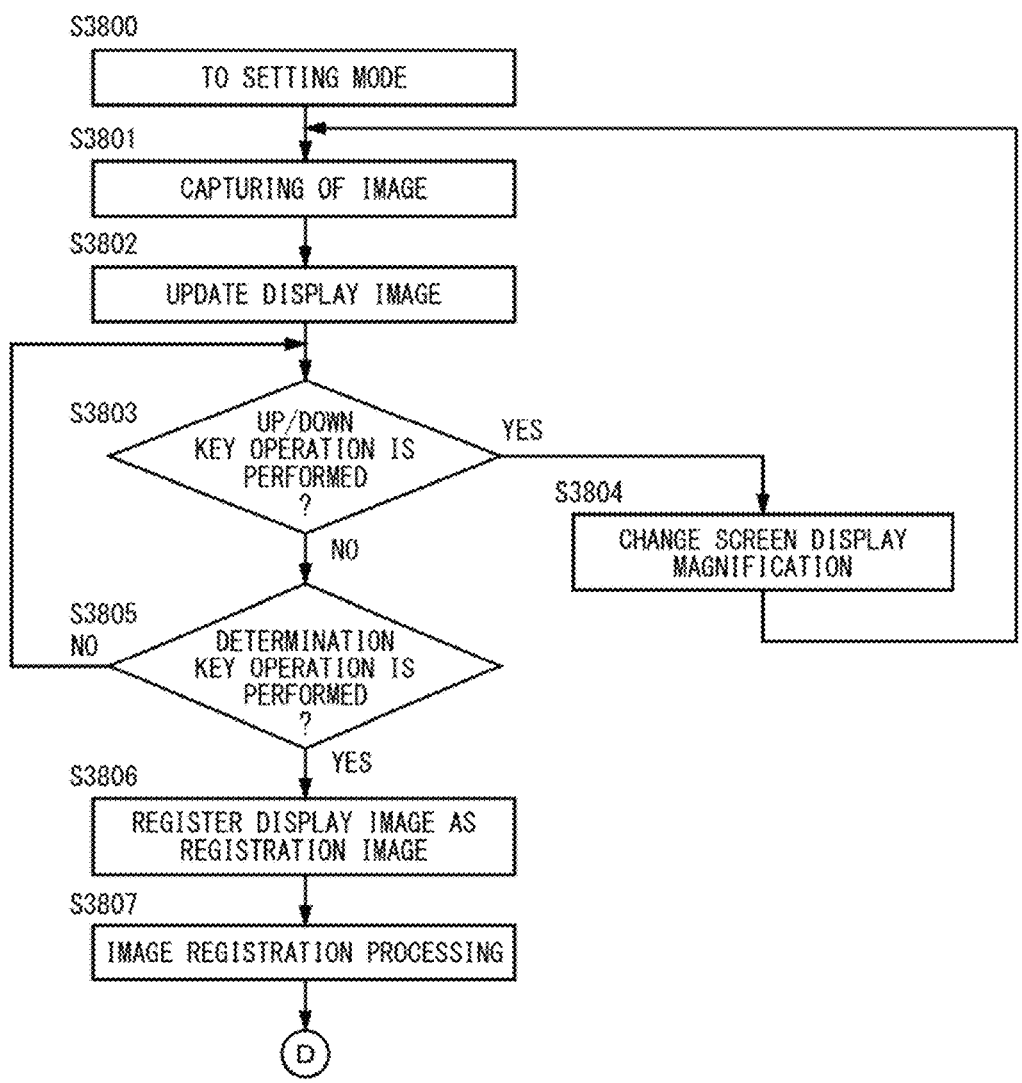
FIG. 38A is a flowchart for explaining the operation of the setting mode including a step for adjusting image display magnification.
Figure 38B:
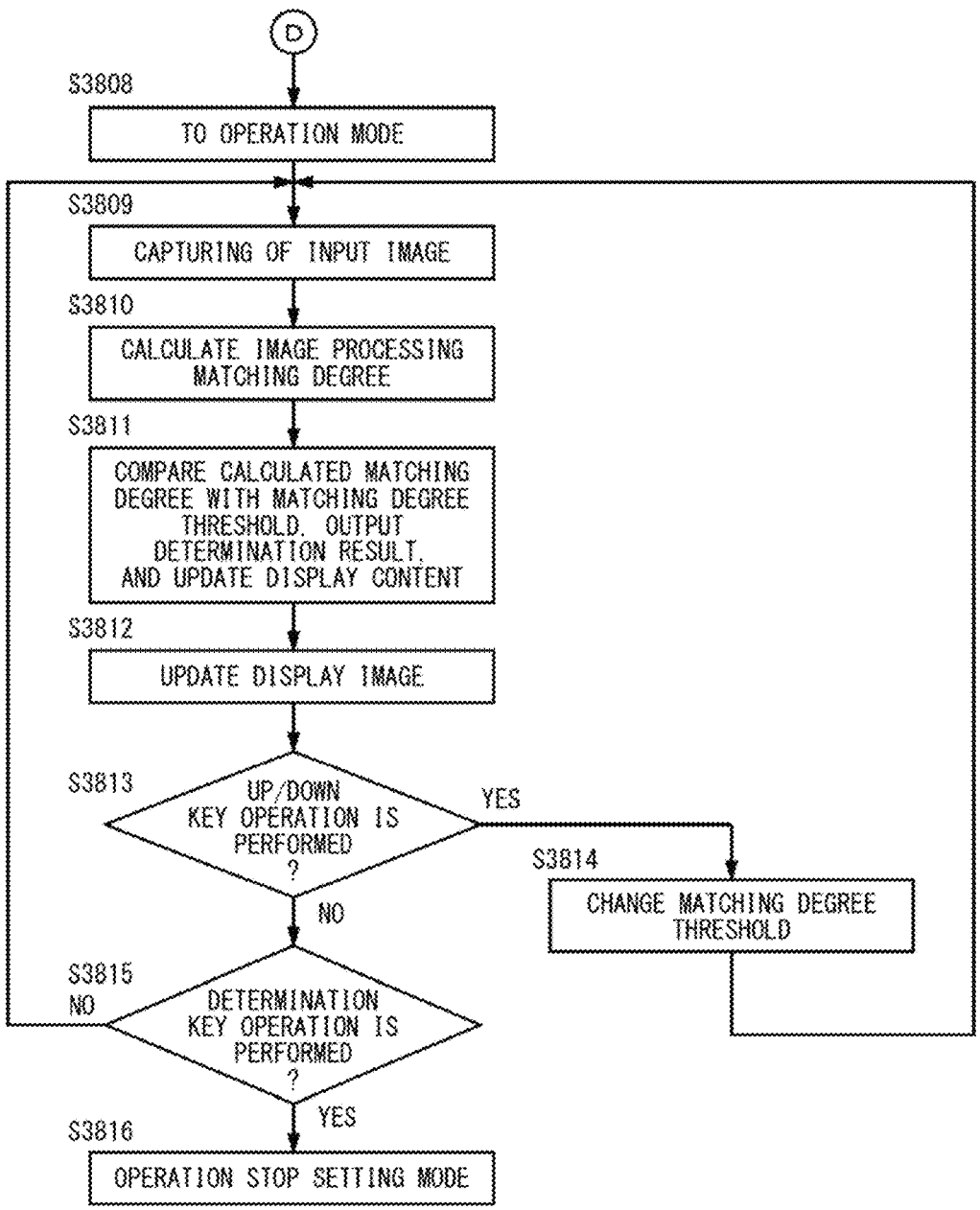
FIG. 38B is a flowchart for explaining the operation of the operation mode including a step of adjusting a matching degree threshold.

On the other hand, during the operation mode, the registration setting conditions can be changed according to, for example, a result of the pass/fail determination. For example, a set matching degree threshold is finely adjusted to reduce wrong determination. In this case, the increase/decrease adjusting unit 51*h* used for the adjustment of the image display magnification can also be used as a member for adjusting the matching degree threshold. Consequently, the adjustment of the image display magnification and the adjustment of the matching degree threshold are performed by the common member provided in the display unit 43 to achieve simplification of a configuration and unity of an operation environment. Such a procedure is explained with reference to a flowchart of FIGS. 38A and 38B. FIG. 38A is a flowchart for explaining the operation of the setting mode including a step of adjusting image display magnification. FIG. 38B is a flowchart including a step of adjusting a matching degree threshold in the operation mode following FIG. 38A. First, in step S3800, the image processing sensor selects the setting mode. Subsequently, in step S3801, the image processing sensor performs capturing of images serving as candidates of a registration target. Further, in step S3802, the image processing sensor performs update of the image displayed on the display unit 43.

As operation on the use side, the user checks the captured candidate images with the display unit 43 and judges whether the candidate images are appropriate as a registration image. When adjustment of a posture and a visual field is necessary, the user performs appropriate processing according to adjustment. For example, when judging that the adjustment of the image display magnification is necessary, the user operates the increase/decrease adjusting unit 51*h* to adjust the display magnification.

As a result, as operation on the image processing sensor side, in step S3804, the image processing sensor determines whether the up/down keys 44, which are the increase/decrease adjusting unit 51*h*, are operated. When the up/down keys 44 are operated, the image processing sensor proceeds to step S3805 and changes the setting to change the image display magnification according to the operation. When the ↑ key 44*a*, which is the switch on the up side, is operated, the image processing sensor increases the image magnification. Conversely, when the ↓ key 44*b*, which is the switch on the down side, is operated, the image processing sensor changes the setting to reduce the image magnification. The image processing sensor returns to step S3801, captures an image again at the changed magnification and causes the display unit 43 to display an image having the magnification after the change. Note that it is not always necessary to perform the capturing of an image again. For example, when increasing the magnification, the image processing sensor may perform digital zoom of the captured image and display the image. Conversely, when reducing the image, since a visual field displayed in the image widens, it is necessary to acquire an image again. However, when images captured in the past are saved, the image processing sensor may be configured to call an image having relevant magnification.

In this way, an image having desired display magnification is obtained. When further magnification adjustment is unnecessary, the up/down keys 44 are not operated in step S3803. Therefore, the image processing sensor proceeds to step S3805 and determines presence or absence of operation of the determination key. The image processing sensor determines presence or absence of depression of the SET key 42, which is a mode of the determination key. When the SET key 42 is not depressed, the image processing sensor returns to step S3804 and repeats the processing. When the depression is detected, the image processing sensor proceeds to step S3806 and registers a displayed image as a registration image. Further, in step S3807, the image processing sensor performs image registration processing. Subsequently, as shown in FIG. 38B, the image processing sensor proceeds to step S3808 and switches the setting mode to the operation mode. In step S3809, the image processing sensor captures an image of work serving as a target of the image processing, that is, the pass/fail determination. Subsequently, in step S3810, the image processing sensor performs predetermined image processing and calculates a degree of matching. In step S3811, the image processing sensor compares the calculated matching degree with the matching degree threshold, outputs a determination result, causes the display unit 43 to display a value of the calculated matching degree, and updates display content of a live image displayed on the display unit 43 (step S3812). In step S3813, the image processing sensor determines presence or absence of operation of the up/down keys 44, which are the increase/decrease adjusting unit 51*h*.

As operation on the user side, the user checks an obtained determination result, the input live image displayed on the display unit 43, and a matching degree calculated with respect to the input live image, and examines whether the determination result is proper and whether the setting of the matching degree threshold is appropriate. When determining that a change of the matching degree threshold is necessary, the user operates the increase/decrease adjusting unit 51*h* to finely adjust the matching degree threshold.

As a result, as operation on the image processing sensor side, when the operation of the up/down keys 44 is detected, the image processing sensor proceeds to step S3814 and changes the matching degree threshold. When the ↑ key 44*a*, which is the switch on the up-side, is operated, the image processing sensor increases the matching degree threshold. Conversely, when the ↓ key 44b, which is the switch on the down-side, is operated, the image processing sensor reduces the matching degree threshold. The image processing sensor returns to step S3809 and performs determination with the changed matching degree threshold. The image processing sensor repeats the operations according to necessity. When determining that an appropriate matching degree threshold is set, in step S3813, the image processing sensor does not detect the operation of the up/down keys 44. The image processing sensor proceeds to step S3815 and determines presence of absence of stop operation of the operation. The image processing sensor detects presence or absence of operation of the determination key. When the operation of the determination key is not detected, the image processing sensor returns to step S3809 and repeats the processing explained above. On the other hand, when the operation of the determination key is detected, the image processing sensor proceeds to step S3816 and stops the operation mode. In this way, it is possible to perform fine adjustment to appropriate display magnification and an appropriate matching degree threshold and improve accuracy of the registration of an image and the pass/fail determination. It is possible to use the increase/decrease adjusting unit 51h common to these kinds of adjustment. In particular, in the setting mode, an adjusting function for image display magnification is automatically allocated to the increase/decrease adjusting unit 51h. On the other hand, in the operation mode, the increase/decrease adjusting unit 51h is changed to an adjusting function for the matching degree threshold. The user obtains an advantage that the user can perform necessary setting simply by focusing on the operation of the increase/decrease adjusting unit 51h without performing operation for switching of the functions of the increase/decrease adjusting unit 51h and without being aware of the switching of the functions.

(Setting of a Resolution Reduction)

In the teaching in the setting mode of the two-point registration, the three-point registration, the one-point registration, and the like explained above, it is possible to reduce image data in resolution in order to increase the speed of arithmetic processing. It is possible to reduce image data in resolution and achieve an increase in the speed of processing not only in the setting mode but also in the operation mode. According to a resolution reduction of an image, it is possible to reduce a data size and achieve a reduction of a load and an increase in the speed of processing such as image processing. Depending on an, image, it is also possible to reduce noise according to processing such as compression and smoothing of the image. In performing such processing, a problem is how to set a degree of the resolution reduction of the image.

Figure 39:
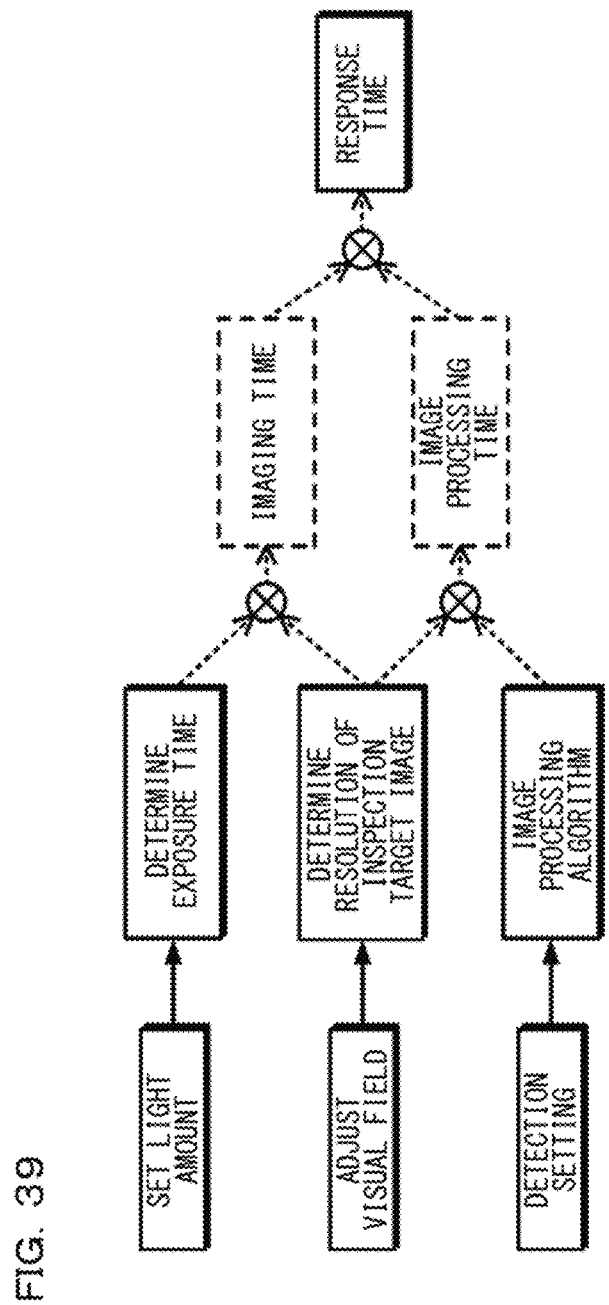
FIG. 39 is a block diagram showing internal processing of a conventional image processing sensor.
Figure 40:
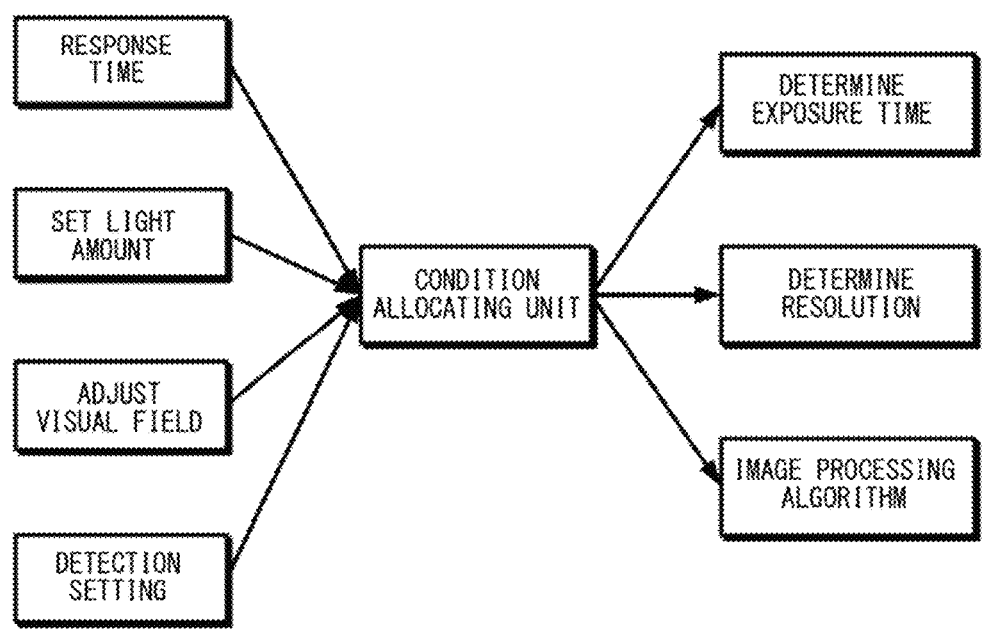
FIG. 40 is a block diagram showing internal processing of an image processing sensor according to an embodiment.

Whereas a response time is sometimes set in the photoelectric sensor in the past, an act of setting the response time is not assumed in the image processing sensor. The response time indicates time required from intrusion of the inspection target object into the imaging visual field of the imaging unit until the output of the determination result by the pass/fail determining unit. Even an image processing sensor that specifies a response time has a characteristic that the response time is distinguished as a result of other set conditions such as a change in the response time based on the visual field region set by the user. The image processing sensor is different from an image processing sensor that optionally sets a response time. On the other hand, for example, in a manufacturing line of a factory, from the viewpoint of conveyance speed and the like of the line, an image processing sensor is often restricted by the presence of an inspection target object and a response time that can be consumed for the pass/fail determination. However, the visual field and the response time cannot be directly set. This is because, since the resolution of a captured optical image directly changes and jitter (fluctuation) occurs in the response time depending on, for example, the setting of the visual field of the user, it is difficult for the image processing sensor to specify the response time. On the other hand, the image processing sensor according to this embodiment is configured to enable the response time to be set irrespective of the enlargement and reduction magnification and determine, on the basis of the set response time, image resolution processed on the inside. The setting of a reduction in resolution is explained in detail below with reference to FIGS. 39 and 40.

In the past, for the setting of the image processing sensor, the user needs to, for example, set a light amount, adjust a visual field, and set image processing serving as a detection target (detection setting). States of operations processed on the inside of the image processing sensor with respect to user designation of the light amount setting, the visual field adjustment, and the detection setting are shown in a block diagram of FIG. 39. As shown in the figure, as a result of the setting of the light amount by the user, an exposure time of the imaging unit 21 is determined. As a result of the adjustment of the visual field, resolution of an optical image of an inspection target is determined. Further, as a result of setting of detection conditions, an algorithm used for the set image processing is determined. As a result, a time necessary for imaging including a time required for readout of the optical image, that is, an imaging time is determined from the exposure time and the resolution of the imaging unit 21. On the other hand, a time required for the image processing, that is, an image processing time is determined from the image resolution and the image processing algorithm. A sum of the imaging time and the image processing time is a response time required for the processing. The response time is determined according to the order explained above.

On the other hand, from a relation of conveyance speed and the like of the manufacturing line, an allowable response time is sometimes determined in advance. In this case, setting itself is impossible depending on setting content. For example, whereas the resolution is spontaneously determined according to the visual field setting of the user, jitter occurs in the response time in which the resolution changes. It is difficult to specify the response time.

On the other hand, the image processing sensor according to this embodiment can set the response time in addition to the visual field and the detection setting. In order to realize the setting of the response time, registration setting conditions such as appropriate image resolution and an image processing algorithm are determined by internal processing of the image processing sensor. Consequently, a data size of a processed image is suppressed irrespective of the visual field setting. The response time can be predefined. A state of the above is explained with referenced to a block diagram of FIG. 40. As shown in the figure, as items that the user can designate, in addition to light amount setting, visual field adjustment, and detection purposes same as those shown in FIG. 39, it is also possible to set the response time. In response to such designation by the user, the condition allocating unit 55 performs optimum allocation, determines an exposure time such that processing ends within a designated response time, determines resolution, and selects an appropriate image processing algorithm.

(Resolution Reduction of an Image)

Figure 41:
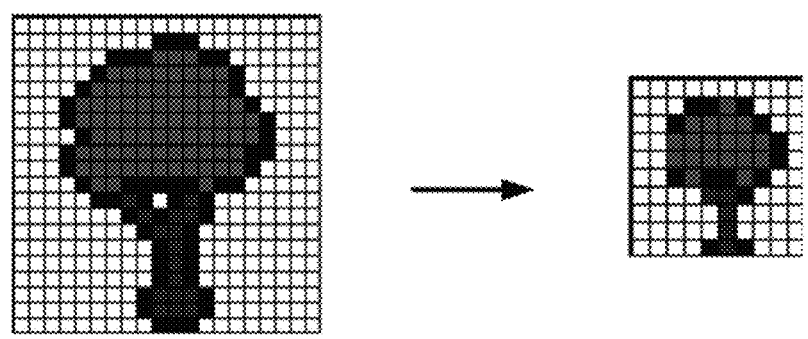
FIG. 41 is a schematic diagram showing a state in which an image is reduced in resolution.

A method of reducing the resolution of an image is explained. As a method of changing resolution to be low, for example, as shown in FIG. 41 with respect to a specified visual field range, there is a method of compressing image data as shown in FIG. 42. In an example shown in FIG. 42, vertical and horizontal sizes are compressed to a half using a pixel value averaged in 2×2 pixels. Alternatively, as shown in FIG. 43, a method of curtailing image data can also be used. In an example shown in FIG. 43, every other pixel values are adopted respectively in the vertical direction and the horizontal direction to compress vertical and horizontal sizes to a half. In the present invention, the method of reducing the image in resolution is not limited to the methods explained above. Known methods of reducing resolution can be adopted as appropriate. In order to realize the resolution reduction, there are a method of using hardware such as a dedicated GPU and a method of realizing the resolution reduction with software. Both of the methods can be used in the present invention. Alternatively, a combination of the methods may be used. In this specification, for convenience of explanation, the resolution reduction is sometimes collectively referred to as compression irrespective of methods such as compression and curtailing.

(3'. Two-Point Registration of the Non-Defective Product Image and the Background Image Including Resolution Reduction Processing)

A procedure in which the condition allocating unit 55 sets, on the basis of a set response time, registration setting conditions such as imaging conditions for an image, a compression degree, and an image processing algorithm such that image capturing to the pass/fail determination can be ended within the response time is explained. In the following explanation, the image-compression-degree setting unit 55*h* of the condition allocating unit 55 adjusts a compression ratio for reducing an optical image in resolution among the registration setting conditions. First, a procedure of setting in the two-point registration including the resolution reduction processing and processing in the operation mode after the setting in the two-point registration of the non-defective product image and the background image explained as 3 above is explained with reference to a flowchart of FIG. 44A.

(Setting of a Response Time)

First, in step S4401, a response time is set. Specifically, the user sets a desired response time from the response-time setting unit 51*e*. The response-time setting unit 51*e* desirably presents candidates of a plurality of different response times to the user in advance and urges the user to select a response time. By presenting, in advance, as a response time candidate group, response times that can be set, it is possible to prepare, for each of the response times, combinations of detection conditions such as an exposure time, resolution (a compression ratio), and an image proceeding algorithm that can be set. It is possible to reduce processing such as calculation in the condition allocating unit 55. In other words, it is possible to quickly eliminate, according to the selected response time, detection conditions such as an exposure time that cannot be set among the registration setting conditions. For example, the image processing sensor causes the display unit 43 to display "Sensor Setting" as a screen for performing setting of the image processing sensor in the setting mode for setting a response time, selects "Response Time", which is a screen for setting a response time among items that can be set, and selects, for example, "20 ms" as a specific response time. It is also possible to configure the image processing sensor to, besides giving choices in advance as setting items such as a response time, cause the user to directly input a desired response time as a numerical value or the like. In this case, the condition allocating unit 55 calculates, on the basis of the input response time, a combination of detection conditions such as an exposure time, resolution, and an image processing algorithm can that be selected.

Subsequently, in step S4402, the image processing sensor acquires a non-defective product image and a background image and saves the non-defective product image and the background image in the image storing unit 54*i*. Examples of optical images of the non-defective product image GDI and the background image BGI obtained in step S4402 are respectively shown in FIGS. 44B and 44C.

Subsequently, in step S4403, the image processing sensor reduces the non-defective product image GDI and the background image BGI in resolution on the basis of the response time set in step S4401. The resolution reduction is performed by, for example, the image compressing unit 56*d*. It is assumed that a compression degree is common to the images. The image compressing unit 56*d* compresses the non-defective product image GDI and the background image BGI. As a result, as shown in FIGS. 44D and 44E, the images are compressed and a compressed non-defective product image CGDI and a compressed background image CBGI having reduced image sizes are obtained.

Subsequently, in step S4404, the image processing sensor generates a compressed non-defective product-background differential image CG-CBDI from the compressed non-defective product image CGDI and the compressed background image CBGI. The generation of the compressed non-defective product-background differential image CG-CBDI is performed by, for example, the differential-image generating unit 56*a*. The compressed non-defective product-background differential image CG-CBDI obtained by the differential-image generating unit 56*a* is as shown in FIG. 44F.

In step S4405, the image processing sensor sets an evaluation region. The evaluation region may be set as, for example, the entire image. A region near the center, a region where the differential image is present, or the like may be automatically set on the image processing sensor side. Alternatively, the user may manually designate the evaluation region. When the user manually designates the evaluation region, for example, an evaluation-region setting unit is provided in the operation unit 51 shown in FIG. 4.

Subsequently, in step S4406, the image processing sensor extracts optimum feature values of the non-defective product image. The extraction of the feature values is performed by, for example, the feature-value extracting unit 56*b*.

Further, in step S4407, the image processing sensor determines a matching degree threshold. For example, the threshold calculating unit evaluates a matching degree with the background image on the basis of the extracted feature values of the non-defective product image to determine the matching degree threshold.

(Operation Mode)

When the setting work in the setting mode ends as explained above, the setting mode is switched to the operation mode. Subsequently, the operation procedure in the operation mode is continuously explained with reference to FIG. 44A. In step S4408, the image processing sensor acquires, with the imaging unit 21, an input live image of work serving as an evaluation target. Subsequently, in step S4409, the image processing sensor reduces the input live image of the evaluation target in resolution. A compression degree of the input live image is set equal to a compression degree of an image in the setting mode. Further, in step S4410, the image processing sensor calculates a matching degree of the work on the basis of the feature values of the non-defective product image registered in the setting mode, compares the matching degree with the matching degree threshold, and performs the pass/fail determination. In this way, it is possible to perform the setting according to the set response time to reduce the resolution and perform the processing in the operation mode within the designated response time.

(3″. Modification of the Two-Point Registration of the Non-Defective Product Image and the Background Image Including the Resolution Reduction Processing)

In the example explained above, the method of setting the matching degree threshold in the order of performing the resolution reduction first during the setting and then generating the differential image is explained. However, the present invention does not limit order of setting the matching degree threshold to the order explained above. For example, an image may be compressed after a differential image is generated first. Such an example is explained as a modification below with reference to a flowchart of FIG. 45A. First, in step S4501, a response time is set. Subsequently, in step S4502, the image processing sensor acquires the non-defective product image GDI and the background image BGI and saves the non-defective product image GDI and the background image BGI in the image storing unit 54i. These steps are the same as steps S4401 and S4402 in FIG. 44A explained above. The non-defective product image GDI and the background image BGI shown in FIGS. 45B and 45C are respectively acquired.

Subsequently, in step S4503, the image processing sensor generates a non-defective product-background differential image from the non-defective product image GDI and the background image BGI. As a result, a non-defective product-background differential image G-BDI shown in FIG. 45D is generated by the differential-image generating unit 56a. In step S4504, the image processing sensor reduces the non-defective product-background differential image G-BDI in resolution according to the response time setting. It is assumed that compression degrees of the images in reducing the resolution in the image compressing unit 56d are common. As a result, a compressed non-defective product-background differential image CG-CBDI, which is a resolution-reduced image of the non-defective-product-background differential image G-BDI, shown in FIG. 45E is obtained by the image compressing unit 56d.

Thereafter, as in steps S4405 to S4410 in FIG. 44A explained above, the image processing sensor sets an evaluation region in step S4505, extracts appropriate feature values of the non-defective product image in step S4506, and sets a matching degree threshold in step S4507. The image processing sensor switches the setting mode to the operation mode after the end of the setting mode. The image processing sensor acquires an input live image serving as an evaluation target in step S4508 and reduces the input live image in resolution in step S4509. A compression degree of the input live image is set equal to the compression degree of the image in the setting mode. In step S4510, the image processing sensor performs the pass/fail determination. In this method, as in the method explained above, it is possible to reduce the differential image in resolution and adjust the image processing time according to the set response time.

(1′. Procedure of Three-Point Registration of the Non-Defective Product Image, the Defective Product Image, and the Background Image Including the Resolution Reduction Processing)

The example is explained above in which the resolution reduction processing is added in the two-point registration. The example is explained in which the non-defective product image and the background image are registered. However, the resolution reduction processing can also be added in the two-point registration for registering the non-defective product image and the defective product image. Further, the resolution reduction processing may be added in three-point registration as well. An example in which the resolution reduction processing is added in three-point registration for registering the non-defective product image, the defective product image, and the background image is explained below with reference to a flowchart of FIG. 46A. First, in step S4601, a response time is set. Subsequently, in step S4602, the image processing sensor acquires a non-defective product image, a defective product image, and a background image. The image processing sensor captures the images with the imaging unit 21. The image processing sensor acquires the non-defective product image GDI, the defective product image NGI, and the background image BGI respectively shown in FIGS. 46B, 46C, and 46D and saves the images in the image storing unit 54i. Subsequently, in step S4603, the image processing sensor reduces the non-defective product image GDI, the defective product image NGI, and the background image BGI in resolution according to the response time setting. The compressed non-defective product image CGDI, the compressed defective product image CNGI, and the compressed background image CBGI compressed by the image compressing unit 56d are respectively as shown in FIG. 46E, FIG. 46F, and FIG. 46G. It is assumed that a compression degree is common to the images.

Subsequently, in step S4604, the image processing sensor generates, with the differential-image generating unit 56a, the compressed non-defective-product-background differential image CG-CBDI, which is the differential image between the compressed non-defective product image CGDI and the compressed background image CBGI, and a compressed defective product-background differential image CN-CBDI, which is the differential image between the compressed defective product image CNGI and the compressed background image CBGI. The compressed non-defective-product-background differential image CG-CBDI and the compressed defective product-background differential image CN-CBDI generated by the differential-image generating unit 56a are respectively as shown in FIG. 46H and FIG. 46I.

In step S4605, the image processing sensor sets evaluation regions respectively in the differential images obtained in this way. Further, in step S4606, the image processing sensor extracts feature values respectively from the evaluation regions of the differential images. Specifically, the image processing sensor extracts, with the feature-value extracting unit 56b, feature values of the non-defective product image from the compressed non-defective-product-background differential image CG-CBDI and extracts, with the feature-value extracting unit 56b, feature values of the defective product image from the compressed defective product-background differential image CN-CBDI. In step S4607, the image processing sensor sets a matching degree threshold. The threshold calculating unit evaluates a matching degree of the defective product image on the basis of the feature values of the non-defective product image to thereby set the matching degree threshold.

When the setting ends in this way, the image processing section is shifted from the setting mode to the operation mode. In the operation mode, in step S4608, the image processing sensor acquires an input live image of an evaluation target. In step S4609, the image processing sensor reduces the acquired input live image in resolution. A compression degree of the input live image is set equal to a compression degree of an image in the setting mode. In step S4610, the image processing sensor performs the pass/fail determination. The image processing sensor calculates a matching degree of the input live image on the basis of the feature values of the non-defective product image. The pass/fail determining unit 57d compares the matching degree with the matching degree threshold to perform the pass/fail determination and outputs a determination result.

In this way, in the three-point registration, as in the two-point registration, by adding the resolution reduction processing, it is possible to end the image processing within the set response time. It is possible to realize the image processing sensor corresponding to inline processing.

(1". Modification of the Three-Point Registration of the Non-Defective Product Image, the Defective Product Image, and the Background Image Including the Resolution Reduction Processing)

The example in which the resolution reduction processing is added in the three-point registration is explained above. In this example, the matching degree threshold is set in the order of performing the resolution reduction first during the setting and then generating the differential image. However, as explained in the two-point registration, the present invention does not limit order of setting the matching degree threshold to this order. In the three-point registration, as in the two-point registration, an image may be compressed after a differential image is generated first. Such an example is explained below with reference to a flowchart of FIG. 47A. First, in step S4701, a response time is set. Subsequently, in step S4702, the image processing sensor acquires a non-defective product image, a defective product image, and a background image and saves the images in the image storing unit 54i. These steps are the same as the steps S4601 and S4602 in FIG. 46A. The non-defective product image GDI, the defective product image NGI, and the background image BGI respectively shown in FIGS. 47B, 47C, and 47D are acquired.

Subsequently, in step S4703, the image processing sensor generates the non-defective product-background differential image G-BDI from the non-defective product image GDI and the background image BGI and generates the defective product-background differential image N-BDI from the defective product image NGI and the background image BGI. As a result, the non-defective product-background differential image G-BDI and the defective product-background differential image N-BDI respectively shown in FIGS. 47E and 47F are obtained. In step S4704, the image processing sensor reduces the non-defective product-background differential image G-BDI and the defective product-background differential image N-BDI in resolution according to the response time setting. It is assumed that compression degrees of the images in reducing the resolution in the image compressing unit 56d are common. As a result, the compressed non-defective product-background differential image CG-CBDI and the compressed defective product-background differential image CN-CBDI, which are resolution-reduced images of the non-defective product-background differential image G-BDI and the defective product-background differential image N-BDI, respectively shown in FIGS. 47G and 47H are obtained.

Thereafter, as in steps S4605 to S4610 in FIG. 46A explained above, the image processing sensor sets an evaluation region in step S4705, extracts appropriate feature values of the non-defective product image and appropriate feature values of the defective product image in step S4706, and sets a matching degree threshold on the basis of the feature values in step S4707. The image processing sensor switches the setting mode to the operation mode after the end of the setting mode. The image processing sensor acquires an input live image serving as an evaluation target in step S4708 and reduces the input live image in resolution in step S4709. A compression degree of the input live image is set equal to the compression degree of the image in the setting mode. In step S4710, the image processing sensor performs the pass/fail determination. In this method, as in the methods explained above, it is possible to reduce the differential image in resolution and adjust the image processing time according to the set response time.

(1'. Procedure of the One-Point Registration of the Background Image Including the Resolution Reduction Processing)

Further, the resolution reduction processing can be added in the one-point registration as well. Such an example is explained with reference to a flowchart of FIG. 48A. First, in step S4801, a response time is set. Subsequently, in step S4802, the image processing sensor acquires a background image. Consequently, the background image BGI shown in FIG. 48B is captured and saved in the image storing unit 54i. Subsequently, in step S4803, the image processing sensor reduces the background image BGI in resolution according to the response time setting. Consequently, the compressed background image CBGI shown in FIG. 48C is obtained. Subsequently, in step S4804, the image processing sensor sets an evaluation region. The entire region of the compressed background image CBGI is set as the evaluation region. In step S4805, the image processing sensor extracts feature values of the compressed background image CBGI. Further, in step S4806, the image processing sensor calculates a matching degree threshold. For example, the threshold calculating unit uniformly sets the matching degree threshold to a matching degree of 50%.

When the setting ends in this way, the image processing sensor is switched from the setting mode to the operation mode. In the operation mode, first, in step S4807, the image processing sensor acquires an input live image of an evaluation target. Subsequently, in step S4808, the image processing sensor reduces the input live image in resolution. A compression degree of the input live image is set equal to the compression degree of the image in the setting mode. In step S4809, the image processing sensor performs the pass/fail determination. The image processing sensor calculates, with the matching-degree calculating unit 57c, a matching degree of the input live image on the basis of the feature values of the background image. The pass/fail determining unit 57d compares the matching degree with the matching degree threshold and performs the pass/fail determination. In this way, it is possible to add the resolution reduction processing in the one-point registration as well and perform the image processing within the set response time.

In the example explained above, the image-compression-degree setting unit of the condition allocating unit adjusts the compression degree for reducing the image in resolution as a registration setting condition such that the processing can be ended within the set response time. However, the present invention does not limit the registration setting condition adjusted by the condition allocating unit to the compression degree of the image. The registration setting condition can be other conditions such as imaging conditions for an image captured by the imaging unit and conditions of image processing. An example is explained below in which the condition allocating unit adjusts imaging conditions.

(Imaging-Condition Allocating Unit)

Ranges of imaging conditions that can be adopted as the registration setting conditions are determined according to the set response time. It is assumed that imaging conditions for an image are adjusted with respect to a response time. In this case, the condition allocating unit 55 functions as the imaging-condition allocating unit 55*d* capable of adjusting imaging conditions for an image captured by the imaging unit such that it is possible to perform predetermined image processing for performing the pass/fail determination within a response time.

(Imaging Conditions)

Examples of the imaging conditions include adjusting an exposure time during imaging by the imaging unit and a light amount (illumination intensity) of illumination light in order to adjust brightness of an image. A gain (e.g., a digital gain value for specifying how many folds the brightness of a CMOS, which is an imaging element, is increased) of the imaging unit, presence or absence a polarization filter, a change in an illumination color, and the like may be included in the imaging conditions. Alternatively, when the imaging unit has a high dynamic range image generating function for combining a plurality of low-gradation images captured by changing a dynamic range of a luminance region to form a high-gradation image, ON/OFF of the HDR function may be included in the imaging conditions. Further, besides parameters during imaging such as ON/OFF of an automatic brightness adjusting function, a pixel skip and curtaining function for increasing a frame rate, a near pixel totalizing and outputting function, and the like and an angle (±180°, etc.) of rotation and inclination, parameters and the like in processing obtained image data can be included in the imaging conditions.

Figure 49A:
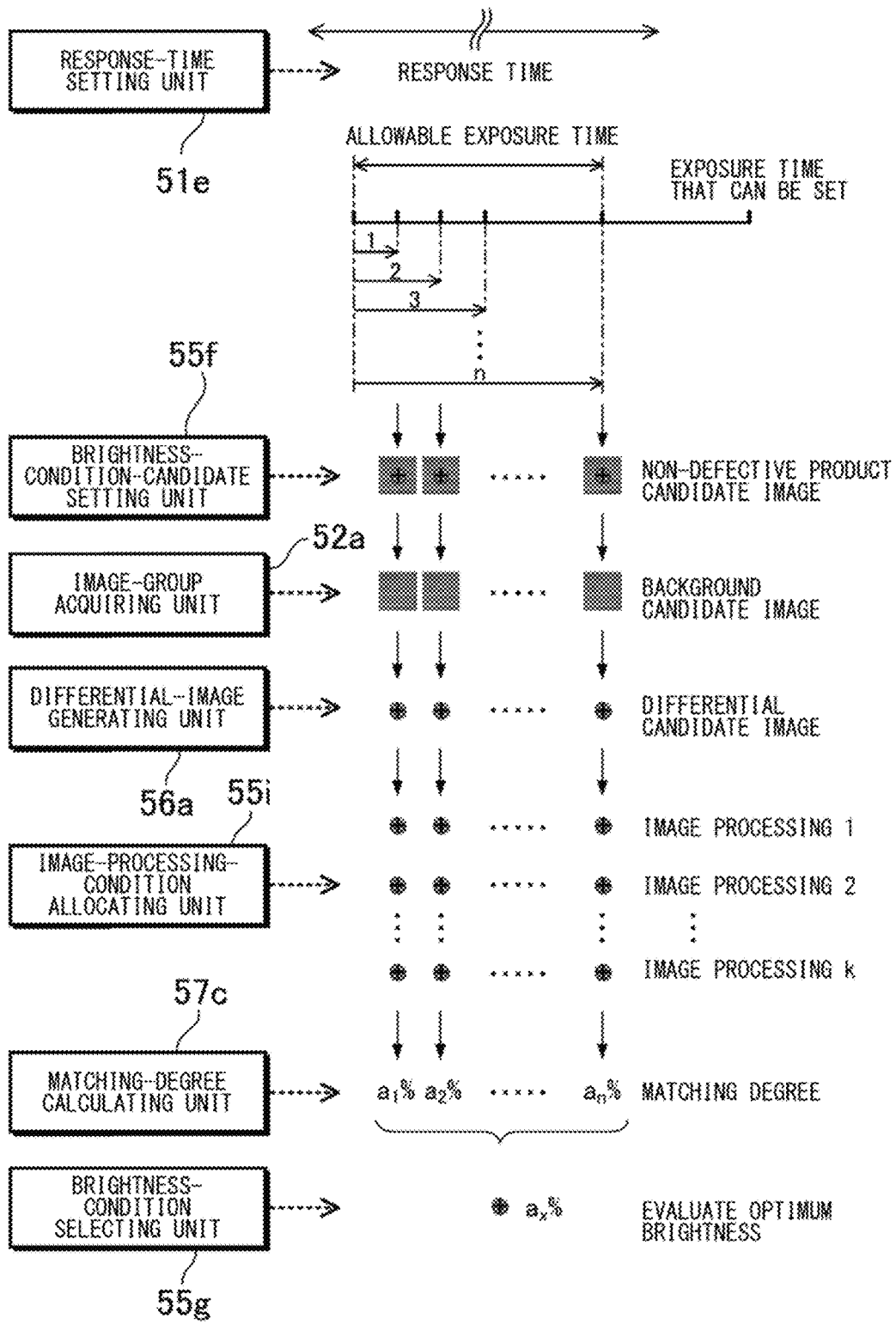
FIG. 49A is a schematic diagram showing a procedure for determining an optimum brightness condition of an image when a response time can be set.

In the following explanation, as a form of the imaging-condition allocating unit 55*d*, a procedure in which the brightness-condition allocating unit 55*e*, that is, the brightness-condition-candidate setting unit 55*f* and the brightness-condition selecting unit 55*g* adjust the brightness of an image and determine an optimum brightness condition is explained with reference to FIG. 49A. First, the response-time setting unit 51*e* sets a response time.

(Determination of Brightness Conditions)

The brightness-condition-candidate setting unit 55*f* and the brightness-condition selecting unit 55*g* determine brightness conditions as the registration setting conditions according to the set response time. In an example shown in FIG. 49A, an example of the two-point registration of the non-defective product image and the background image is shown. First, the brightness-condition-candidate setting unit 55*f* allocates a respective plurality of brightness conditions as brightness condition candidates on the basis of the response time set by the response-time setting unit 51*e* such that a determination result by the pass/fail determining unit 57*d* is output within the response time. That is, an upper limit and a lower limit of an imaging time required for imaging per one image, which can be set by the imaging unit 21, are determined according to the performance, the specification, and the like of an apparatus. On the other hand, an upper limit of the imaging time allowed within the response time is determined from the response time set by the response-time setting unit 51*e*. In this way, an allowable imaging time is determined from the physical specifications of the imaging unit 21 and the given response time. In the imaging time, when transfer and processing abilities of an image are considered to be fixed, an exposure time is a parameter that can be set. A lower limit of the exposure time that can be set is also determined from the specifications and the like. Therefore, a range of time that can be taken as the exposure time is determined. Therefore, the allowable exposure time is changed and a plurality of brightness conditions are set as brightness condition candidates. Specifically, the brightness-condition-candidate setting unit 55*f* extracts brightness condition candidates that can be taken within the range of the allowable exposure time. For example, the range of the allowable exposure time is equally divided by a predetermined number (e.g., five) to set the exposure time. Alternatively, all exposure times that can be set by specifiable width (e.g., 10 ms) are extracted as the brightness condition candidates. In the example shown in FIG. 49A, the brightness-condition-candidate setting unit 55*f* sets brightness condition candidates 1 to n. Note that the brightness condition candidates do not always need to be set at equal intervals. For example, the brightness condition candidates may be densely set in a range in which appropriate brightness can be expected.

(Acquisition of a Candidate Image Group)

Candidate images are acquired for each of a plurality of different brightness condition candidates. The image-group acquiring unit 52*a* controls the imaging unit 21 to capture a plurality of candidate images. The candidate images to be captured are determined according to the setting mode. For example, the image-group acquiring unit 52*a* captures non-defective product candidate images and background candidate images in the two-point registration in which the non-defective product image and the background image are used, captures non-defective product candidate images and defective product candidate images in the two-point registration in which the non-defective product image and the defective product image are used, captures non-defective product candidate images, defective product candidate images, and background candidate images in the three-point registration, and captures background candidate images in the one-point registration. As explained above, the image-group acquiring unit 52*a* urges the user to dispose work for each of the images to be captured. For example, the image-group acquiring unit 52*a* performs guidance display on the display unit 43. When the work is set, the image processing sensor changes the brightness conditions and captures candidate images for each of the brightness condition candidates. Note that setting of the plurality of different brightness condition candidates and work for capturing the candidate images for each of the brightness condition candidates are automatically performed. The user only has to set the work in the screen visual field and removes the work according to guidance in the setting mode without being aware of such setting work. In the example shown in FIG. 49A, in order to perform the two-point registration of the non-defective product image and the background image, the image processing sensor instructs the user to place non-defective work in the screen visual field. A plurality of non-defective product candidate images are captured for each of the different bright condition candidates in a state in which the non-defective work is placed according to the instruction. After the capturing of the non-defective product candidate images, the image processing sensor instructs the user to remove the non-defective work. A plurality of background candidate images are captured in a state in which the user removes the non-defective work according to the instruction. Note that, in the case of the three-point registration, in addition to the above, guidance for instructing the user to place defective work in the screen visual field and work for imaging, for each of the brightness condition candidates, the defective work placed in the screen visual field according to the guidance and capturing defective product candidate images are added.

(Generation of Differential Candidate Images)

Differential candidate images are generated from the acquired candidate images. The differential-image generating unit 56a generates differential candidate images from a pair of candidate images captured under the same brightness condition candidate. In the example shown in FIG. 49A, the differential-image generating unit 56a generates non-defective product-background differential candidate images from the non-defective candidate images and the background candidate images. Note that, in the case of the three-point registration, in addition to the above, work for generating defective product-background differential candidate images from the defective product candidate images and the background candidate images is added.

Note that the differential image and the original image before the differential image generation can be compressed. In this case, the image-compression-degree setting unit 55h adjusts an image compression degree within a given condition.

(Execution of Image Processing: Optional)

The image processing sensor performs predetermined image processing on the differential candidate images according to necessity. The image processing is set in advance as image processing included in the registration setting conditions. The image processing is performed in the image-processing executing unit.

(Allocation of Image Processing Content)

A processing flow of the predetermined image processing performed in order to perform the pass/fail determination of an inspection target object is not limited to one processing flow and can be configured by a plurality of different processing flows. The image-processing-condition allocating unit 55i explained below allocate conditions of the predetermined image processing to each of the plurality of different processing flows. For example, concerning the image processing flow, by allocating the conditions of the image processing, it is possible to evaluate a matching degree calculated from candidate images after the image processing to select optimum image processing. Examples of the conditions of the image processing include a type of a processing module configuring the processing flow of the predetermined image processing and/or image processing parameters referred to in the processing flow. When the conditions of the image processing are allocated, image processing condition candidates are generated by the image-processing-condition allocating unit 55i. The image-processing-condition allocating unit 55i is configured to change the processing module and at least a part of the image processing parameters and allocate the conditions of the predetermined image processing.

(Calculation of a Matching Degree)

Matching degrees are calculated by the matching-degree calculating unit 57c respectively with respect to the differential candidate images subjected to the image processing according to necessity. The matching-degree calculating unit 57c can be configured to calculate a matching degree for each of a plurality of different processing flows. In the example shown in FIG. 49A, the matching-degree calculating unit 57c respectively calculates matching degrees of background candidate images with respect to model images corresponding to the obtained non-defective product-background differential candidate images. Note that, in the case of the three-point registration, the matching-degree calculating unit 57c calculates matching degrees of defective product-background differential candidate images with respect to the model images corresponding to the non-defective product-background differential candidate images.

(Selection of a Brightness Condition)

In a state in which the matching degree is obtained for each of the brightness condition candidates in this way, the image processing sensor selects, with the brightness-condition selecting unit 55g, appropriate brightness conditions according to a selection condition. In the example shown in FIG. 49A, the image processing sensor evaluates brightness conditions using matching degrees of the non-defective product-background differential candidate images and the background candidate images as evaluation values serving as the selection condition. Not that, in the case of the three-point registration, the image processing sensor evaluates the brightness conditions using matching degrees of the non-defective product-background differential candidate images and the defective product-background differential candidate images as evaluation values. The brightness-condition selecting unit 55g selects, for example, out of a plurality of brightness condition candidates, a brightness condition candidate having the lowest matching degree as an optimum brightness condition. By selecting the brightness condition having the lowest matching degree, in the operation mode, the lowest matching degree is further separated from a high matching degree with the non-defective product image. It is easier to set a matching degree threshold.

However, the selection condition is not limited to the lowest matching degree. That is, it is not always necessary to select the brightness condition having the lowest matching degree as the optimum brightness condition. The optimum brightness condition can also be determined taking into account a difference from an adjacent matching degree. For example, as shown in Table 2, when a matching degree is calculated for each of the brightness condition candidates, the matching degree is a matching degree of 40% at the time of a brightness condition 7 according to the lowest matching degree. However, in this case, a difference in a matching degree is large between the brightness condition candidate and an adjacent brightness condition candidate. This indicates that an evaluation value fluctuates when the brightness of illumination changes even a little. In other words, it is surmised that resistance against fluctuation in ambient brightness is weak. On the other hand, if the matching degree is a matching degree of 45% at the time of a brightness condition candidate 3, which is a second lowest matching degree, a difference is relatively small between the brightness condition candidate and the adjacent brightness condition candidate. Consequently, it can be evaluated that the resistance against fluctuation in brightness is excellent. It is evaluated that the brightness condition deserves to be adopted as the appropriate brightness condition. In this way, it is desirable to take into account, as the selection condition for selecting brightness condition candidate, in addition to the low matching degree of the brightness condition candidate, a relatively small difference from a matching degree of a brightness condition candidate near the brightness condition candidate.

TABLE 2

| Brightness condition | Matching degree |
| --- | --- |
| 1 | 55 |
| 2 | 50 |
| 3 | 45 |
| 4 | 50 |
| 5 | 55 |
| 6 | 65 |
| 7 | 40 |
| 8 | 65 |

(Image-Processing-Condition Allocating Unit 55i)

In the example explained above, the procedure for changing the brightness conditions of the image as the imaging conditions and selecting the optimum brightness conditions is explained. As explained above, the condition allocating unit can adjust image processing conditions in addition to such imaging conditions and the compression degree of the image. The image processing conditions include a type of an image processing algorithm to be selected and adjustment of image processing parameters of the selected image processing algorithm. When a condition of the image processing algorithm is changed or adjusted, the condition allocating unit functions as the image-processing-condition allocating unit 55i for changing the conditions of the image processing algorithm executed in the image processing such that a determination result by the pass/fail determining unit 57d is output within a response time. Consequently, it is possible to change a processing load of image processing used for the pass/fail determination to an appropriate load within a response time desired by the user. It is possible to end the image processing within a given time to cope with inline processing and the like.

A procedure in which the condition allocating unit 55 adjusts the image processing conditions as the registration setting conditions according to a response time set by the response-time setting unit 51e is explained. Besides capturing only one optical image with the imaging unit and registering the image in the setting mode, it is also possible to, for each of a plurality of candidate registration setting conditions with registration setting conditions varied, capture images as candidate images and retain the images, select an image suitable for registration out of these plurality of candidate images, and set the image as a registration image. A procedure in which the condition allocating unit 55 captures a plurality of candidate images under a plurality of different candidate registration setting conditions, selects optimum registration setting conditions suitable for the pass/fail determination among the candidate registration setting conditions, and registers a candidate image obtained under the conditions as a registration image is explained with reference to Tables 3 and 4.

A time that can be consumed for capturing of an optical image is spontaneously decided at a stage when the response time is set by the response-time setting unit 51e. That is, an image is captured within the response time, compressed, and subjected to differential processing according to necessity, feature values are calculated, and the pass/fail determination is performed. Therefore, a time allocated to the imaging is limited to a fixed time within the given response time. Therefore, an upper limit of the imaging time is determined according to the response time, that is, an upper limit of an exposure time during the imaging is also determined. A range of an exposure time that can be set is determined according to specifications of hardware such as an imaging element and a camera and software used in the imaging unit 21. Therefore, taking these into account, according to the given response time, an exposure time selectable in the response time is determined within the exposure time that can be set on the imaging unit 21 side in advance. In this way, the condition allocating unit determines a combination of selectable exposure times according to the response time. For example, when a plurality of sets of exposure times are provided in advance, the condition allocating unit 55 extracts a combination of selectable exposure times.

When the response-time setting unit 51e is configured to cause the user to select the response time from a plurality of response time candidate groups prepared in advance rather than any numerical values, a combination of selectable exposure times is determined for each of the response time candidates. Therefore, it is also possible to prepare the exposure times as a table or the like in advance such that a candidate groups of exposure times is automatically extracted according to selection of the response time candidates. With this method, it is possible to reduce processing that should be performed on the condition allocating unit 55 side and realize more inexpensive, lighter-load, or higher-speed processing.

An example of a combination of exposure times with respect to a response time is shown in Table 3. In this way, the number of selectable exposure times increases as the response time is longer. Note that, even after capturing of an image, other processing such as compression of the image, differential processing, and distinction processing is necessary. Therefore, as explained above, the entire response time cannot be consumed for the exposure times.

TABLE 3

|  |  | Exposure time | | | | | | |
|---|---|---|---|---|---|---|---|---|
|  |  | 0.2 ms | 0.8 ms | 1.5 ms | 3 ms | 5 ms | 10 ms | 20 ms |
| Response time | 3 ms | ○ | X | X | X | X | X | X |
|  | 10 ms | ○ | ○ | ○ | X | X | X | X |
|  | 20 ms | ○ | ○ | ○ | ○ | X | X | X |
|  | 50 ms | ○ | ○ | ○ | ○ | ○ | ○ | X |
|  | 100 ms | ○ | ○ | ○ | ○ | ○ | ○ | ○ |

TABLE 4

|  |  | Image processing algorithm type | | | | | |
|---|---|---|---|---|---|---|---|
|  |  | Holistic [A] | Holistic [B] | Search [A] | Search [A] | Search [B] | Search [B] |
|  |  |  |  | Resolution | | | |
|  |  | 40 × 40 | 54 × 54 | 36 × 36 | 54 × 54 | 81 × 81 | 121 × 121 |
| Response time | 3 ms | ○ | X | X | X | X | X |
|  | 10 ms | ○ | ○ | ○ | X | X | X |
|  | 20 ms | ○ | ○ | ○ | ○ | X | X |
|  | 50 ms | ○ | ○ | ○ | ○ | ○ | X |
|  | 100 ms | ○ | ○ | ○ | ○ | ○ | ○ |

As the registration setting conditions, besides the imaging conditions for an image such as the exposure time, instead of or in addition to the imaging conditions, conditions of image processing, a compression degree (resolution) of the image can also be applied. As an example, a combination of an image processing algorithm and resolution with respect to a response time is shown in Table 4. As shown in the table, there are Search and Holistic as an evaluation method for evaluating whether non-defective work specified by differential processing with a background image is present in an operation image. The Search is a method of specifying, from the operation image, a position in a screen of the non-defective work through a pattern search and evaluating a matching degree. On the other hand, the Holistic is a method of identifying the position of the work through comparison of feature values (e.g., a luminance average, contrast, and the number of edge pixels) extracted from the entire image without performing the position specifying processing for the work from the operation image. The Holistic is called overall evaluation as well.

As the Search, there are Search[A], which is a normalized correlation search, for performing a search with a pixel value and Search [B] for performing a search by geometrical information such as a contour. When comparison by an edge feature, which is one of specific feature, is performed in the Holistic, there are Holistic[A] for extracting an edge with a Roberts operator and Holistic[B] for extracting an edge with a Sobel operator. Even if the Search[A] and the Search[B] and the Holistic[A] and the Holistic[B] have the same "resolution and Search" and the same "resolution and Holistic", differences occur in a processing time, identification performance, an operation characteristic, and the like because of processing on the inside. A parameter equivalent to a rotation allowable angle can be included in the image processing during an image search.

In the example shown in Table 4, both of the image processing algorithm and the resolution are adjusted with respect to the response time. However, the present invention is not limited to this. The exposure time, the image processing algorithm, and the resolution can also be adjusted with respect to the response time. As an example, in Table 5, a selectable combination of the exposure time, the image processing algorithm type, and the resolution at the time when the response time (for example, 20 ms) is given is shown. In the table, a circle indicates a selectable combination, a cross indicates an unselectable combination because of the response time, and a cross with half-tone dot meshing indicates an unselectable combination in the combination of the exposure time, the image processing algorithm, and the resolution.

As explained above, a candidate group of selectable registration setting conditions is determined according to the response time. The image processing sensor selects, with the condition allocating unit 55, desirable registration setting conditions out of the candidate group. As explained above, the desirable registration setting conditions are conditions under which a non-defective product and a defective product can be surely distinguished when the pass/fail determination is performed in the operation mode. The pass/fail determining unit 57d performs the pass/fail determination using a matching degree with the non-defective product as an evaluation value. In order to stably separate the non-defective product and the defective product, that is, in order to separate the non-defective product and the defective product as much as possible and set, with the threshold calculating unit, a matching degree threshold in the middle of the non-defective product and the defective product, the registration setting conditions are desirably conditions under which a matching degree with the defective product is calculated as low as possible. Therefore, it is important for the condition allocating unit 55 to obtain registration setting conditions that can achieve such a good registration state, for example, a combination of the exposure time, the resolution, and the image processing algorithm.

Figure 49B:
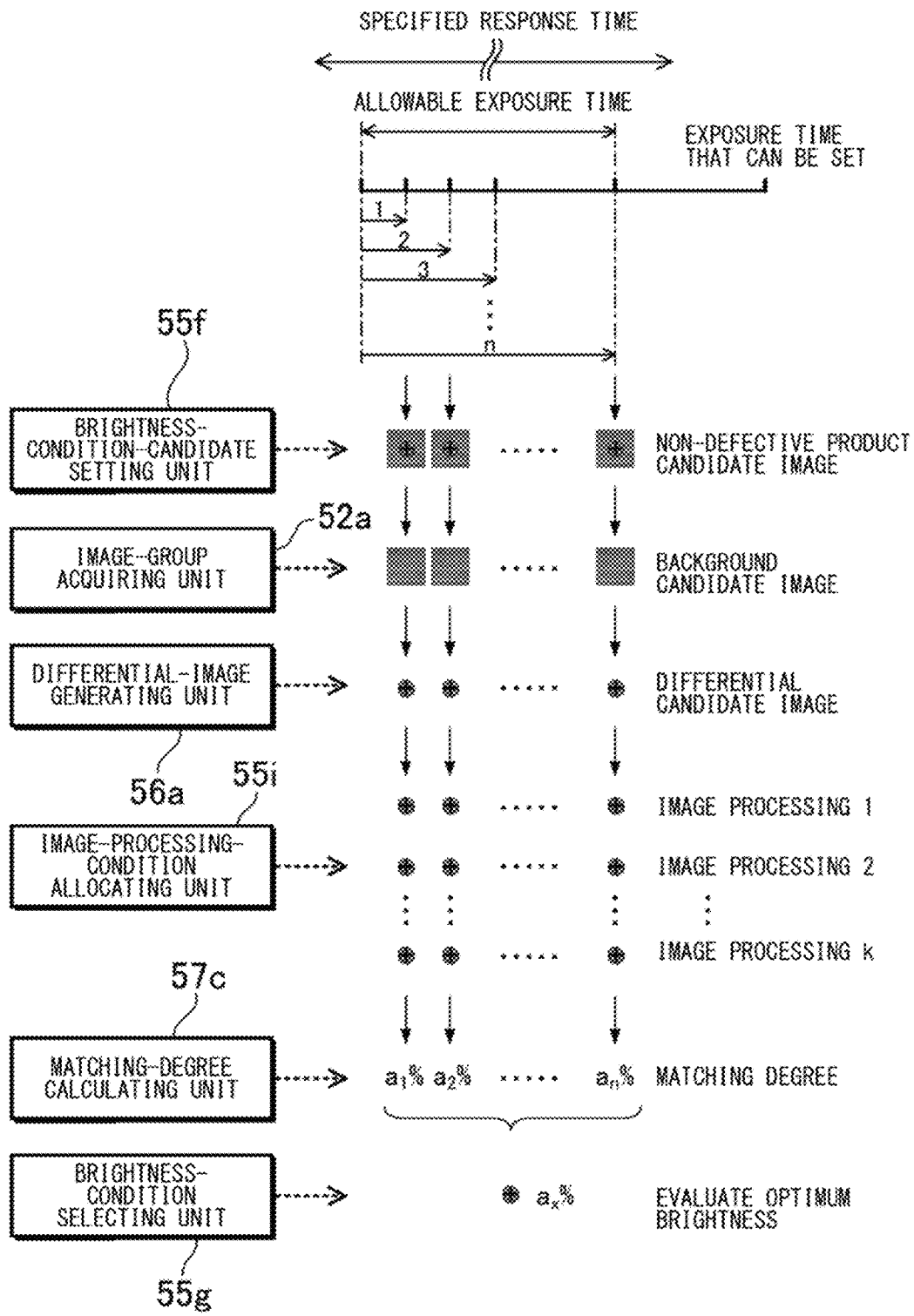
FIG. 49B is a schematic diagram showing a procedure for determining an optimum brightness condition of an image when the response time is a default value.

Note that, in the example explained above, the user can designate the response time from the response-time setting unit. However, the present invention is not limited to this configuration. The response time can be a fixed value. In this case, the response time is given as a default fixed value. Therefore, in FIG. 40, the response time is a default response time. An upper limit of the imaging time, that is, a maximum imaging time is unconditionally determined on the basis of the default response time. Therefore, the condition allocating unit 55 allocates the registration setting conditions such as imaging conditions of an image, a compression degree of a captured image, and an image processing algorithm within a range of the maximum imaging time. Such a procedure is explained with reference to FIG. 49B. Compared with FIG. 49A, in a state shown in FIG. 49B, the response-time setting unit is absent. The response time is given as a default fixed value. Therefore, on the basis of an allowable maximum exposure time unconditionally determined from the default response time, the brightness-condition-candidate setting unit 55f sets brightness conditions and the image-processing-condition allocating unit 55i sets image processing. Alternatively, the image-compression-degree setting unit 55h adjusts an image compression degree. A specific flow of processing is the same as the flow explained above.

TABLE 5

| | | Image processing algorithm type | | | | | |
|---|---|---|---|---|---|---|---|
| | | Holistic [A] | Holistic [B] | Search [A] | Search [A] | Search [B] | Search [B] |
| Response time | | | | Resolution | | | |
| 20 ms | | 40 × 40 | 54 × 54 | 36 × 36 | 54 × 54 | 81 × 81 | 121 × 121 |
| Exposure time | 0.2 ms | ○ | ○ | ○ | ○ | XX | XX |
| | 0.8 ms | ○ | ○ | ○ | ○ | XX | XX |
| | 1.5 ms | ○ | ○ | ○ | X | XX | XX |
| | 3 ms | ○ | ○ | X | X | XX | XX |
| | 5 ms | ○ | ○ | X | X | XX | XX |
| | 10 ms | XX | XX | XX | XX | XX | XX |
| | 20 ms | XX | XX | XX | XX | XX | XX |

○ Selectable
X Unselectable in the combination of the exposure time, the image processing algorithm, and the resolution
XX Unselectable because of the response time (Determination of Optimum Registration Setting Conditions)

Figure 50:
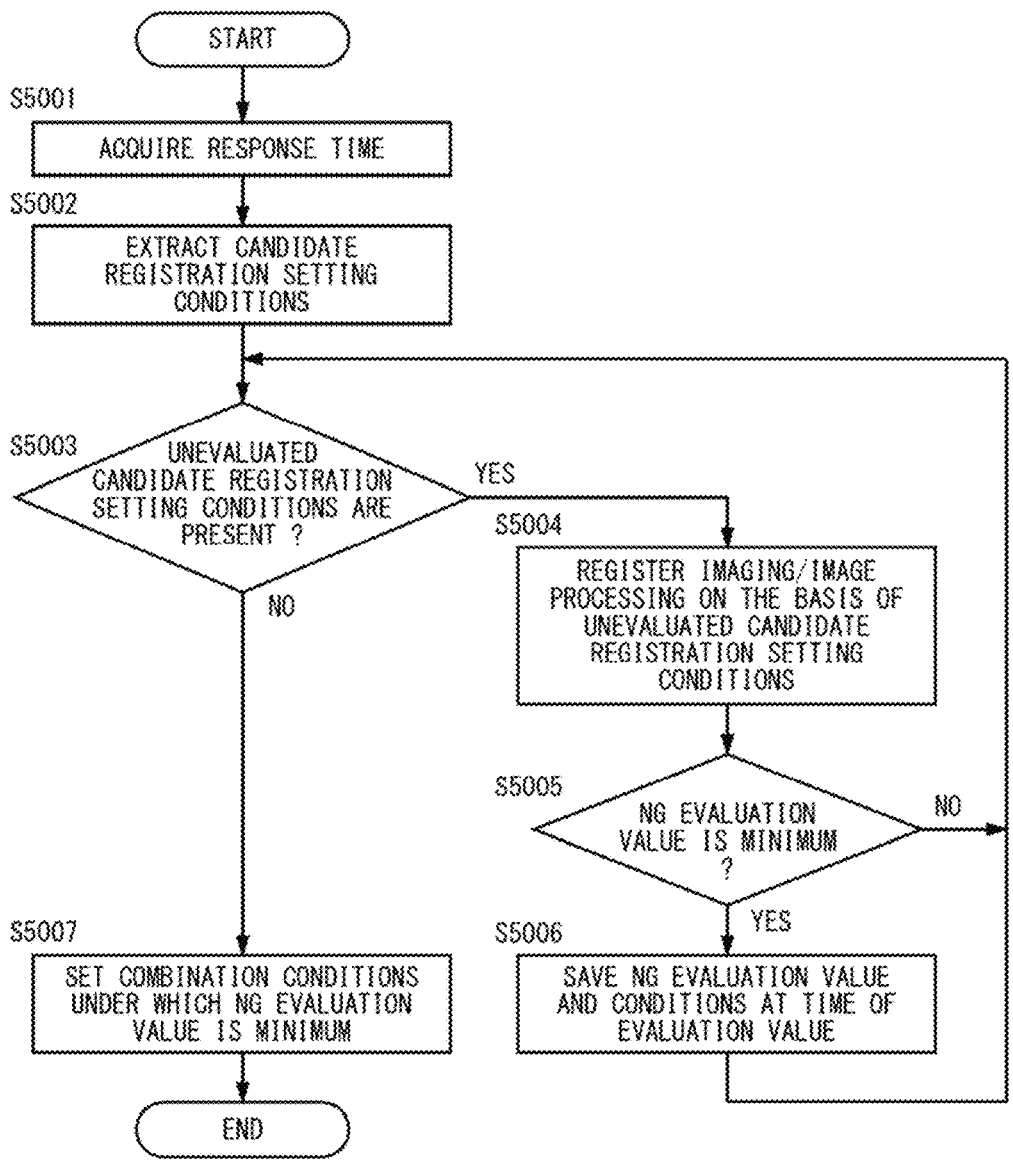
FIG. 50 is a flowchart for explaining a procedure for finding appropriate registration setting conditions from a candidate group of registration setting conditions and performing image registration.

A procedure in which the condition allocating unit 55 finds appropriate registration setting conditions from such a candidate group of registration setting conditions and performs image registration is explained with reference to a flowchart of FIG. 50. First, in step S5001, a response time is acquired. A response time set for the user or a response time of a fixed value set in advance is acquired from the response-time setting unit 51*e*.

Subsequently, in step S5002, the condition allocating unit 55 extracts candidate registration setting conditions according to the response time. As the candidate registration setting conditions, changeable parameters are decided in advance. For example, when an exposure time, resolution, and an image processing algorithm can be adjusted, the condition allocating unit 55 extracts, according to the response time set in step S5001, a combination of an exposure time, resolution, and an image processing algorithm that can be combined is extracted. In this case, combinations of exposure times, resolutions, image processing algorithms that can be set can be prepared as a candidate registration setting condition table with respect to designated response time in advance and saved in the setting saving unit 54*d*. Consequently, by referring to the candidate registration setting condition table, the candidate registration setting conditions including the exposure time, the resolution, and the image processing algorithm that can be set are extracted according to the set response time. In the following steps, images are captured for each of the extracted candidate registration setting conditions, matching degrees are respectively evaluated, and optimum registration conditions are selected out of the obtained matching degrees.

Specifically, first, in step S5003, the condition allocating unit 55 determines whether unevaluated candidate registration setting conditions are present. In a first loop, imaging and an evaluation under the candidate registration setting conditions are not performed yet. Therefore, the condition allocating unit 55 proceeds to step S5004, actually captures an optical images for each of the candidate registration setting conditions, and calculates a matching degree.

Specifically, in step S5004, the condition allocating unit 55 performs capturing of optical images to image processing on the basis of the unevaluated candidate registration setting conditions and calculates a matching degree. This step is the same as the steps in the registration processing during the setting in FIGS. 44A, 45A, 46A, 47A, and 48A and the like explained above. That is, any one of the two-point registration, the three-point registration, and the one-point registration may be used. Further, in order to eliminate a waste of repeating imaging many time under the same imaging conditions (e.g., exposure time), it is also possible to save images as appropriate and read and process the saved images in the case of the same imaging conditions.

Subsequently, in step S5005, the condition allocating unit 55 determines whether an evaluation value of the obtained matching degree is the minimum. Since an evaluation value is not saved in the first loop, the evaluation value of the obtained matching degree is a minimum value. Therefore, the condition allocating unit 55 proceeds to step S5006, saves the evaluation value at this point and the candidate registration setting conditions under which, the evaluation value is obtained, returns to step S5003, and repeats the processing. Thereafter, the condition allocating unit 55 performs imaging and image processing under new candidate registration conditions in the same manner, acquires an evaluation value, and determines in step S5005 whether the evaluation value is a minimum value. When the evaluation value is not the minimum value, the condition allocating unit 55 returns to step S5003 and repeats the evaluation under the next candidate registration setting conditions. On the other hand, when the evaluation value is the minimum value, the condition allocating unit 55 proceeds from step S5005 to step S5006, updates the minimum evaluation value and the candidate registration setting conditions at that point, and then returns to step S5003 and repeats the evaluation. When the evaluation of all the candidate registration setting conditions ends in this way, the condition allocating unit 55 proceeds from step S5003 to step S5007 and sets, as registration setting conditions, the candidate registration setting conditions under which the evaluation value is the minimum. In this way, the condition allocating unit 55 can determine optimum registration setting conditions under which a matching degree of a defective product is the lowest out of the candidate registration setting conditions that can be set in the designated response time.

Note that the meaning of "unevaluated" is explained. For example, it is assumed that, in the three-point registration, an exposure time is changed in ten stages and thirty images in total, that is, ten non-defective product images, ten defective product images, and ten back ground images are captured. In a first loop of step S5003, the condition allocating unit 55 selects an exposure time of ¹⁄₁₀, acquires a non-defective product image, a defective product image, and a background image at the exposure time in step S5004, and thereafter performs the evaluation. In a second loop of step S5003, since the evaluation is already performed concerning the exposure time of ¹⁄₁₀, the condition allocating unit 55 selects, for example, ²⁄₁₀ among the remaining exposure times and performs the acquisition and the evaluation of an image in the exposure time. Further, in a third loop of step S5003, the condition allocating unit 55 further selects another exposure time, performs the same evaluation, thereafter sequentially changes the exposure time, and performs the evaluation concerning all the exposure times.

An example in which the image-processing-condition allocating unit 55*i* configuring the condition allocating unit 55 replaces an image processing algorithm in predetermined image processing is explained with reference to flowchart of FIGS. 51A to 51B. It is assumed that the non-defective product image GDI shown in FIG. 51C, the defective product image NGI shown in FIG. 51D, and the background image BGI shown in FIG. 51E are registered in the setting mode and an input image shown in FIG. 51F is obtained in the operation mode. As shown in the flowchart of FIG. 51A, the image processing is processed in the order of registration processing A in the setting mode and pre-processing B and evaluation processing C in the operation mode. An example is explained in which, in such a series of image processing, the image-processing-condition allocating unit 55*i* changes a part of the image processing and changes the pre-processing B to pre-processing D as shown in FIGS. 51A and 51B.

It is assumed that, in the two-point registration of the non-defective product image and the background image explained above, the image-processing-condition allocating unit 51*i* acquires a non-defective product-background differential image in the setting mode, registers the non-defective product-background differential image as a model image, and calculates a matching degree of the model image and the input image and performs the pass/fail determination in the operation mode.

Specifically, in the registration processing A shown in FIG. 51A, the difference extracting unit extracts a difference from the non-defective product image GDI shown in FIG.

51C and the background image BGI shown in FIG. 51E and cuts out work as shown in FIG. 51G. Further, the difference extracting unit extracts feature values of the work from an obtained image of the work. For example, the feature-value extracting unit 56b calculates a luminance average value of 75, luminance dispersion of 30, the number of edge pixels of 50, and the like as feature values from the image of the work shown in FIG. 51G. After performing the registration processing A in advance in the setting mode in this way, the image-processing-condition allocating unit 51i performs the pre-processing B and the evaluation processing C in the operation mode. Note that processing that needs to be performed within a designated response time, in other words, image processing that needs to be reduced in time is not the processing in the setting mode and is the pre-processing B and the evaluation processing C in the operation mode.

In the pre-processing B, in an evaluation image (FIG. 51F) of an evaluation target obtained as an input image, the image-processing-condition allocating unit 51i searches for the work (FIG. 51G) cut out in the registration processing A. Consequently, the work is specified from the evaluation image as shown in FIG. 51H.

In the evaluation processing C, the image-processing-condition allocating unit 51i extracts and evaluates feature values with respect to a work region (FIG. 51J) cut out from the evaluation image (FIG. 51H). Further, the image-processing-condition allocating unit 51i compares the feature values with feature values already extracted in the registration processing A and calculates a matching degree. For example, the feature-value extracting unit 56b calculates, as feature values, the luminance average value of 70, the luminance dispersion of 30, the number of edge pixels of 55, and the like from the work region shown in FIG. 51J. The pass/fail determining unit 57d compares the obtained feature values of the work region and the feature values of the image of the work explained above and performs the pass/fail determination.

In the image processing explained above, a processing time in the pre-processing B is long. Therefore, when a set response time is short, the pre-processing B and the evaluation processing C sometimes cannot be ended within the response time in the operation mode. In this case, as shown in FIG. 51B, the image-processing-condition allocating unit 55i changes the pre-processing B to the pre-processing D having a lighter load. In the pre-processing D, for example, as shown in FIG. 51I, the image-processing-condition allocating unit 51i performs differential processing with the background image BGI (FIG. 51E) instead of performing a search for a work image on the evaluation image (FIG. 51F). Consequently, it is possible to cut out, from the evaluation image shown in FIG. 51F, a region of the work as shown in FIG. 51I. Consequently, for a common purpose of removal of a background from the valuation image, the image search is replaced with the pre-processing more simplified than the image search. Consequently, a reduction in processing time is achieved. It is possible to end the image processing within the response time.

(Change of Constituent Elements of the Image Processing Algorithm)

Figure 52A:
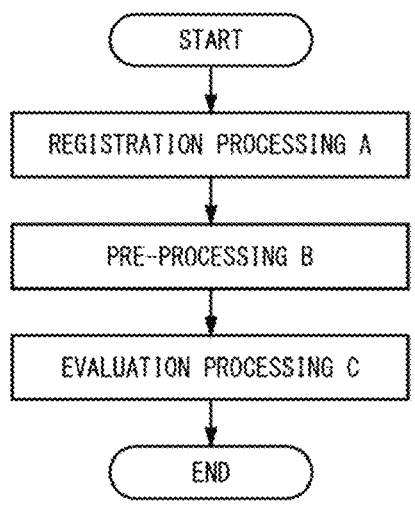
FIG. 52A is a flowchart for explaining a series of image processing before replacement of constituent elements of the image processing algorithm and FIG. 52B is a flowchart for explaining a series of image processing after the replacement of the constituent elements of the image processing algorithm from FIG. 52A.
Figure 52B:
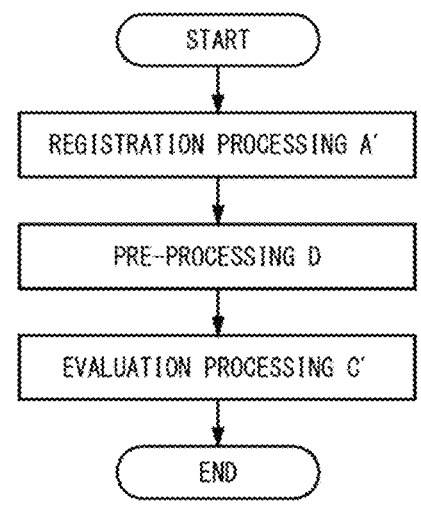

In the example explained above, the method is explained in which the image-processing-condition allocating unit 55i replaces the image processing algorithm in the image processing. However, a method in which the image-processing-condition allocating unit 55i changes the conditions of the image processing is not limited to the replacement of the image processing algorithm and can be other methods. As another example in which the image-processing-condition allocating unit 55i changes the conditions of the image processing, an example in which the image-processing-condition allocating unit 55i changes constituent elements of the image processing flow is explained with reference to flowcharts of FIGS. 52A and 52B. It is assumed that images treated in this example (the non-defective product image GDI, the defective product image NGI, the background image BGI, and an evaluation image) are the same as the images shown in FIGS. 51C to 51F and a series of image processing before the conditions of the image processing are changed is as shown in FIG. 52A and is the same as the image processing shown in FIG. 51A explained above.

First, in registration processing A' in the setting mode after a change, the image-processing-condition allocating unit 51i specifies work according to a difference between the non-defective product image GDI (FIG. 51C) and the background image BGI (FIG. 51E) and further extracts feature values of work. The image processing is the same as the registration processing A shown in FIG. 51A (FIG. 52A). However, in the extraction of the feature values, in the registration processing A', image processing parameters of the image processing algorithm are changed from the image processing parameters in the registration processing A. Specifically, in the registration processing A, the image-processing-condition allocating unit 51i uses a Sobel filter for extraction of an "edge feature" among the feature values. On the other hand, in the registration processing A' shown in FIG. 52B, the image-processing-condition allocating unit 51i uses a 2×2 Roberts filter for the extraction of the "edge feature".

As the Sobel filter, as shown in FIGS. 53A and 53B, the image-processing-condition allocating unit 51i applies two filters of Sobel X (FIG. 53A) and Sobel Y (FIG. 53B) to eight pixels near a target pixel. Thereafter, when an X component of an edge applied with the Sobel X and a Y component of an edge applied with the Sobel Y are respectively represented as Sx and Sy (FIG. 53C), the image-processing-condition allocating unit 51i calculates intensity=$\sqrt{(Sx^2+Sy^2)}$ and an angle=Arctan(Sy/Sx). Note that a 3×3 Sobel filter is used. However, the Sobel filter is not limited to this. For example, other Sobel filters such as a 5×5 Sobel filter may be used.

On the other hand, the Roberts filter is image processing obtained by simplifying the Sobel filter. Specifically, the image-processing-condition allocating unit 51i applies, instead of the Sobel X and the Sobel Y, filters of Roberts X and Roberts Y shown in FIGS. 54A and 54B obtained by simplifying the Sobel X and the Sobel Y. The image-processing-condition allocating unit 51i calculates, as in the Sobel filter, intensity=$\sqrt{(Sx'^2+Sy'^2)}$ and an angle=Arctan (Sy'/Sx') from Sx' and Sy' (FIG. 54C), which are an X component of an edge applied with the Roberts X and a Y component of an edge applied with the Roberts Y. As a result, as the feature values of the work, for example, the luminance average value of 75, the luminance dispersion of 30, the number of edge pixels of 50, and the like are calculated.

After performing the image processing in the setting mode first in this way, the image-processing-condition allocating unit 51i performs the pre-processing B and the evaluation processing C and C', which are the image processing in the setting mode. In the pre-processing B, in both of FIGS. 52A and 52B, as in the pre-processing B shown in FIG. 51A, the image-processing-condition allocating unit 51*i* searches for cut-out work in the evaluation image (FIG. 51F) and cuts out the work from the evaluation image (FIG. 51H).

Further, in the evaluation processing C and C', the image-processing-condition allocating unit 51*i* extracts and evaluates features of the work region (FIG. 51J) cut out from the evaluation image. In the evaluation processing C shown in FIG. 52A, a Sobel filter same as the Sobel filter in the registration processing A is used. On the other hand, in the evaluation processing C' shown in FIG. 52B after the change, a Roberts filter same as the Roberts filter in the registration processing A is used. The image-processing-condition allocating unit 51*i* compares feature values of the evaluation image obtained using the Roberts filter with the feature values already extracted in the registration processing A and calculates a matching degree. In this way, it is possible to reduce the processing time by simplifying the method of the edge extraction with respect to the common image processing of the edge extraction, which is one of the constituent elements of the image processing, and ends the image processing within the set response time.

In the example explained above, the example is explained in which the image-processing-condition allocating unit performs one of the change of the image processing algorithm itself and the change of the constituent elements of the image processing algorithm. However, the present invention is not limited to this. For example, the change of the image processing algorithm and the change of the constituent elements of the image processing algorithm can be combined. Besides changing already set image processing content according to a response time, the image-processing-condition allocating unit can also use the image processing content for initial operation for allocating appropriate image processing in a state in which a response time is given in advance.

Further, a change of the image processing parameters in the image processing algorithm may be applied. For example, a size of the Sobel filter may be changed from 3×3 to 5×5 and the like. In this way, the image-processing-condition allocating unit 55*i* can change a filter size of an edge filer for edge extraction of a non-defective product image in the setting mode and edge extraction of an input image in the operation mode.

Note that, besides being configured by a single image processing algorithm, the image processing may be configured by a plurality of different image processing algorithms. In both the cases, the image-processing-condition allocating unit can change all or a part of the image processing algorithms and the image processing parameters such that a determination result by the pass/fail determining unit 57*d* is output within the response time.

The matching-degree calculating unit 57*c* may be configured to calculate, in the operation mode, a matching degree of an input image to a model image for each of the plurality of different image processing algorithms.

Further, in the example explained above, in the two-point registration of the non-defective product image and the background image, the non-defective product-background differential image is used as the model image. However, the present invention is not limited to this. For example, in the two-point registration of the non-defective product image and the defective product image, a non-defective product-defective product differential image may be used as the model image. Alternatively, in the three-point registration of the non-defective product image GDI, the defective product image NGI (FIG. 51D), and the background image BGI, when the model image corresponding to the non-defective product-background differential image and the model image corresponding to the defective product-background differential image are registered in the setting mode and matching degrees of the model image of the non-defective product-background differential image and the model image of the defective product-background differential image and the input image are respectively calculated and the pass/fail determination is performed in the operation mode, the image-processing-condition allocating unit can also change the conditions of the image processing. Alternatively, in the one-point registration for registering the background image, when the background image is set as the model image and a matching degree with the input image is calculated, the image-processing-condition allocating unit can change the conditions of the image processing.

In the example explained above, the matching-degree calculating unit 57*c* calculates the matching degree indicating the degree of matching of the feature values of the model image and the input image. The model image serving as a base for calculating the matching degree is configured according to the non-defective product image, the defective product image, and the background image registered by the image/setting storing unit 54. For example, the model image can be various differential images, compressed differential images obtained by compressing the differential images, or an edge image. Instead of the model image, feature values may be calculated on the basis of information other than images. For example, the matching-degree calculating unit may calculate a matching degree on the basis of feature values such as an edge and luminance. In this way, a base of the calculation of the matching degree by the matching-degree calculating unit is not always limited to image data. Other information including feature values such as an edge and luminance can also be used. In this specification, the information forming the base of the matching degree calculation is referred to as pattern model.

With the image processing sensor, the image processing method, the image processing program, and the computer-readable recording medium and the device having the image processing program recorded therein, it is possible to suitably perform a non-defective product inspection and a defective product inspection using images having a fixed spread instead of a photoelectric sensor set in a manufacturing line.

What is claimed is:

1. An image processing sensor for performing predetermined image processing on an image of an inspection target object to detect that the inspection target object is a non-defective product or a defective product, the image processing sensor comprising:
   an imaging unit configured to image the inspection target object;
   a display unit configured to display a live image of the inspection target object acquired by the imaging unit;
   an operation unit configured to receive an instruction for storing as a still image in a memory the live image displayed by the display unit so as to register the live image;
   a threshold calculating unit configured to calculate a threshold with respect to a matching degree indicating a degree of feature matching of a first image that includes the inspection target object that represents the non-defective product and a second image that represents an image other than the non-defective product, the first image and the second image being registered according to the instruction received by the operation unit; and a display control unit configured to cause the display unit to display the first image and the second image as the still image used for the calculation of the threshold by the threshold calculating unit, wherein the display control unit causes the display unit to display, on a first registration screen for registering the live image corresponding to one image of the first image and the second image, the live image acquired by the imaging unit and, after receiving, with the operation unit, an instruction for registering the live image corresponding to the one image in a state in which the live image corresponding to the one image is displayed on the first registration screen, the display control unit causes the display unit to display, on a second registration screen for registering the live image corresponding to the other image of the first image and the second image, the live image acquired by the imaging unit and the already registered one image as the still image.

2. An image processing sensor for performing predetermined image processing on an image of an inspection target object to detect that the inspection target object is a non-defective product or a defective product, the image processing sensor comprising:

an imaging unit configured to image the inspection target object;

a display unit configured to display a live image of the inspection target object acquired by the imaging unit;

an operation unit configured to receive an instruction for storing as a still image in a memory the live image displayed by the display unit so as to register the live image;

an image registering unit configured to register, on the basis of the instruction from the operation unit, the live image corresponding to a non-defective product image or a model image and the live image corresponding to a defective product image, wherein the non-defective product image includes the inspection target object that represents the non-defective product displayed on the display unit, the model image serving as a reference of pass/fail determination and generated on the basis of the non-defective product image, and the defective product image including the inspection target object that represents the image of the defective product displayed on the display unit;

a threshold calculating unit configured to calculate a threshold with respect to a matching degree indicating a degree of feature matching of the non-defective product image and the defective product image registered by the image registering unit; and a display control unit configured to cause the display unit to display the non-defective product image and the defective product image as the still image used for the calculation of the threshold by the threshold calculating unit, wherein the display control unit causes the display unit to display, on a first registration screen for registering the live image corresponding to one image of the non-defective product image and the defective product image, the live image, acquired by the imaging unit and, after receiving, with the operation unit, an instruction for registering the live image corresponding to the one image in a state in which the live image corresponding to the one image is displayed on the first registration screen, the display control unit causes the display unit to display, on a second registration screen for registering the live image corresponding to the other image of the non-defective product image and the defective product image, the live image acquired by the imaging unit and the already registered one image as the still image.

3. The image processing sensor according to claim 1, wherein the display control unit causes the display unit to display, on the second registration screen, the live image and the still image side by side on the same screen.

4. The image processing sensor according to claim 1, wherein timing when the display control unit transitions the first registration screen to the second registration screen is set the same as timing when the display control unit registers, with the image registering unit, the one image as the sill image on the first registration screen.

5. The image processing sensor according to claim 1, wherein timing when the display control unit transitions the first registration screen to the second registration screen is set different from timing when the display control unit registers, with the image registering unit, the one image as the sill image on the first registration screen.

6. The image processing sensor according to claim 2, wherein the image registering unit registers, on the basis of the instruction from the operation unit, as a background image, an image of a background from which a feature portion of the non-defective product in the inspection target object displayed on the display unit is removed.

7. The image processing sensor according to claim 6, wherein the threshold calculating unit calculates the threshold on the basis of a first differential image calculated from the non-defective product image and the background image and a second differential image calculated from the defective product image and the background image.

8. The image processing sensor according to claim 6, wherein the display control unit transitions the first registration screen and the second registration screen to a third registration screen for registering the background image on the basis of an instruction from the operation unit.

9. The image processing sensor according to claim 8, wherein the display control unit causes the display unit to display the background image as the live image on the third registration screen.

10. The image processing sensor according to claim 1, further comprising a magnification adjusting unit configured to adjust magnification of the image displayed on the display unit, wherein the display control unit causes the display unit to display, on the first registration screen, the one image as the live image at the magnification set by the magnification adjusting unit and causes the display unit to display, on the second registration screen, the other image as the live image at the magnification used on the first registration screen.

11. The image processing sensor according to claim 1, wherein the display control unit is capable of displaying, on the display unit, the threshold calculated by the threshold calculating unit, and the image processing sensor further comprises a threshold adjusting unit configured to adjust the threshold displayed on the display unit.

12. The image processing sensor according to claim 11, wherein
the display control unit causes, when causing the threshold adjusting unit to adjust the threshold, the display unit to display a matching degree of the defective product image with respect to the non-defective product image.

13. The image processing sensor according to claim 12, wherein
the display control unit causes, when causing the threshold adjusting unit to adjust the threshold, the display unit to display a matching degree of the non-defective product image as a fixed value.

14. The image processing sensor according to claim 1, wherein
the display unit is configured by an organic EL element.

15. The image processing sensor according to claim 1, further comprising an operation/setting-mode switching unit configured to switch an operation mode for distinguishing pass/fail of the inspection target object with the pass fail determining unit and a setting mode for calculating a threshold used in the operation mode, wherein
the display control unit causes, in the setting mode and the operation mode, the display unit to display, in positions respectively corresponding to the setting mode and the operation mode, image display regions where the image is displayed.

16. The image processing sensor according to claim 15, wherein
in a state in which the image processing sensor is switched to the operation mode by the operation/setting-mode switching unit, the image processing sensor is capable of displaying, on the display unit, the threshold calculated by the threshold calculating unit and a matching degree.

17. The image processing sensor according to claim 15, wherein
in a state in which the image processing sensor is switched to the operation mode by the operation/setting-mode switching unit, the display control unit causes the display unit to display the live image of the inspection target object and the already registered still image on the same screen of the display unit.

18. The image processing sensor according to claim 1, wherein
the display control unit causes the display unit to display, in an image display region where the image is displayed, guide lines serving as indicators for positioning in placing the inspection target object in an imaging position.

19. The image processing sensor according to claim 1, wherein
the display control unit is capable of displaying, on the display unit, registration order information indicating registration order for performing image registration of the first image and the second image.

20. An image processing method for performing predetermined image processing on an image of an inspection target object to detect that the inspection target object is a non-defective product or a defective product, the image processing method comprising:
a step of capturing, with an imaging unit, a non-defective product image that includes the inspection target object that represents the non-defective product or an image serving as a reference of pass/fail determination generated on the basis of the non-defective product image, causing a display unit to display the non-defective product image or the image as a live image on a first registration screen, and registering of the non-defective product image or the image as a first image; and
a step of, after receiving an instruction for registering the first image from an operation unit, causing the display unit to display the registered first image as a still image, and, imaging a second image, with the imaging unit, as a second image registration screen, for registering the second image that represents an image other than the non-defective product, causing the display unit to display the second image registration screen as the live image side by side with the still image, and urging registration of the second image.

21. An image processing program for performing predetermined image processing on an image of an inspection target object to detect that the inspection target object is a non-defective product or a defective product, the image processing program causing a computer to realize:
a function of acquiring, with an imaging unit, a non-defective product image that includes the inspection target object that represents the non-defective product or an image serving as a reference of pass/fail determination generated on the basis of the non-defective product image, causing a display unit to display the non-defective product image or the image as a live image on a first registration screen, and registering of the non-defective product image or the image as a first image; and
a function of, after receiving an instruction for registering the first image from an operation unit, causing the display unit to display the registered first image as a still image, and, imaging a second image, with the imaging unit, as a second image registration screen, for registering the second image that represents an image other than the non-defective product, causing the display unit to display the second image registration screen as the live image side by side with the still image, and urging registration of the second image.

22. A non-transitory, tangible computer-readable recording medium having the computer program according to claim 21 recorded therein or a device having the computer program according to claim 21 stored therein.

* * * * *